(12) United States Patent
Taniguchi et al.

(10) Patent No.: US 6,300,344 B1
(45) Date of Patent: *Oct. 9, 2001

(54) HETEROCYCLIC COMPOUNDS

(75) Inventors: Kiyoshi Taniguchi, Kobe; Kouji Hattori, Takarazuka; Kazunori Tsubaki, Uji; Osamu Okitsu; Seiichiro Tabuchi, both of Nishinomiya, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/357,664

(22) Filed: Jul. 20, 1999

Related U.S. Application Data

(62) Division of application No. 08/983,139, filed on Jan. 21, 1998, now Pat. No. 5,972,965.

(30) Foreign Application Priority Data

Jul. 21, 1995 (GB) .................................................. 9515085
Mar. 29, 1996 (AU) .................................................. PN9002

(51) Int. Cl.⁷ ........................ A61K 31/42; A61K 31/445; C07D 263/30; C07D 413/04
(52) U.S. Cl. .......................... 514/326; 514/374; 546/209; 548/235
(58) Field of Search .................................... 514/326, 374; 546/209; 548/235

(56) References Cited

U.S. PATENT DOCUMENTS 5,348,969  9/1994  Romine et al. .
5,763,489  6/1998  Taniguchi et al. .
5,863,918  1/1999  Taniguchi et al. .

FOREIGN PATENT DOCUMENTS 0434034  6/1991  (EP) .
9517393  6/1995  (WO) .

Primary Examiner—T. A. Solola
(74) Attorney, Agent, or Firm—Oblon, Spivak, McClelland, Maier & Neustadt, P.C.

(57) ABSTRACT

Heterocyclic compounds of the formula:

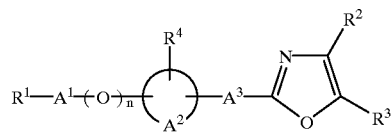

wherein
$R^1$ is carboxy or protected carboxy,
$R^2$ is aryl which may have suitable substituent(s),
$R^3$ is aryl which may have suitable substituent(s),
$R^4$ is hydrogen, lower alkyl, hydroxy or aryl,
$A^1$ is lower alkylene,

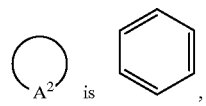

etc.,

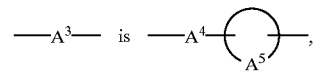

etc. and
n is 0 or 1,
and pharmaceutically acceptable salts thereof which are useful as a medicament.

17 Claims, No Drawings

HETEROCYCLIC COMPOUNDS

This application is a Div. of Ser. No. 08/983,139 filed Jan. 21, 1998 now U.S. Pat. No. 5,972,965.

TECHNICAL FIELD

This invention relates to new heterocyclic compounds and pharmaceutically acceptable salts thereof which are useful as a medicament.

BACKGROUND ART

Some heterocyclic compounds have been known as described, for example, in WO 95/17393.

DISCLOSURE OF INVENTION

This invention relates to new heterocyclic compounds. More particularly, this invention relates to new heterocyclic compounds and pharmaceutically acceptable salts thereof which have pharmacological activities such as an inhibitory activity on platelet aggregation, vasodilating activity, antihypertensive activity or the like and are prostaglandin $I_2$ agonists, to processes for their production, to a pharmaceutical composition containing the same and to a use thereof for manufacture of medicaments.

Accordingly, one object of this invention is to provide new and useful heterocyclic compounds and pharmaceutically acceptable salts thereof.

Another object of this invention is to provide processes for production of the heterocyclic compounds and salts thereof.

A further object of this invention is to provide a pharmaceutical composition containing, as an active ingredient, said heterocyclic compounds or pharmaceutically acceptable salts thereof.

Still further object of this invention is to provide use of the heterocyclic compounds and pharmaceutically acceptable salts thereof for manufacture of medicaments for the therapeutic and/or prophylactic treatment of arterial obstruction, cerebrovascular disease, hepatic cirrhosis, arteriosclerosis, ischemic heart disease, restenosis after percutaneous transluminal coronary angioplasty, hypertension or the like.

The heterocyclic compounds of this invention can be represented by the following formula (I):

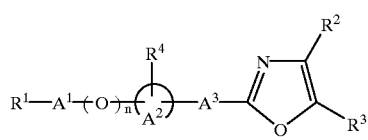

(I)

wherein
  $R^1$ is carboxy or protected carboxy,
  $R^2$ is aryl which may have suitable substituent(s),
  $R^3$ is aryl which may have suitable substituent(s),
  $R^4$ is hydrogen, lower alkyl, hydroxy or aryl,
  $A^1$ is lower alkylene,

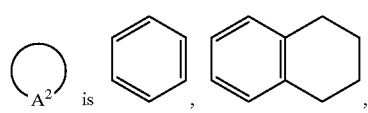

-continued

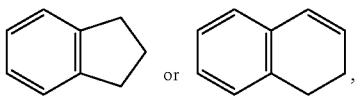

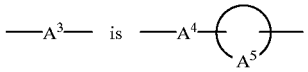

(in which —$A^4$— is bond, —$CH_2$— or —CO—, and

is cyclo-($C_5$-$C_8$)alkene, cyclo($C_7$-$C_8$)alkane, bicycloheptane, bicycloheptene, tetrahydrofuran, tetrahydrothiophene, azetidine, pyrrolidine or piperidine, each of which may have suitable substituent (s)) or —X—$A^6$— [in which —X— is —O—,

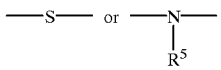

(in which $R^5$ is hydrogen, lower alkyl or acyl) and $A^6$ is lower alkylene which may have suitable substituent (s)], and
  n is 0 or 1.

According to the present invention, the new heterocyclic compounds (I) can be prepared by the processes which are illustrated in the following scheme.

Process 1

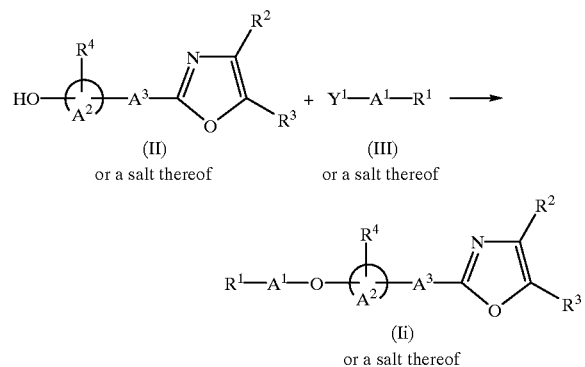

Process 2

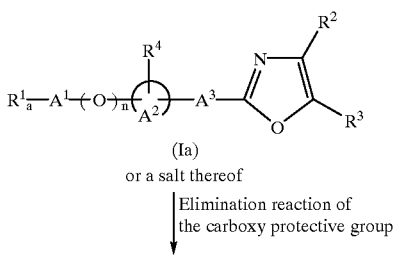

-continued

Process 5

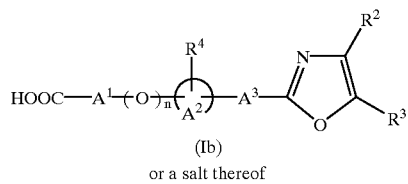
(Ib) or a salt thereof

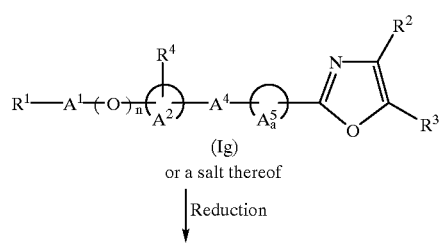
(Ig) or a salt thereof

Reduction

Process 3

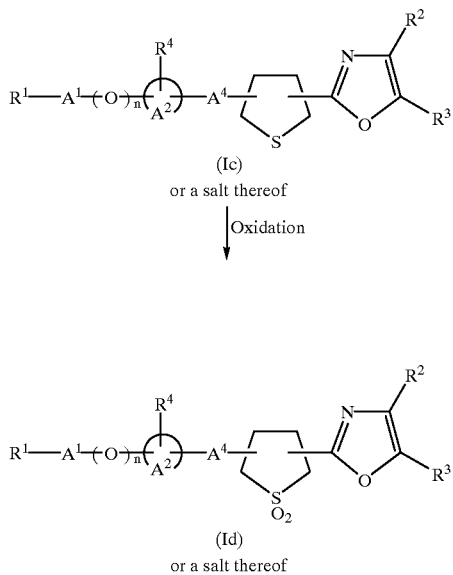
(Ic) or a salt thereof

Oxidation (Id) or a salt thereof

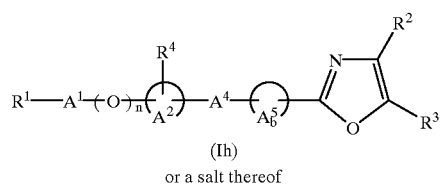
(Ih) or a salt thereof

Process 6

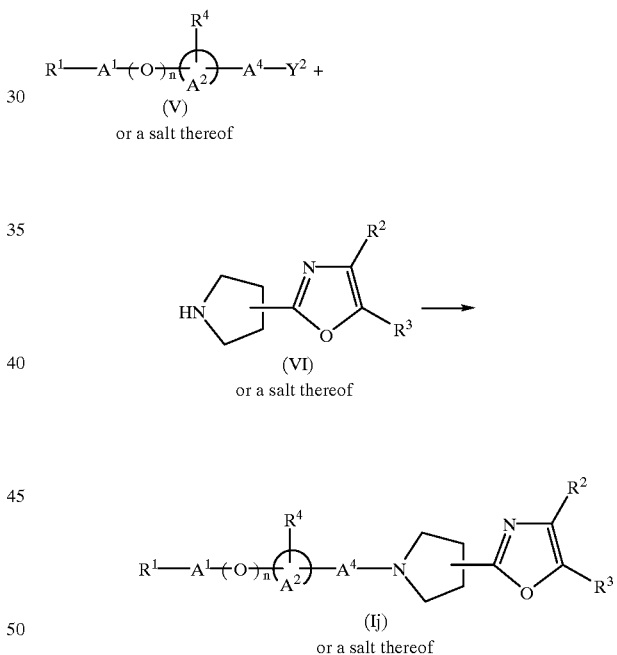
(V) or a salt thereof (VI) or a salt thereof (Ij) or a salt thereof

Process 4

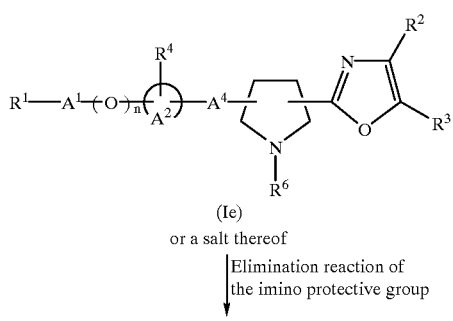
(Ie) or a salt thereof

Elimination reaction of the imino protective group

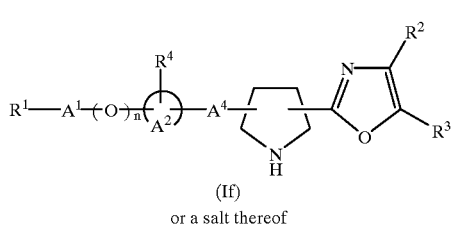
(If) or a salt thereof wherein
$R^1$, $R^2$, $R^3$, $R^4$, n, $A^1$,

—$A^3$— and —$A^4$— are each as defined above,
$Y^1$ is acid residue,
$R_a^1$ is protected carboxy,
$R^6$ is imino protective group,

is cyclo($C_7$–$C_8$)alkene, $\left(\underset{A_b^5}{\bigcirc}\right)$ is cyclo($C_7$–$C_8$)alkane, and $Y^2$ is halogen.

The starting compounds (II), (V) and (VI) are novel and can be prepared by the following process.

Process A

R⁷—O—(ring with $A^2$, $R^4$)—$A^3$—(oxazole with $R^2$, $R^3$)

(IV)
or a salt thereof

↓ Elimination reaction of the hydroxy protective group

HO—(ring with $A^2$, $R^4$)—$A^3$—(oxazole with $R^2$, $R^3$)

(II)
or a salt thereof

Process B $R^1$—$A^1$—(O)$_n$—(ring with $A^2$, $R^4$)—$A^4$—OH (VII)
or a salt thereof ↓ Halogenation $R^1$—$A^1$—(O)$_n$—(ring with $A^2$, $R^4$)—$A^4$—$Y^2$ (V)
or a salt thereof Process C $R^8$—N(pyrrolidine)—(oxazole with $R^2$, $R^3$)

(VIII)
or a salt thereof

↓ Elimination reaction of the acyl group

HN(pyrrolidine)—(oxazole with $R^2$, $R^3$)

(VI)
or a salt thereof wherein
$R^1$, $R^2$, $R^3$, $R^4$, n, $A^1$, $\left(\underset{A^2}{\bigcirc}\right)$ —$A^3$—, —$A^4$— and $Y^2$ are each as defined above,
$R^7$ is hydroxy protective group, and
$R^8$ is acyl.

Suitable pharmaceutically acceptable salts of the object compound (I) are conventional non-toxic salts and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, trifluoroacetate, etc.), an inorganic acid salt (e.g. hydrochloride, hydrobromide, sulfate, phosphate, etc.), a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

Suitable "aryl" and "aryl moiety" in the term "mono(or di or tri)aryl(lower)alkyl" may include phenyl, naphthyl and the like.

Suitable "lower alkylene" may include straight one having 1 to 6 carbon atom(s), such as methylene, ethylene, trimethylene, tetramethylene, pentamethylene and hexamethylene, preferably one having 1 to 3 carbon atom(s).

Suitable "lower alkyl" and "lower alkyl moiety" in the term "mono(or di or tri)aryl(lower)alkyl" may include straight or branched one having 1 to 6 carbon atom(s), such as methyl, ethyl, propyl, isopropyl, butyl, isobutyl, sec-butyl, t-butyl, pentyl, t-pentyl, hexyl or the like, preferably one having 1 to 4 carbon atom(s).

Suitable "protected carboxy" may include esterified carboxy and the like.

Suitable example of the ester moiety of an esterified carboxy may be the ones such as lower alkyl ester (e.g. methyl ester, ethyl ester, propyl ester, isopropyl ester, butyl ester, isobutyl ester, tert-butyl ester, pentyl ester, hexyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(or 2)-isobutyryloxyethyl ester, (1 or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1(or 2)-pentanoyloxyethyl ester, etc.], lower alkylsulfonyl(lower) alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower) alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), phthalidylidene (lower)alkyl ester, or (5-lower alkyl-2-oxo-1,3-dioxol-4-yl) (lower)alkyl ester [e.g. (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl) ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) such as mono(or di or tri)phenyl(lower) alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl) methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.); phthalidyl ester; and the like.

Suitable "substituent" in the term "aryl which may have suitable substituent(s)" may include halogen, amino, hydroxy, lower alkoxy, lower alkyl as exemplified above, and the like.

Suitable "halogen" may include chlorine, bromine, iodine and the like.

Suitable "lower alkoxy" may include methoxy, ethoxy propoxy, isopropoxy, butoxy, isobutoxy, t-butoxy, pentyloxy, t-pentyloxy, hexyloxy and the like.

Suitable "cyclo($C_5$–$C_8$)alkene" may include cyclopentene, cyclohexene, cycloheptene and cyclooctene.

Suitable "cyclo($C_7$–$C_8$)alkene" may include cycloheptene and cyclooctene.

Suitable "cyclo($C_7$–$C_8$)alkane" may include cycloheptane and cyclooctane.

Suitable "bicycloheptane" may include bicyclo[2.2.1] heptane and the like.

Suitable "bicycloheptene" may include bicyclo[2.2.1] heptene (e.g., bicyclo[2.2.1]hept-2-en, etc.) and the like.

Suitable "substituent" in the term "cyclo($C_5$–$C_8$)alkene, cyclo($C_7$–$C_8$)alkane, bicycloheptane, bicycloheptene, tetrahydrofuran, tetrahydrothiophene, azetidine, pyrrolidine or piperidine, each of which may have suitable substituent (s)" may include imino, hydroxy, oxo, acyl, imino protective group, and the like.

Suitable "acyl" may include lower alkanoyl (e.g. formyl, acetyl, propionyl, butyryl, isobutyryl, valeryl, isovaleryl, oxalyl, succinyl, pivaloyl, etc.); lower alkoxycarbonyl (e.g. methoxycarbonyl, ethoxycarbonyl, propoxycarbonyl, isopropoxycarbonyl, butoxycarbonyl, tert-butoxycarbonyl, pentyloxycarbonyl, hexyloxycarbonyl, etc.); lower alkanesulfonyl (e.g. mesyl, ethanesulfonyl, propanesulfonyl, isopropanesulfonyl, butanesulfonyl, etc.); arenesulfonyl (e.g. benzenesulfonyl, tosyl, etc.); aroyl (e.g. benzoyl, toluoyl, xyloyl, naphthoyl, phthaloyl, indancarbonyl, etc.); ar(lower)alkanoyl (e.g. phenylacetyl, phenylpropionyl, etc.); ar(lower)alkoxycarbonyl (e.g. benzyloxycarbonyl, phenethyloxycarbonyl, etc.), and the like.

Suitable "imino protective group" may include mono(or di or tri)aryl(lower)alkyl and the like.

Suitable "hydroxy protective group" may include lower alkyl as exemplified above, silyl which may have one to three suitable substituent(s), and the like.

Suitable "substituent" in the term "silyl which may have one to three suitable substituent(s)" may include lower alkyl as exemplified above, aryl as exemplified above, and the like.

Suitable "substituent" in the term "lower alkylene which may have suitable substituent(s)" may include lower alkyl as exemplified above, hydroxy(lower)alkyl (e.g. hydroxymethyl, hydroxyethyl, hydroxypropyl, hydroxybutyl, hydroxypentyl, hydroxyhexyl, etc.) and the like.

Suitable "acid residue" may include halogen as exemplified above, lower alkanoyloxy (e.g. acetyloxy, etc.); sulfonyloxy (e.g. methylsulfonyloxy, phenylsulfonyloxy, tolylsulfonyloxy, etc.), and the like.

Preferred embodiments of the object compound (I) are as follows:

$R^1$ is carboxy or protected carboxy (more preferably esterified carboxy, most preferably lower alkoxycarbonyl), $R^2$ is aryl which may have lower alkyl (more preferably phenyl or lower alkylphenyl, most preferably phenyl or $C_1$–$C_4$ alkylphenyl), $R^3$ is aryl which may have lower alkyl (more preferably phenyl or lower alkylphenyl, most preferably phenyl or $C_1$–$C_4$ alkylphenyl), $R^4$ is hydrogen, lower alkyl (more preferably $C_1$–$C_4$ alkyl, most preferably methyl), hydroxy or aryl (more preferably phenyl), $A^1$ is lower alkylene (more preferably $C_1$–$C_4$ alkylene, most preferably methylene or ethylene),

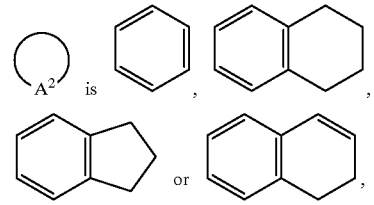

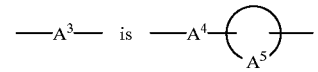

[in which —$A^4$— is bond, —$CH_2$— or —CO—, and

is cyclo($C_5$–$C_8$)alkene, cyclo($C_7$–$C_8$)alkane, bicycloheptane (more preferably bicyclo[2.2.1]heptane), bicycloheptene (more preferably bicyclo[2.2.1]heptene, most preferably bicyclo[2.2.1]hept-2-ene), tetrahydrofuran, tetrahydrothiophene, azetidine, pyrrolidine or piperidine, each of which may have one to three (more preferably one or two) suitable substituent (s) selected from the group consisting of imino, oxo, acyl (more preferably lower alkanoyl, most preferably $C_1$–$C_4$ alkanoyl) and imino protective group (more preferably mono(or di or tri)phenyl(lower)alkyl, most preferably phenyl(lower)alkyl)] or —X—$A^6$— [in which —X— is —O—, —S— or

(in which $R^5$ is hydrogen, lower alkyl (more preferably $C_1$–$C_4$ alkyl) or acyl (more preferably lower alkanoyl, most preferably $C_1$–$C_4$ alkanoyl) and $A^6$ is lower alkylene (more preferably $C_1$–$C_4$ alkylene, most preferably methylene or ethylene) which may have one to three (more preferably one) suitable substituent(s) selected from the group consisting of lower alkyl (more preferably $C_1$–$C_4$ alkyl) and hydroxy (lower)alkyl (more preferably hydroxy($C_1$–$C_4$)alkyl)], and n is 0 or 1.

More preferred compounds of the object compound (I) are the compounds of the following formulae (I-A) and (I-B):

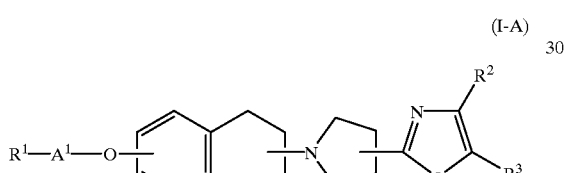
(I-A)

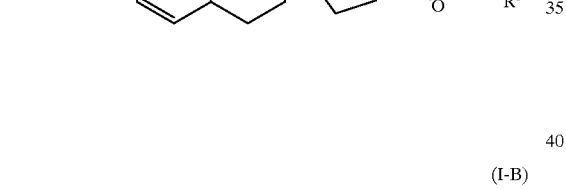
(I-B)

wherein $R^1$ is carboxy, or protected carboxy (more preferably esterified carboxy, most preferably lower alkoxycarbonyl), $R^2$ is phenyl, or lower alkylphenyl (more preferably $C_1$–$C_4$ alkylphenyl), $R^3$ is phenyl, or lower alkylphenyl (more preferably $C_1$–$C_4$ alkylphenyl) and $A^1$ is lower alkylene (more preferably $C_1$–$C_4$ alkylene, most preferably methylene).

Most preferred compounds of the object compound (I) are the compounds of the following formulae (I-C) and (I-D):

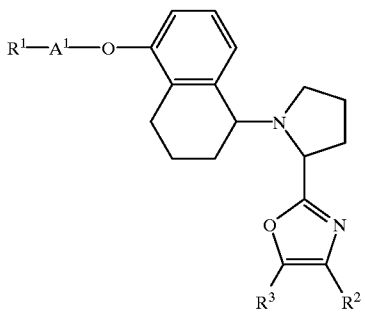
(I-C)

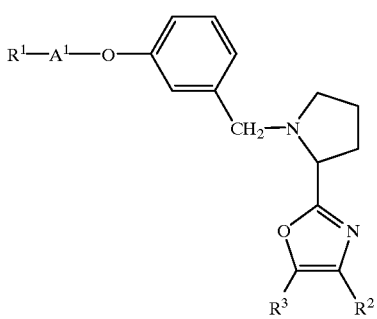
(I-D)

wherein $R^1$ is carboxy, or protected carboxy (more preferably esterified carboxy, most preferably lower alkoxycarbonyl), $R^2$ is phenyl, $R^3$ is phenyl, and $A^1$ is lower alkylene (more preferably $C_1$–$C_4$ alkylene, most preferably methylene).

It is to be noted the object compound (I) may include one or more stereoisomers due to asymmetric carbon atom(s) and double bond, and all of such isomers and a mixture thereof are included within the scope of the present invention.

It is further to be noted isomerization or rearrangement of the object compound (I) may occur due to the effect of the light, acid, base or the like, and the compound obtained as the result of said isomerization or rearrangement is also included within the scope of the present invention.

It is also to be noted that the solvating form of the compound (I) (e.g. hydrate, etc.) and any form of the crystal of the compound (I) are included within the scope of the present invention.

The processes for preparing the object and starting compounds of the present invention are explained in detail in the following.

Process 1

The compound (Ii) or a salt thereof can be prepared by reacting the compound (II) or a salt thereof with the compound (III) or a salt thereof.

This reaction is usually carried out in a solvent such as acetonitrile, benzene, N,N-dimethylformamide, tetrahydrofuran, methylene chloride, ethylene chloride, chloroform, diethyl ether or any other solvent which does not adversely affect the reaction.

The reaction temperature is not critical and the reaction is usually carried out under cooling to warming.

The reaction is usually carried out in the presence of a base.

Suitable base may include the inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.) or the like, and the organic base such as tri(lower)alkylamino (e.g., trimethylamine, triethylamine, diisopropylethylamine, etc.), di(lower)alkylaniline (e.g. dimethylaniline, etc.), pyridine or the like.

Process 2

The compound (Ib) or a salt thereof can be prepared by subjecting the compound (Ia) or a salt thereof to elimination reaction of the carboxy protective group.

Suitable method of this reaction may include conventional one such as hydrolysis, reduction and the like.

(i) For Hydrolysis

The hydrolysis is preferably carried out in the presence of a base or an acid including Lewis acid.

Suitable base may include an inorganic base and an organic base such as an alkali metal [e.g. sodium, potassium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, 1,2-dimethoxyethane, a mixture thereof or any other solvent which does not adversely influence the reaction. A liquid base or acid can be also used as the solvent. The reaction temperature is not critical and the reaction is usually carried out under cooling to warming.

(ii) For Reduction

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like. The reduction is usually carried out in a conventional solvent which does not adversely influence the reaction such as water, methanol, ethanol, propanol, ethyl acetate, N,N-dimethylformamide, tetrahydrofuran, or a mixture thereof. Additionally, in case that the above-mentioned acids to be used in chemical reduction are in liquid, they can also be used as a solvent.

The reaction temperature of this reduction is not critical and the reaction is usually carried out under cooling to warming.

Process 3

The compound (Id) or a salt thereof can be prepared by subjecting the compound (Ic) or a salt thereof to oxidation reaction.

Oxidation is carried out in a conventional manner and suitable oxidizing reagent may include per acid (e.g., perbenzoic acid, m-chloroperbenzoic acid, performic acid, peracetic acid, perphthalic acid, etc.), and the like.

The reaction is usually carried out in a conventional solvent such as water, alcohol (e.g., methanol, ethanol, isopropyl alcohol, etc.), tetrahydrofuran, dioxane, dichloromethane, ethylene dichloride, chloroform, N,N-dimethylformamide, N,N-dimethylacetamide, or any other organic solvent which does not adversely affect the reaction.

The reaction temperature is not critical and the reaction is usually carried out under cooling to heating.

Process 4

The compound (If) or a salt thereof can be prepared by subjecting the compound (Ie) or a salt thereof to elimination reaction of the imino protective group.

This reaction can be carried out in a similar manner to that of the aforementioned Process 2, and therefore the reagents to be used and the reaction conditions (e.g., solvent, reaction temperature, etc.) can be referred to those of the Process 2.

Process 5

The compound (Ih) or a salt thereof can be prepared by subjecting the compound (Ig) or a salt thereof to reduction reaction.

This reduction can be carried out in a similar manner to that of the aforementioned Process 2, and therefore the reagents to be used and the reaction conditions (e.g., solvent, reaction temperature, etc.) can be referred to those of the Process 2.

Process 6

The compound (Ij) or a salt thereof can be prepared by reacting the compound (V) or a salt thereof with the compound (VI) or a salt thereof.

This reaction can be carried out in a similar manner to that of the aforementioned Process 1, and therefore the reagents to be used and the reaction conditions (e.g., solvent, reaction temperature, etc.) can be referred to those of the Process 1.

Process A

The compound (II) or a salt thereof can be prepared by subjecting the compound (IV) or a salt thereof to elimination reaction of the hydroxy protective group.

The reagent to be used in this reaction may include halotrialkylsilane (e.g., iodotrimethylsilane, etc.), alkali metal thioalkoxide (e.g., sodium thioethoxide, etc.), alkali metal sulfide (e.g., sodium sulfide, etc.), alkali metal diphenylphosphide (e.g., lithium diphenylphosphide, etc.), aluminum halide (e.g., aluminum chloride, aluminum bromide, etc.), boron trihalide (e.g., boron trichloride, boron tribromide, etc.), pyridine hydrochloride, alkylmagnesium halide (e.g., methylmagnesium iodide, etc.), lithium halide (e.g., lithium chloride, etc.), tetraalkylammonium halide (e.g., tetrabutylammonium fluoride, etc.), a combination of methionine and sulfonic acid (e.g., methanesulfonic acid, etc.), and the like.

The reaction is usually carried out in a conventional solvent such as water, alcohol, (e.g., methanol, ethanol, isopropyl alcohol, etc.), tetrahydrofuran, dioxane, dichloromethane, ethylene dichloride, chloroform, N,N-dimethylformamide, N,N-dimethylacetamide, or any other organic solvent which does not adversely affect the reaction.

The reaction temperature is not critical and the reaction is usually carried out under cooling to heating.

The compound (IV) or a salt thereof can be prepared by the methods disclosed in the Preparations described later or similar manners thereto.

Process B

The compound (V) or a salt thereof can be prepared by subjecting the compound (VII) or a salt thereof to halogenation reaction.

This reaction can be carried out by the method disclosed in the Preparation 21 or similar manners thereto.

The compound (VII) or a salt thereof can be prepared by the methods disclosed in the Preparations described later or similar manners thereto.

Process C

The compound (VI) or a salt thereof can be prepared by subjecting the compound (VIII) or a salt thereof to elimination reaction of the acyl group.

This reaction can be carried out in a similar manner to that of the aforementioned Process 2, and therefore the reagents to be used and the reaction conditions (e.g., solvent, reaction temperature, etc.) can be referred to those of the Process 2.

The compound (VIII) or a salt thereof can be prepared by the methods disclosed in the Preparations described later or similar manners thereto.

The object compound (I) of this invention and pharmaceutically acceptable salt thereof have pharmacological activities such as an inhibitory activity on platelet aggregation, vasodilating activity, antihypertensive activity or the like and are prostaglandin $I_2$ agonists, and therefore can be used for treating and/or preventing thrombosis, arterial obstruction (e.g., chronic arterial obstruction, etc.), cerebrovascular disease, gastric ulcer, hepatitis, hepatic insufficiency, hepatic cirrhosis, arteriosclerosis, ischemic heart disease, restenosis or ischemic complications after coronary angioplasty (e.g., PTCA, coronary stenting, etc.), hypertension, inflammation, autoimmune disease, heart failure, renal disease (e.g., renal failure, nephritis, etc.), diabetic complication (e.g., diabetic neuropathy, diabetic nephropathy, diabetic retinopathy, etc.), peripheral circulatory disturbance, baldness, bedsore, and the like, and can be also used for protecting organs after transplantation or surgery.

Further, the object compound (I) and pharmaceutically acceptable salt thereof can be also used as a component for organ preserving fluids and as an agent for inhibiting metastasis of cancer.

In order to show the utility of the object compound (I), pharmacological data of the representative compounds thereof are shown in the following.

Inhibition of human platelet aggregation induced by ADP

[I] Test Compound (1) Sodium [3-[[2-(4,5-diphenyloxazol-2-yl)-2-cyclohepten-1-yl]methyl]phenoxy]acetate (2) Sodium salt of (1R)-1-((2R)-2-(4,5-diphenyloxazol-2-yl)pyrrolidin-1-yl]-5-carboxymethoxy-1,2,3,4-tetrahydronaphthalene

[II] Test Method

Human blood was obtained from healthy volunteers and mixed with ⅒ volume of 3.8% sodium citrate, pH 7.4. The citrate blood was centrifuged at 150 ×g for 10 minutes and the platelet rich plasma (PRP) was removed. The remaining blood was centrifuged for a further 10 minutes at 1500 ×g to prepare the platelet poor plasma (PPP), which was used as a reference for platelet aggregation. Aggregation studies were carried out using HEMATRACER 801 (NBS, Japan), a 8 channel aggregometer. 25 μl of sample solution and 225 μl of PRP were mixed and stirred at 1000 rpm for 2 minutes at 37° C. Aggregation was induced by ADP solution at the final concentration of 2.5 μM.

| [III] Test result: | |
| --- | --- |
| Test Compound | Inhibition (%) |
| (1) $1.0 \times 10^{-7}$M | 88 ± 0.5 |
| (2) $1.0 \times 10^{-7}$M | 85 ± 7.6 | mean ± S.E.

The pharmaceutical composition of the present invention can be used in the form of a pharmaceutical preparation, for example, in solid, semisolid or liquid form (e.g. tablet, pellet, troche, capsule, suppository, cream, ointment, aerosol, powder, solution, emulsion, suspension etc.), which contains the object compound (I) or a pharmaceutically acceptable salt thereof as an active ingredient, suitable for rectal, pulmonary (nasal or buccal inhalation), nasal, ocular, external (topical), oral or parenteral (including subcutaneous, intravenous and intramuscular) administrations or insufflation.

The pharmaceutical composition of this invention can contain various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (e.g. cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropylstarch, sodium glycol-starch, sodium bicarbonate, calcium phosphate, calcium citrate, etc.), lubricant (e.g. magnesium stearate, talc, sodium laurylsulfate, etc.), flavoring agent (e.g. citric acid, mentol, glycine, orange powders, etc.), preservative (e.g. sodium benzoate, sodium bisulfite, methylparaben, propylparaben, etc.), stabilizer (e.g. citric acid, sodium citrate, acetic acid, etc.), suspending agent (e.g. methyl cellulose, polyvinylpyrrolidone, aluminum stearate, etc.), dispersing agent, aqueous diluting agent (e.g. water), base wax (e.g. cacao butter, polyethyleneglycol, white petrolatum, etc.).

The effective ingredient may usually be administered with a unit dose of 0.01 mg/kg to 50 mg/kg, 1 to 4 times a day. However, the above dosage may be increased or decreased according to age, weight, conditions of the patient or the administering method.

The following Preparations and Examples are given only for the purpose of illustrating the present invention in more detail.

Preparation 1

(1) To a solution of y-butyrolactone (3.0 g) in tetrahydrofuran (THF) (30 ml) was added lithium diisopropylamide (LDA) (28 ml, 1.5 M solution in cyclohexane) at −78° C. under $N_2$, and then after 30 minutes, a solution of m-anisaldehyde (4.7 g) in THF (10 ml) was added in the solution. After being stirred for 2 hours at the same temperature, the solution was poured into the mixture of ethyl acetate and water. The organic layer was washed with 1N-HCl solution, sat. NaHCO$_3$ and brine, dried over MgSO$_4$, and evaporated in vacuo. The residue was purified by chromatography on silica gel to afford 3-[hydroxy (3-methoxyphenyl)methyl]-2-oxotetrahydrofuran (7.4 g).

MS (m/z): 205 (M$^+$−17)

IR (Neat) 3400, 1725 cm$^{-1}$

NMR (CDCl$_3$, δ): 2.2–2.8 (4H, m), 3.81 (3H, s), 4.1–4.4 (2H, m), 4.80 (1H, d, J=8.0 Hz), 6.8–7.1 (3H, m), 7.27 (1H, t, J=8.0 Hz)

(2) A mixture of 3-[hydroxy(3-methoxyphenyl)methyl]-2-oxotetrahydrofuran (1.0 g) and 10% Pd/C (0.5 g) in ethanol (20 ml) was stirred under H$_2$ for 10 hours. The catalyst was filtered off and the filtrate was evaporated in vacuo to give 3-(3-methoxybenzyl)-2-oxotetrahydrofuran (0.8 g).

MS (m/z): 207 (M$^+$+1)

IR (Neat): 1750 cm$^{-1}$

NMR (CDCl$_3$, δ): 2.0–2.6 (4H, m), 2.7–3.2 (3H, m), 3.79 (3H, s), 4.1–4.4 (2H, m), 6.7–7.1 (3H, m), 7.2–7.4 (1H, m)

(3) To a solution of 3-(3-methoxybenzyl)-2-oxotetrahydrofuran (4.7 g) in dichloromethane (60 ml) was added BBr$_3$ (46 ml, 1M solution in dichloromethane) at 0° C. After being stirred for 2 hours, the solvent was evaporated in vacuo. The residue was diluted with ethyl acetate, and the mixture was washed with water and brine. The dried solvent was evaporated and the residue was dissolved in N,N-dimethylformamide (DMF) (30 ml). To the solution were added imidazole (3.1 g) and t-butyldiphenylsilyl chloride (8.9 g) and stirred for 2 hours at room temperature. The solution was poured into the mixture of ethyl acetate and water. The organic layer was washed with water and brine, dried over MgSO$_4$, and evaporated in vacuo. The residue was purified by chromatography on silica gel to afford 3-(3-t-butyldiphenylsilyloxybenzyl)-2-oxotetrahydrofuran (8.6 g).

MS (m/z): 429 (M+−1)

IR (Neat): 1760 cm$^{-1}$

NMR (CDCl$_3$, δ): 1.05 (9H, s), 1.4–2.0 (2H, m), 2.3–2.6 (2H, m), 3.01–3.06 (1H, m), 3.8–4.2 (2H, m), 6.47 (1H, m), 6.6–6.8 (2H, m), 7.05 (1H, t, J=8 Hz), 7.2–7.5 (6H, m), 7.6–7.8 (4H, m)

(4) To a solution of 4,5-diphenyloxazole (5.3 g) in THF (50 ml) at −78° C. under N$_2$ was added n-butyllithium (1.6 M in hexane, 9.2 ml). After 30 minutes, a solution of 3-(3-t-butyldiphenylsilyloxybenzyl)-2-oxotetrahydrofuran (3.3 g) in THF (30 ml) was added thereto and stirred for 1 hour at the same temperature. The reaction mixture was poured into the mixture of ethyl acetate and water. The organic layer was washed with 1N-HCl solution, sat. NaHCO$_3$ and brine, dried over MgSO$_4$, and evaporated in vacuo. The oily residue was dissolved in THF (100 ml) and LiAlH$_4$ was added to the solution at 0° C. After being stirred for 2 hours, the mixture was poured into a mixture of ethyl acetate and 1N-HCl solution. The organic layer was washed with sat. NaHCO$_3$ and brine, dried over MgSO$_4$, and evaporated in vacuo. The residue was purified by chromatography on silica gel to afford 3-[3-(4,5-diphenyloxazol-2-yl)-3-hydroxy-2-(2-hydroxyethyl)propyl]-1-(t-butyldiphenylsilyloxy)benzene (4.3 g).

MS (m/z): 654 (M++1)

IR (Neat): 3400 cm$^{-1}$

NMR (CDCl$_3$, δ): 1.09 (9H, s), 1.4–1.8 (2H, m), 2.2–2.7 (3H, m), 3.3–3.8 (2H, m), 4.6–4.8 (1H, m), 6.5–6.8 (3H, m), 6.99 (1H, t, J=8 Hz), 7.2–7.8 (20H, m)

(5) A mixture of 3-[3-(4,5-diphenyloxazol-2-yl)-3-hydroxy-2-(2-hydroxyethyl)propyl]-1-(t-butyldiphenylsilyloxy) benzene (1.3 g) and p-toluenesulfonic acid (100 mg) in toluene (20 ml) was stirred under reflux for 6 hours. The solution was washed with sat. NaHCO$_3$ and brine, dried over MgSO$_4$, and evaporated in vacuo to afford crude 2-(4,5-diphenyloxazol-2-yl)-3-(3-t-butyldiphenylsilyloxybenzyl)tetrahydrofuran (1.5 g).

Preparation 2

A mixture of 3-[3-(4,5-diphenyloxazol-2-yl)-3-hydroxy-2-(2-hydroxyethyl)propyl]-1-(t-butyldiphenylsilyloxy) benzene (3.0 g) and methanesulfonyl chloride (1.1 ml) and triethylamine (2.6 ml) in THF (50 ml) was stirred at room temperature for 1 hour. The solution was diluted with ethyl acetate and washed with sat. NaHCO$_3$ and brine, dried over MgSO$_4$, and evaporated. The residue was dissolved in DMF (40 ml) and to the solution was added Na$_2$S (600 mg). After being stirred for 30 minutes at 80° C., the mixture was partitioned between ethyl acetate and water. The organic layer was washed with water, sat. NaHCO$_3$, and brine. The dried solvent was evaporated in vacuo and the residue was purified by chromatography on silica gel to afford 2-(4,5-diphenyloxazol-2-yl)-3-(3-t-butyldiphenylsilyloxybenzyl) tetrahydrothiophene (3.2 g).

MS (m/z): 652 (M$^+$+1)

IR (Neat): 1600, 1580 cm$^{-1}$

NMR (CDCl$_3$, δ): 1.08 (9H, s), 2.0–2.5 (4H, m), 2.6–3.2 (3H, m), 4.10 (2/3H, d, J=7 Hz), 4.20 (1/3H, d, J=7 Hz), 6.4–6.8 (3H, m), 6.9–7.1 (1H, m), 7.2–7.8 (20H, m)

Preparation 3

(1) 3-[3-(4,5-Diphenyloxazol-2-yl)-3-hydroxy-2-(2-hydroxyethyl)propyl]-1-methyloxybenzene was obtained according to a similar manner to that of Preparation 1 (4).

MS (m/z): 430 (M$^+$+1)

IR (Neat): 3400 cm$^{-1}$

NMR (CDCl$_3$, δ): 1.8–2.0 (2H, m), 2.5–3.0 (3H, m), 3.71 (3H, s), 3.6–4.0 (2H, m), 4.95 (1H, d, J=2 Hz), 6.6–6.9 (3H, m), 7.15 (1H, t, J=8 Hz), 7.2–7.8 (10H, m)

(2) A mixture of 3-[3-(4,5-diphenyloxazol-2-yl)-3-hydroxy-2-(2-hydroxyethyl)propyl]-1-methoxybenzene (3.3 g) and methanesulfonyl chloride (1.8 ml) and triethylamine (4.3 ml) in THF (50 ml) was stirred at room temperature for 1 hour. The solution was diluted with ethyl acetate and washed with sat. NaHCO$_3$ and brine, dried over MgSO$_4$, and evaporated. The residue was dissolved in benzylamine (10 ml). After being stirred for 2 hours at 80° C., the mixture was partitioned between ether and water. The organic layer was washed with water and brine. The dried solvent was evaporated in vacuo and the residue was purified by chromatography on silica gel to afford 1-benzyl-2-(4,5-diphenyloxazol-2-yl)-3-(3-methoxybenzyl)pyrrolidine (1.5 g).

MS (m/z): 501 (M$^+$+1)

IR (Neat): 1600 cm$^{-1}$

NMR (CDCl$_3$, δ): 2.0–3.2 (7H, m), 3.60 (3H, s), 3.5–4.0 (3H, m), 6.5–6.8 (3H, m), 7.0–7.8 (16H, m)

Preparation 4

(1) 2-(α-Hydroxy-3-methoxybenzyl)cycloheptanone was obtained according to a similar manner to that of Preparation 1 (1).

MS (m/z): 231 (M$^+$−17)

IR (Neat): 3400, 1690 cm$^{-1}$

NMR (CDCl$_3$, δ): 1.0–2.0 (8H, m), 2.3–2.7 (2H, m), 2.8 (1H, m), 3.20 (1H, d, J=2 Hz), 3.78 (3H, s), 5.15 (1H, t, J=2 Hz), 6.7–7.0 (3H, m), 7.26 (1H, t, J=8 Hz)

(2) 2-(3-Methoxybenzyl)cycloheptanone was obtained according to a similar manner to that of Preparation 1 (2).

IR (Neat): 1700 cm$^{-1}$
NMR (CDCl$_3$, δ): 1.2–2.0 (8H, m), 2.4–2.6 (3H, m), 2.8 (1H, m), 3.05 (1H, dd, J=5.8, 13.5 Hz), 3.77 (3H, s), 6.5–6.9 (3H, m), 7.21 (1H, t, J=8 Hz)

(3) 1-Hydroxy-1-(4,5-diphenyloxazol-2-yl)-2-(3-methoxybenzyl)cycloheptane was obtained by reacting 2-(3-methoxybenzyl)cycloheptanone according to a similar manner to that of Preparation 1 (4).
MS (m/z): 454 (M$^+$+1)
IR (Neat): 3400 cm$^{-1}$
NMR (CDCl$_3$, δ): 1.2–2.6 (11H, m), 3.20 (1H, br s), 3.64 (3H, s), 6.5–6.8 (3H, m), 7.10 (1H, t, J=8 Hz), 7.3–7.8 (10H, m)

(4) A mixture of 1-hydroxy-1-(4,5-diphenyloxazol-2-yl)-2-(3-methoxybenzyl)cycloheptane (5.2 g) and p-toluenesulfonic acid (500 mg) in toluene (50 ml) was stirred under reflux for 4 hours. The solution was washed with water, sat. NaHCO$_3$ and brine, dried over MgSO4, and evaporated in vacuo. The residue was purified by chromatography on silica gel to afford 1-(4,5-diphenyloxazol-2-yl)-7-(3-methoxybenzyl)-1-cycloheptene (4.7 g).
MS (m/z): 436 (M$^+$+1)
IR (Neat): 1600 cm$^{-1}$
NMR (CDCl$_3$, δ): 1.3–2.0 (6H, m), 2.4 (2H, m), 2.83 (1H, dd, J=10.0, 14 Hz), 3.00 (1H, dd, J=6.0, 14.0 Hz), 3.78 (3H, s), 6.7–7.0 (3H, m), 7.20 (1H, t, J=8 Hz), 7.2–7.8 (11H, m)

Preparation 5
(1) A mixture of 1-azido-5-methoxy-1,2,3,4-tetrahydronaphthalene (1.0 g) and 10% Pd/C (0.5 g) in methanol (20 ml) was stirred under H$_2$ for 10 hours. The catalyst was filtered off and filtrate was evaporated. The residue was dissolved in toluene (30 ml) and 4-hydroxy-1-(4,5-diphenyloxazol-2-yl)butan-1-one (1.3 g) and p-toluenesulfonic acid (200 mg) were added to the solution. After the mixture was heated under reflux in Dean-Stark apparatus for 4 hours, the solvent was removed in vacuo. The residue was dissolved in methanol (20 ml) and NaBH$_4$ (0.4 g) was added. After being stirred for 4 hours, the solution was poured into the mixture of ethyl acetate and water. The organic layer was washed with water and brine, dried over MgSO$_4$, and evaporated in vacuo. The residue was purified by chromatography on silica gel to afford 1-[[4-hydroxy-1-(4,5-diphenyloxazol-2-yl)butyl]amino]-5-methoxy-1,2,3,4-tetrahydronaphthalene (0.9 g).
MS (m/z): 469 (M$^+$+1)
IR (Neat): 3400 cm$^{-1}$
NMR (CDCl$_3$, δ): 1.6–2.8 (10H, m), 3.4–3.6 (2H, m), 3.79 (3H, s), 3.7–3.9 (1H, m), 4.0–4.2 (1H, m), 6.6–6.8 (1H, m), 6.9–7.2 (2H, m), 7.3–7.7 (10H, m)

(2) To a solution of 1-[[4-hydroxy-1-(4,5-diphenyloxazol-2-yl)butyl]amino]-5-methoxy-1,2,3,4-tetrahydronaphthalene (0.9 g) in CH$_2$Cl$_2$ (20 ml) was added SOCl$_2$ (3 ml). After being stirred for 4 hours, the solvent was removed. The residue was dissolved in CH$_3$CN (20 ml) and K$_2$CO$_3$ (5 g) was added to the solution. After being stirred for 4 hours under reflux, the solution was poured into the mixture of ethyl acetate and water. The organic layer was washed with water and brine, dried over MgSO$_4$, and evaporated in vacuo. The residue was purified by chromatography on silica gel to afford 1-[2-(4,5-diphenyloxazol-2-yl)pyrrolidin-1-yl]-5-methoxy-1,2,3,4-tetrahydronaphthalene (0.57 g).
MS (m/z): 451 (M$^+$+1)
IR (Neat): 1580 cm$^1$
NMR (CDCl$_3$, δ): 1.5–2.3 (8H, m), 2.4–3.2 (4H, m), 3.69 and 3.76 (3H, each s), 4.0–4.2 (2H, m), 6.4–6.72 (3H, m), 7.3–7.7 (10H, m)

Preparation 6
(1) To a solution of 5-t-butyldiphenylsilyloxy-1-tetralone (2.9 g) and (R)-5,5-diphenyl-2-methyl-3,4-propano-1,3,2-oxazaborolidine (2.3 g) in THF (5 ml) was added borane tetrahydrofuran complex (7.1 ml, 1M solution in THF) at −18° C. After being stirred for 30 minutes, the reaction was quenched with 1N HCl solution. The mixture was poured into a mixture of ethyl acetate and water. The organic layer was washed with 1N-HCl solution, sat. NaHCO$_3$ and brine, dried over MgSO$_4$, and evaporated in vacuo. The residue was purified by chromatography on silica gel to afford (1S)-1-hydroxy-5-t-butyldiphenylsilyloxy-1,2,3,4-tetrahydronaphthalene (3.2 g).
MS (m/z): 401 (M$^{+-}$1)
NMR (CDCl$_3$, δ): 1.10 (9H, s), 1.8–2.2 (4H, m), 2.6–3.1 (2H, m), 4.79 (1H, t, J=4.8 Hz), 6.30 (1H, d, J=8 Hz), 6.77 (1H, t, J=8 Hz), 6.97 (1H, d, J=8 Hz), 7.3–7.9 (10H, m)
HPLC; chiralcel AD, 2% isopropanol/hexane, 20.3 ml/min (2) A mixture of (1S)-1-hydroxy-5-t-butyldiphenylsilyloxy-1,2,3,4-tetrahydronaphthalene (1.0 g) and diphenyl phosphorazidate (0.65 ml) was dissolved in toluene (10 ml). The mixture was cooled to 0° C. under N$_2$, and neat 1,8-diazabicyclo[5.4.0]-7-undecene (DBU) (0.45 ml) was added. The reaction mixture was stirred for 2 hours at 0° C. then at 20° C. for 16 hours. The resulting mixture was washed with water and 1N-HCl. The organic layer was concentrated in vacuo and purified by silica gel chromatography to give (1R)-1-azido-5-t-butyldiphenylsilyloxy-1,2,3,4-tetrahydronaphthalene (950 mg).
MS (m/z): 400 (M$^+$+1)
IR (Neat): 2100 cm$^{-1}$
NMR (CDCl$_3$, δ): 1.10 (9H, s), 1.8–2.2 (4H, m), 2.6–3.1 (2H, m), 4.5–4.7 (1H, m), 6.3–6.4 (1H, m), 6.7–7.0 (2H, m), 7.1–7.8 (10H, m)

(3) A mixture of (1R)-1-azido-5-t-butyldiphenylsilyloxy-1,2,3,4-tetrahydronaphthalene (0.95 mg) and 10% Pd/C (0.2 g) in a mixture of ethanol (20 ml) and THF (20 ml) was stirred under H$_2$ for 2 hours. The catalyst was filtered off and filtrate was evaporated. The residue was dissolved in DMF (10 ml) and then K$_2$CO$_3$ (600 mg) and (4,5-diphenyloxazol-2-yl)methyl bromide (700 mg) were added thereto. After being stirred for 2 hours at room temperature, the mixture was poured into a mixture of ethyl acetate and water. The organic layer was washed with water and brine, dried over MgSO$_4$, and evaporated in vacuo. The residue was purified by chromatography on silica gel to afford (1R)-1-(4,5-diphenyloxazol-2-yl)methylamino-5-t-butyldiphenylsilyloxy-1,2,3,4-tetrahydronaphthalene (1.4 g).
MS (m/z): 636 (M$^+$+1)
IR (Neat): 3400 cm$^{-1}$
NMR (CDCl$_3$, δ): 1.09 (9H, s), 1.6–2.2 (4H, m), 2.6–3.2 (2H, m), 3.91 (1H, m), 4.06 (2H, s), 6.30 (1H, d, J=8 Hz), 6.72 (1H, t, J=8 Hz), 6.93 (1H, d, J=8 Hz), 7.2–7.8 (10H, m)

Preparation 7
(1) (1R)-1-Hydroxy-5-t-butyldiphenylsilyloxy-1,2,3,4-tetrahydronaphthalene was obtained according to a similar manner to that of Preparation 6 (1). HPLC; chiralcel AD, 2% isopropanol/hexane, 23.8 ml/min
(2) (1S)-1-Azido-5-t-butyldiphenylsilyloxy-1,2,3,4-tetrahydronaphthalene was obtained according to a similar manner to that of Preparation 6 (2).
(3) (1S)-1-(4,5-Diphenyloxazol-2-yl)methylamino-5-t-butyldiphenylsilyloxy-1,2,3,4-tetrahydronaphthalene was obtained according to a similar manner to that of Preparation 6 (3).

Preparation 8

To a solution of (1R)-1-hydroxy-5-t-butyldiphenylsilyloxy-1,2,3,4-tetrahydronaphthalene (1.5 g) in THF (20 ml) were added n-butyllithium (2.8 ml, 1.5M solution in hexane), (4,5-diphenyloxazol-2-yl)methyl bromide (1.8 g) and NaI (1.2 g) at −78° C. under $N_2$. The solution was warmed to the room temperature and stirred for 6 hours. The mixture was poured into a mixture of ethyl acetate and water. The organic layer was washed with 1N-HCl solution, sat. $NaHCO_3$ and brine, dried over $MgSO_4$, and evaporated in vacuo. The residue was purified by chromatography on silica gel to afford (1R)-1-(4,5-diphenyloxazol-2-yl)methyloxy-5-t-butyldiphenylsilyloxy-1,2,3,4-tetrahydronaphthalene (1.65 g).

MS (m/z): 636 ($M^+$+1)

IR (Neat): 3400 $cm^{-1}$

NMR ($CDCl_3$, δ): 1.09 (9H, s), 1.6–2.2 (4H, m), 2.6–3.2 (2H, m), 4.65 (1H, m), 4.75 (1H, d, J=13.2 Hz), 4.84 (1H, d, J=13.2 Hz), 6.31 (1H, d, J=8 Hz), 6.75 (1H, t, J=8 Hz), 6.98 (1H, d, J=8 Hz), 7.2–7.8 (10H, m)

Preparation 9

(1S)-1-(4,5-Diphenyloxazol-2-yl)methyloxy-5-t-butyldiphenylsilyloxy-1,2,3,4-tetrahydronaphthalene was obtained according to a similar manner to that of Preparation 8.

Preparation 10

To a solution of D-pyroglutamic acid (30 g) in $CH_2Cl_2$ (200 ml) were added benzoin (74 g), 1-ethyl-3-(3-dimethylaminopropyl)carbodiimide (68 ml) and 4-dimethylaminopyridine (30 g) at room temperature under $N_2$. After being stirred for 12 hours at room temperature, the solvent was evaporated in vacuo, and the residue was partitioned between ethyl acetate and water. The organic layer was washed with 1N-HCl solution, sat. $NaHCO_3$ and brine, dried over $MgSO_4$, and evaporated in vacuo. The obtained compound and ammonium acetate (60 g) were dissolved in acetic acid (500 ml) and the mixture was stirred for 4 hours at 100° C. After the solvent was removed, the residue was partitioned between ethyl acetate and water. The organic layer was washed with water, sat. $NaHCO_3$ and brine. The dried solvent was evaporated in vacuo and the residue was purified by chromatography on silica gel to give (5R)-5-(4,5-diphenyloxazol-2-yl)pyrrolidin-2-one (21.2 g).

MS (m/z): 305 ($M^+$+1)

IR (Neat): 3200, 1680, 1640 $cm^{-1}$

NMR ($CDCl_3$, δ): 2.3–2.8 (4H, m), 4.8–5.0 (1H, m), 6.24 (1H, br s), 7.2–7.7 (10H, m)

Preparation 11

To a solution of (5R)-5-(4,5-diphenyloxazol-2-yl)pyrrolidin-2-one (12 g) in tetrahydrofuran (THF) (200 ml) were added butyllithium (26 ml, 1.6N solution in hexane) and benzyloxycarbonyl chloride (6.8 ml) at −78° C. under $N_2$. The mixture was stirred for 1 hour at the same temperature and partitioned between ethyl acetate and water. The organic layer was washed with 1N-HCl, water, sat. $NaHCO_3$ and brine. The dried solvent was evaporated in vacuo, the residue was dissolved in THF (200 ml), and 1N-NaOH (87 ml) was added at 0° C. After being stirred for 12 hours at room temperature, the solvent was evaporated in vacuo. After the residue was partitioned between hexane and water, aqueous layer was adjusted to pH=2 and extracted with ethyl acetate. The organic layer was washed with water, sat. $NaHCO_3$ and brine. The dried solvent was evaporated in vacuo and the residue was dissolved in THF (200 ml). To the solution were added triethylamine (9.0 ml) and ethyl chloroformate (5.0 ml) at −5° C. under $N_2$ and the mixture was stirred for 1 hour at the same temperature. After the filtration, the solution was dropwise added to the solution of $NaBH_4$ (3.2 g) in a mixture of THF (100 ml) and water (100 ml) at 0° C. and stirred for 1 hour. The mixture was partitioned between ethyl acetate and water. The organic layer was washed with 1N-HCl, sat. $NaHCO_3$ and brine. The dried solvent was evaporated in vacuo and the residue was purified by chromatography on silica gel to give (1R)-N-benzyloxycarbonyl-4-hydroxy-1-(4,5-diphenyloxazol-2-yl)butylamine (13 g).

MS (m/z): 443 ($M^+$+1)

IR (Neat): 3300, 1700 $cm^{-1}$

NMR ($CDCl_3$, δ): 1.6–2.2 (4H, m), 3.68 (2H, m), 5.10–5.2 (1H, m), 5.14 (2H, s), 5.73 (1H, d, J=10.0 Hz), 7.2–7.7 (10H, m)

Preparation 12

A mixture of (1R)-N-benzyloxycarbonyl-4-hydroxy-1-(4,5-diphenyloxazol-2-yl)butylamine (12 g) and 10% Pd/C (2 g) in methanol (20 ml) was stirred under $H_2$ for 5 hours. The catalyst was filtered off and filtrate was evaporated. The residue was recrystallized with ether to give (1R)-4-hydroxy-1-(4,5-diphenyloxazol-2-yl)butylamine (5.8 g).

MS (m/z): 309 ($M^+$+1)

NMR ($CDCl_3$, δ): 1.7–2.0 (3H, m), 2.1–2.4 (1H, m), 2.6–2.8 (3H, m), 3.5–3.8 (2H, m), 4.0–4.2 (1H, m), 7.3–7.8 (10H, m)

Preparation 13

The mixture of (1R)-4-hydroxy-1-(4,5-diphenyloxazol-2-yl)butylamine (5.8 g), 5-tert-butyldiphenylsilyloxy-1-tetralone (11 g) and p-toluenesulphonic acid (32 mg) in toluene (150 ml) was heated under reflux in Dean-Stark apparatus for 48 hours. After the solvent was removed in vacuo, the residue was dissolved in a mixture of methanol (50 ml) and THF (200 ml) and $NaBH_4$(0.4 g) was added to the solution at −78° C. After being stirred for 4 hours at the same temperature, the solution was allowed to stand at the room temperature for 30 minutes, then poured into the mixture of ethyl acetate and water. The organic layer was washed with water and brine, dried over $MgSO_4$ and evaporated in vacuo. The residue was purified by chromatography on silica gel to afford (1R)-1-[[(1R)-4-hydroxy-1-(4,5-diphenyloxazol-2-yl)butyl]amino]-5-tert-butyldiphenylsilyloxy-1,2,3,4-tetrahydronaphthalene (10.2 g).

MS (m/z): 693 ($M^+$)

IR (Neat): 3400, 1580 $cm^{-1}$

NMR ($CDCl_3$, δ): 1.08 (9H, s), 1.6–2.2 (8H, m), 2.6–3.1 (2H, m), 3.61 (2H, t, J=6.0 Hz), 3.88 (1H, m), 4.13 (1H, m), 6.30 (1H, d, J=8.0 Hz), 6.72 (1H, t, J=8.0 Hz), 6.92 (1H, d, J=8.0 Hz), 7.3–7.8 (20H, m)

Preparation 14

To a solution of (1R)-1-[[(1R)-4-hydroxy-1-(4,5-diphenyloxazol-2-yl)butyl]amino]-5-tert-butyldiphenylsilyloxy-1,2,3,4-tetrahydronaphthalene (2.6 g) in $CH_2Cl_2$ (50 ml) was added $SOCl_2$ (3 ml). After being stirred for 12 hours, the solvent was removed. The residue was dissolved in N,N-dimethylformamide (DMF) (15 ml) and $K_2CO_3$ (2 g) was added to the solution. After being stirred for 4 hours at the room temperature, the solution was poured into the mixture of ethyl acetate and water. The organic layer was washed with water and brine, dried over $MgSO_4$ and evaporated in vacuo. The residue was purified by chromatography on silica gel to afford (1R)-1-[(2R)-2-(4,5-diphenyloxazol-2-yl)pyrrolidin-1-yl]-5-tert-butyldiphenylsilyloxy-1,2,3,4-tetrahydronaphthalene (1.22 g).

MS (m/z): 675 ($M^+$)

IR (Neat): 1560 $cm^{-1}$

NMR (CDCl₃, δ): 1.75 (9H, s), 1.5–2.4 (8H, m), 2.7–3.2 (4H, m), 4.0–4.3 (2H, m), 6.15 (1H, d, J=8 Hz), 6.45 (1H, t, J=8 Hz), 6.92 (1H, d, J=8 Hz), 7.2–7.8 (20H, m)

Preparation 15

The following compounds were obtained according to a similar manner to that of Preparation 14.

(1) (1S)-1-[(2R)-2-(4,5-Diphenyloxazol-2-yl)pyrrolidin-1-yl]-5-tert-butyldiphenylsilyloxy-1,2,3,4-tetrahydronaphthalene MS (m/z): 675 (M⁺)

IR (Neat): 1580 cm⁻¹

NMR (CDCl₃, δ): 1.80 (9H, s), 1.5–2.4 (8H, m), 2.6–3.2 (4H, m), 3.9–4.1 (1H, m), 4.33 (1H t, J=7.4 Hz), 6.25 (1H, d, J=8 Hz), 6.72 (1H, t, J=8 Hz), 7.2–7.8 (21H, m)

(2) (1S)-1-[(2S)-2-(4,5-Diphenyloxazol-2-yl)pyrrolidin-1-yl]-5-tert-butyldiphenylsilyloxy-1,2,3,4-tetrahydronaphthalene MS (m/z): 675 (M⁺)

IR (Neat): 1560 cm⁻¹

NMR (CDCl₃, δ): 1.75 (9H, s), 1.5–2.4 (8H, m), 2.7–3.2 (4H, m), 4.0–4.3 (2H, m), 6.15 (1H, d, J=8 Hz), 6.45 (1H, t, J=8 Hz), 6.92 (1H, d, J=8 Hz), 7.2–7.8 (20H, m)

(3) (1R)-1-[(2S)-2-(4,5-Diphenyloxazol-2-yl)pyrrolidin-1-yl]-5-tert-butyldiphenylsilyloxy-1,2,3,4-tetrahydronaphthalene MS (m/z): 675 (M⁺)

IR (Neat): 1580 cm⁻¹

NMR (CDCl₃, δ): 1.80 (9H, s), 1.5–2.4 (8H, m), 2.6–3.2 (4H, m), 3.9–4.1 (1H, m), 4.33 (1H, t, J=7.4 Hz), 6.25 (1H, d, J=8 Hz), 6.72 (1H, t, J=8 Hz), 7.2–7.8 (21H, m)

Preparation 16

Dichloromethane solution (10 ml) of 1-amino-2,3-dihydro-4-methoxy-1H-indene (0.38 g), trifluoroacetic anhydride (0.50 ml), pyridine (0.35 ml) and 4-dimethylaminopyridine (catalytic amount) were stirred for 40 minutes at 0° C. and for 2 days at ambient temperature. The solvent was removed in vacuo. The residue was extracted with ethyl acetate. The mixture was washed with 1N HCl solution and brine, dried over MgSO₄, and evaporated in vacuo to afford 1-trifluoroacetamido-2,3-dihydro-4-methoxy-1H-indene (0.47 g).

MS (m/z): 147 (M⁺-CF₃CONH)

IR (Nujol): 1690 cm⁻¹

NMR (CDCl₃, δ): 1.65–1.96 (1H, m), 2.58–3.08 (3H, m), 3.85 (3H, s), 5.50 (1H, q, J=7.6 Hz), 6.44 (1H, br), 6.80 (1H, d, J=8.1 Hz), 6.90 (1H, d, J=7.6 Hz), 7.25 (1H, dd, J=7.6, 8.1 Hz)

Preparation 17

To a solution of 1-trifluoroacetamido-2,3-dihydro-4-methoxy-1H-indene (0.44 g) and 4,5-diphenyl-2-bromomethyloxazole (0.55 g) in DMF was added K₂CO₃ (0.30 g). After being stirred for 12 hours, the solution was extracted with ethyl acetate. The mixture was washed with brine, dried over MgSO₄ and evaporated in vacuo. The residue was purified by chromatography on silica gel to afford 1-(N-trifluoroacetyl-N-[(4,5-diphenyloxazol-2-yl)methyl]amino]-2,3-dihydro-4-methoxy-1H-indene (0.30 g).

MS (m/z): 493 (M⁺+1)

IR (Nujol): 1680 cm⁻¹

NMR (CDCl₃, δ): 2.15–2.45 (1H, m), 2.78–3.20 (2H, m), 2.50–2.75 (1H, m), 3.82 (3H, s), 4.38 (1H, d, J=16.2 Hz), 4.62 (1H, d, J=16.2 Hz), 5.77 (1H, t, J=7.5 Hz), 6.73 (1H, d, J=8.1 Hz), 6.76 (1H, d, J=7.5 Hz), 7.16 (1H, dd, J=7.5, 8.1 Hz), 7.32–7.34 (6H, m), 7.48–7.59 (4H, m)

Preparation 18

To a solution of 1-[N-trifluoroacetyl-N-[(4,5-diphenyloxazol-2-yl)methyl]amino]-2,3-dihydro-4-methoxy-1H-indene (0.29 g) of methanol (2 ml) was added 1N NaOH aqueous solution (2 ml). The mixture was refluxed for 1 day and the solvent was removed in vacuo. The residue was extracted with ethyl acetate, dried over MgSO₄ and evaporated in vacuo. The residue was purified by chromatography on silica gel to afford 1-(4,5-diphenyloxazol-2-yl)methylamino-2,3-dihydro-4-methoxy-1H-indene (0.19 g).

MS (m/z): 397 (M⁺+1)

NMR (CDCl₃, δ): 1.85–2.10 (1H, m), 2.10 (1H, br), 2.33–2.52 (1H, m), 2.68–2.87 (1H, m), 2.92–3.12 (1H, m), 3.82 (3H, s), 4.14 (2H, s), 4.45 (1H, t, J=6.1 Hz), 6.74 (1H, d, J=7.9 Hz), 7.05 (1H, d, J=7.4 Hz), 7.20 (1H, dd, J=7.4, 7.9 Hz), 7.32–7.40 (6H, m), 7.57–7.67 (4H, m)

Preparation 19

To a solution of 1-(4,5-diphenyloxazol-2-yl) methylamino-2,3-dihydro-4-methoxy-1H-indene (0.18 g) and methyl iodide (85 mg) in DMF (3 ml) was added K₂CO₃ (0.12 g). After being stirred for 16 hours, the solution was extracted with ethyl acetate. The mixture was washed with brine, dried over MgSO₄ and evaporated in vacuo. The residue was purified by chromatography on silica gel to afford 1-[N-methyl-N-[(4,5-diphenyloxazol-2-yl)methyl]amino]-2,3-dihydro-4-methoxy-1H-indene (0.13 g).

MS (m/z): 411 (M⁺+1)

NMR (CDCl₃, δ): 2.02–2.28 (1H, m), 2.44 (3H, s), 2.64–3.17 (3H, m), 3.82 (5H, s), 4.60 (1H, br), 6.73 (1H, d, J=7.9 Hz), 7.08–7.32 (2H, m), 7.32–7.48 (6H, m), 7.58–7.72 (4H, m)

EXAMPLE 1

To a solution of 2-(4,5-diphenyloxazol-2-yl)-3-(3-t-butyldiphenylsilyloxybenzyl)tetrahydrofuran (1.5 g) in THF (30 ml) was added tetrabutylammonium fluoride (2.4 ml, 1N-THF solution). After being stirred for 1 hour at the room temperature, the solution was extracted with ethyl acetate. The extract was washed with water and brine. The dried solvent was evaporated in vacuo. The obtained oil was dissolved into DMF (10 ml) and then K₂CO₃ (2.0 g) and ethyl bromoacetate (0.4 ml) were added at room temperature. The mixture was stirred for 2 hours at the same temperature and partitioned between ethyl acetate and water. The organic layer was washed with water, sat. NaHCO₃ and brine. The dried solvent was evaporated in vacuo and the residue was purified by chromatography on silica gel to give ethyl [3-[[2-(4,5-diphenyloxazol-2-yl)tetrahydrofuran-3-yl]methyl]phenoxy]acetate (680 mg).

MS (m/z): 484 (M⁺+1)

IR (Neat): 1760 cm⁻¹

NMR (CDCl₃, δ): 1.1–1.3 (3H, m), 1.8–3.2 (5H, m), 3.8–4.4 (4H, m), 4.51 and 4.53 (2H, each s), 4.78 (1/3H, d, J=6.6 Hz), 5.23 (2/3H, d, J=7.2 Hz), 6.6–7.0 (3H, m), 7.1–7.8 (11H, m)

EXAMPLE 2

To a solution of (1R)-1-(4,5-diphenyloxazol-2-yl) methylamino-5-t-butyldiphenylsilyloxy-1,2,3,4-tetrahydronaphthalene in THF (20 ml) was added tetrabutylammonium fluoride (3.3 ml, 1N-THF solution). After being stirred for 1 hour at the room temperature, the solution was extracted with ethyl acetate. The mixture was washed with water and brine. The dried solvent was evaporated in vacuo. The obtained oil was dissolved into DMF (10 ml), and NaH (60% in oil, 93 mg) and ethyl bromoacetate (0.24 ml) were added at room temperature. The mixture was stirred for 2 hours at the same temperature and partitioned between ethyl acetate and water. The organic layer was washed with water, sat. NaHCO$_3$, and brine. The dried solvent was evaporated in vacuo and the residue was purified by chromatography on silica gel to give (1R)-1-(4,5-diphenyloxazol-2-yl)methylamino-5-ethoxycarbonylmethoxy-1,2,3,4-tetrahydronaphthalene (480 mg).

MS (m/z): 483 (M$^+$+1)

IR (Neat): 3400, 1720 cm$^{-1}$

NMR (CDCl$_3$, δ): 1.25 (3H, t, J=7 Hz), 1.6–2.2 (4H, m), 2.5–3.0 (2H, m), 3.92 (1H, t, J=4.4 Hz), 4.10 (2H, s), 4.25 (2H, q, J=7 Hz), 4.60 (2H, s), 6.57 (1H, m), 7.0–7.9 (12H, m)

HPLC; chiralcel AD, 10% isopropanol/hexane, 13.1 ml/min

EXAMPLE 3

The following compounds were obtained according to similar manners to those of Examples 1 and 2.
(1) Ethyl [3-[[2-(4,5-diphenyloxazol-2-yl)-tetrahydrothiophen-3-yl]methyl]phenoxy]acetate
MS (m/z): 500 (M$^+$+1)
IR (Neat): 1740 cm$^{-1}$
NMR (CDCl$_3$, δ): 1.25 (3H, t, J=7 Hz), 1.8–3.2 (7H, m), 4.0–4.4 (3H, m), 4.42 (2H, s), 6.6–6.9 (3H, m), 7.18 (1H, t, J=8 Hz), 7.2–7.8 (10H, m)
(2) (1S)-1-(4,5-Diphenyloxazol-2-yl)methylamino-5-ethoxycarbonylmethoxy- 1,2,3,4-tetrahydronaphthalene
HPLC; chiralcel AD, 10% isopropanol/hexane, 12.0 ml/min
(3) (1R)-1-(4,5-Diphenyloxazol-2-yl)methyloxy-5-ethoxycarbonylmethoxy-1,2,3,4-tetrahydronaphthalene
MS (m/z): 484 (M$^+$+1)
NMR (CDCl$_3$, δ): 1.25 (3H, t, J=7 Hz), 1.6–2.2 (4H, m), 2.6–3.0 (2H, m), 4.25 (2H, q, J=7 Hz), 4.60 (2H, s), 4.64 (1H, m), 4.75 (1H, d, J=13.0 Hz), 4.82 (1H, d, J=13.0 Hz), 6.65 (1H, m), 7.0–7.9 (12H, m)
HPLC; chiralcel AD, 5% isopropanol/hexane, 15.5 ml/min
(4) (1S)-1-(4,5-Diphenyloxazol-2-yl)methyloxy-5-ethoxycarbonylmethoxy-1,2,3,4-tetrahydronaphthalene
HPLC; chiralcel AD, 5% isopropanol/hexane, 11.5 ml/min

EXAMPLE 4

To a solution of 1-[2-(4,5-diphenyloxazol-2-yl)pyrrolidin-1-yl]-5-methoxy-1,2,3,4-tetrahydronaphthalene (0.57 g) in dichloromethane (10 ml) was added BBr$_3$ (5 ml, 1M solution in dichloromethane) at 0° C. After being stirred for 2 hours, the solvent was evaporated in vacuo. The residue was diluted with ethyl acetate, and the mixture was washed with sat. NaHCO$_3$ and brine. The dried solvent was evaporated in vacuo. The obtained oil was dissolved into DMF (10 ml) and then K$_2$CO$_3$ (1.0 g) and ethyl bromoacetate (0.3 ml) were added at room temperature. The mixture was stirred for 2 hours at the same temperature and then partitioned between ethyl acetate and water. The organic layer was washed with water, sat. NaHCO$_3$ and brine. The dried solvent was evaporated in vacuo and the residue was purified by chromatography on silica gel to give 1-[2-(4,5-diphenyloxazol-2-yl)pyrrolidin-1-yl]-5-ethoxycarbonylmethoxy-1,2,3,4-tetrahydronaphthalene (430 mg).

MS (m/z): 523 (M$^+$+1)

IR (Neat): 1750 cm$^{-1}$

NMR (CDCl$_3$, δ): 1.24 (3H, t, J=7 Hz), 1.5–2.4 (8H, m), 2.5–3.2 (4H, m), 4.22 (2H, q, J=7 Hz), 4.0–4.4 (1H, m), 4.42 (2H, s), 4.4–4.6 (1H, m), 6.38 (1H, d, J=8 Hz), 6.84 (1H, t, J=8 Hz), 7.05 (1H, d, J=8 Hz), 7.2–7.7 (10H, m)

EXAMPLE 5

The following compounds were obtained according to a similar manner to that of Example 4.
(1) Ethyl [3-[[2-(4,5-diphenyloxazol-2-yl)-1-benzylpyrrolidin-3-yl]methyl]phenoxy]acetate
MS (m/z): 573 (M$^+$+1)
IR (Neat): 1740 cm$^{-1}$
NMR (CDCl$_3$, δ): 1.8–3.2 (7H, m), 3.6–4.0 (2H, m), 4.0–4.4 (3H, m), 4.42, 4.38 (2H, each s), 6.5–6.9 (3H, m), 7.1–7.8 (16H, m)
(2) Ethyl [3-[[2-(4,5-diphenyloxazol-2-yl)-2-cyclohepten-1-yl]methyl]phenoxy]acetate
MS (m/z): 508 (M$^+$+1)
IR (Neat): 1740 cm$^{-1}$
NMR (CDCl$_3$, δ): 1.25 (3H, t, J=7 Hz), 1.3–2.0 (6H, m), 2.5 (2H, m), 2.82 (1H, dd, J=8.0, 12.0 Hz), 3.01 (1H, dd, J=6.0, 12.0 Hz), 3.74 (1H, m), 4.13 (2H, q, J=7 Hz), 6.7–7.0 (3H, m), 7.0–7.9 (12H, m)

EXAMPLE 6

To a solution of ethyl [3-[[2-(4,5-diphenyloxazol-2-yl)tetrahydrothiophen-3-yl]methyl]phenoxy]acetate (0.6 g) in CH$_2$Cl$_2$ (20 ml) was added m-chloroperbenzoic acid (520 mg) at 0° C. After being stirred for 4 hours, the solvent was removed in vacuo. The residue was extracted with ethyl acetate. The mixture was washed with 1N-HCl solution, sat. NaHCO$_3$ and brine, dried over MgSO$_4$, and evaporated in vacuo. The residue was purified by chromatography on silica gel to afford 2-(4,5-diphenyloxazol-2-yl)-3-[3-(ethoxycarbonylmethoxy)benzyl]tetrahydrothiophen 1,1-dioxide.

MS (m/z): 532 (M$^+$+1)

IR (Neat): 1740 cm$^{-1}$

NMR (CDCl$_3$, δ): 1.25 (3H, t, J=7 Hz), 1.8–2.4 (2H, m), 2.7–3.5 (5H, m), 4.0–4.4 (3H, m), 4.47 (2H, s), 6.6–6.9 (3H, m), 7.16 (1H, t, J=8 Hz), 7.2–7.8 (10H, m)

EXAMPLE 7

To a solution of ethyl [3-[[2-(4,5-diphenyloxazol-2-yl)tetrahydrofuran-3-yl]methyl]phenoxy]acetate (560 mg) in ethanol (20 ml) was added 1N-NaOH solution (1.2 ml). After being stirred for 4 hours at the same temperature, the solvent was removed in vacuo to give sodium [3-[[2-(4,5-diphenyloxazol-2-yl)tetrahydrofuran-3-yl]methyl]phenoxy]-acetate (0.46 g).

FABMS (m/z): 478 (M$^+$+1)

IR (Nujol): 3400, 1600 cm$^{-1}$

NMR (DMSO-d$_6$, δ): 1.6–3.0 (5H, m), 3.8–4.2 (4H, m), 4.68 (1/3H, d, J=7.0 Hz), 5.13 (2/3H, d, J=8.0 Hz), 6.6–6.8 (3H, m), 7.0 (1H, t, J=8 Hz), 7.2–7.8 (10H, m)

EXAMPLE 8

To a solution of 1-[2-(4,5-diphenyloxazol-2-yl)pyrrolidin-1-yl]-5-ethoxycarbonylmethoxy-1,2,3,4-tetrahydronaphthalene (430 mg) in ethanol (20 ml) was added 1N-NaOH solution (0.82 ml). After being stirred for 4 hours at the same temperature, the solvent was removed in vacuo to give sodium salt of 1-(2-(4,5-diphenyloxazol-2-yl)pyrrolidin-1-yl]-5-carboxymethoxy-1,2,3,4-tetrahydronaphthalene (0.24 g).

FABMS (m/z): 517 (M⁺+1)

IR (Nujol): 3400, 1600 cm⁻¹

NMR (DMSO-d₆ δ) 1.4–2.3 (8H, m), 2.4–3.1 (4H, m), 4.07 (2H, s), 4.0–4.4 (2H, m), 6.3–6.6 (1H, m), 6.6–7.1 (2H, m), 7.2–7.6 (10H, m)

EXAMPLE 9

The following compounds were obtained according to similar manners to those of Examples 7 and 8.

(1) Sodium [3-([2-(4,5-diphenyloxazol-2-yl) tetrahydrothiophen-3-yl]methyl]phenoxylacetate FABMS (m/z): 494 (M⁺+1)

IR (Nujol): 3400, 1600 cm⁻¹

NMR (DMSO-d₆, δ): 1.6–3.2 (7H, m), 4.05 (2H, s), 4.39 (2/3H, d, J=6.6 Hz), 4.53 (1/3H, d, J=5.8 Hz), 6.6–6.8 (3H, m), 7.07 (1H, t, J=8 Hz), 7.2–7.8 (10H, m)

(2) 2-(4,5-Diphenyloxazol-2-yl)-3-[3-(carboxymethoxy) benzyl]tetrahydrothiophene 1,1-dioxide MS (m/z): 504 (M⁺+1)

IR (Nujol): 3400, 1600 cm⁻¹

NMR (CDCl₃, δ): 1.8–2.4 (2H, m), 2.8–3.4 (5H, m), 4.28 (1H, d, J=10.3 Hz), 4.48 (2H, s), 6.6–6.9 (3H, m), 7.16 (1H, t, J=8 Hz), 7.2–7.8 (10H, m)

(3) Sodium [3-[[2-(4,5-diphenyloxazol-2-yl)-1-benzylpyrrolidin-3-yl]methyl]phenoxy]acetate FABMS (m/z): 567 (M⁺+1)

IR (Nujol): 3400, 1600 cm⁻¹

NMR (DMSO-d₆, δ): 1.8–3.2 (7H, m), 3.4–3.8 (2H, m), 4.10 (2H, s), 4.0–4.1 (1H, m), 6.5–6.8 (3H, m), 7.02 (1H, t, J=8 Hz), 7.1–7.8 (15H, m)

(4) Sodium [3-[[2-(4,5-diphenyloxazol-2-yl)-2-cyclohepten-1-yl]methyl]phenoxy]acetate IR (Neat): 1600 cm⁻¹

NMR (DMSO-d₆, δ) 1.2–2.0 (6H, m), 2.3–2.5 (2H, m), 2.8 (2H, m), 4.10 (2H, s), 6.64 (1H, d, J=8 Hz), 6.76 (1H, d, J=8 Hz), 6.81 (1H, s), 7.0–7.2 (2H, m), 7.2–7.8 (10H, m)

(5) (1R) -1-(4,5-Diphenyloxazol-2-yl)methylamino-5-carboxymethoxy-1,2,3,4-tetrahydronaphthalene FABMS (m/z): 455 (M⁺+1)

IR (Nujol): 3400, 1700 cm⁻¹

NMR (DMSO-d₆, δ): 1.4–2.2 (4H, m), 2.4–2.8 (2H, m), 3.40 (1H, m), 4.01 (2H, s), 4.64 (2H, s), 6.67 (1H, m), 7.0–7.8 (13H, m)

(6) (1S)-1-(4,5-Diphenyloxazol-2-yl)methylamino-5-carboxymethoxy-1,2,3,4-tetrahydronaphthalene (7) Sodium salt of (1R)-1-(4,5-diphenyloxazol-2-yl) methyloxy-5-carboxymethoxy-1,2,3,4-tetrahydronaphthalene FABMS (m/z): 478 (M⁺+1)

NMR (DMSO-d₆, δ): 1.6–2.2 (4H, m), 2.4–2.8 (2H, m), 4.11 (2H, m), 4.60 (1H, m), 4.72 (1H, d, J=13.4 Hz), 4.80 (1H, d, J=13.4 Hz), 6.61 (1H, d, J=7.5 Hz), 6.88 (1H, d, J=7.5 Hz), 7.03 (1H, t, J=7.5 Hz), 7.2–7.8 (10H, m)

(8) Sodium salt of (1S)-1-(4,5-diphenyloxazol-2-yl) methyloxy-5-carboxymethoxy-1,2,3,4-tetrahydronaphthalene

EXAMPLE 10

The following compound was obtained by reacting ethyl [3-[[2-(4,5-diphenyloxazol-2-yl)-1-benzylpyrrolidin-3-yl] methyl]phenoxy]acetate according to similar manners to those of Preparation 1 (2) and Example 7.

[3-[[2-(4,5-Diphenyloxazol-2-yl)pyrrolidin-3-yl]methyl3-phenoxy]acetic acid

FABMS (m/z): 455 (M⁺+1)

IR (Nujol): 3400, 1600 cm⁻¹

NMR (DMSO-d₆, δ): 1.5–2.2 (2H, m), 2.4–3.2 (5H, m), 4.19 (2/3H, d, J=6 Hz), 4.41 (2H, s), 4.57 (1/3H, d, J=7 Hz), 6.5–6.8 (3H, m), 7.11 (1H, t, J=8 Hz), 7.2–7.8 (10H, m)

EXAMPLE 11

To a solution of [3-[[2-(4,5-diphenyloxazol-2-yl) pyrrolidin-3-yl]methyl]phenoxy]acetic acid (140 mg) in a mixture of THF (10 ml) and water (10 ml) was added acetyl chloride (1.0 ml) dropwise at 0° C. keeping pH 8-9 with 1N NaOH solution. The mixture was partitioned between ethyl acetate and water. The organic layer was washed with water, 1N-HCl and brine. The dried solvent was evaporated in vacuo and the residue was purified by trituration with hexane to afford [3-[[2-(4,5-diphenyloxazol-2-yl)-1-acetylpyrrolidin-3-yl]methyl]phenoxy]acetic acid (150 mg).

FABMS (m/z): 497 (M⁺+1)

IR (Nujol): 3400, 1600 cm⁻¹

NMR (DMSO-d₆, δ): 1.8–2.4 (5H, m), 2.6–3.1 (3H, m), 3.2–3.9 (2H, m), 4.58, 4.61 (2H, each s), 4.8–5.2 (1H, m), 6.6–7.0 (3H, m), 7.1–7.8 (11H, m)

EXAMPLE 12

The following compound was obtained by reacting ethyl [3-[[2-(4,5-diphenyloxazol-2-yl)-2-cyclohepten-1-yl] methyl]phenoxy]acetate according to similar manners to those of Preparation 1 (2) and Example 7.

Sodium [3-[[2-(4,5-diphenyloxazol-2-yl)cycloheptyl] methyl]phenoxy]acetate

IR (Neat): 1600 cm⁻¹

NMR (DMSO-d₆, δ): 1.0–2.0 (10H, m), 2.0–2.8 (4H, m), 4.07 (2H, s), 6.5–6.7 (3H, m), 7.08 (1H, t, J=8 Hz), 7.2–7.8 (10H, m)

EXAMPLE 13

To a solution of (1R)-1-[(2R)-2-(4,5-diphenyloxazol-2-yl)pyrrolidin-1-yl]-5-tert-butyldiphenylsilyloxy-1,2,3,4-tetrahydronaphthalene (1.22 g) in THF (20 ml) was added tetrabutylammonium fluoride (2.7 ml, 1M solution in THF) at 0° C. After being stirred for 2 hours at the room temperature, the mixture was diluted with ethyl acetate and washed with water and brine. The dried solvent was evaporated in vacuo. The obtained oil was dissolved into DMF (10 ml) and then K₂CO₃ (2.0 g) and ethyl bromoacetate (0.3 ml) were added at room temperature. The mixture was stirred for 2 hours at the same temperature and then partitioned between ethyl acetate and water. The organic layer was washed with water, sat. NaHCO₃ and brine. The dried solvent was evaporated in vacuo and the residue was purified by chromatography on silica gel to give (1R)-1-[(2R)-2-(4,5-diphenyloxazol-2-yl)pyrrolidin-1-yl]-5-ethoxycarbonylmethoxy-1,2,3,4-tetrahydronaphthalene (800 mg).

MS (m/z): 523 (M⁺+1)

IR (Neat): 1750 cm⁻¹

NMR (CDCl₃, δ): 1.24 (3H, t, J=7 Hz), 1.5–2.4 (8H, m), 2.5–3.2 (4H, m), 4.0–4.4 (2H, m), 4.22 (2H, q, J=7 Hz), 4.44 (2H, s), 6.37 (1H, d, J=8 Hz), 6.83 (1H, t, J=8 Hz), 7.06 (1H, d, J=8 Hz), 7.2–7.7 (10H, m)

EXAMPLE 14

The following compounds were obtained according to a similar manner to that of Example 13.

(1) (1S)-1-[(2R)-2-(4,5-Diphenyloxazol-2-yl)pyrrolidin-1-yl]-5-ethoxycarbonylmethoxy-1,2,3,4-tetrahydronaphthalene MS (m/z): 523 (M⁺)

IR (Neat): 1750 cm⁻¹

NMR (CDCl$_3$, δ): 1.24 (3H, t, J=7 Hz), 1.5–2.4 (8H, m), 2.5–2.7 (2H, m), 2.8–3.0 (2H, m), 3.9–4.1 (1H, m), 4.1–4.3 (1H, m), 4.24 (2H, q, J=7 Hz), 4.55 (2H, s), 6.52 (1H, d, J=8 Hz), 7.08 (1H, t, J=8 Hz), 7.46 (1H, d, J=8 Hz), 7.2–7.7 (10H, m)

(2) (1S)-1-[(2S)-2-(4,5-Diphenyloxazol-2-yl)pyrrolidin-1-yl]-5-ethoxycarbonylmethoxy-1,2,3,4-tetrahydronaphthalene MS (m/z): 523 (M⁺+1)

IR (Neat): 1750 cm⁻¹

NMR (CDCl$_3$, δ): 1.24 (3H, t, J=7 Hz), 1.5–2.4 (8H, m), 2.5–3.2 (4H, m), 4.0–4.4 (2H, m), 4.22 (2H, q, J=7 Hz), 4.44 (2H, s), 6.37 (1H, d, J=8 Hz), 6.83 (1H, t, J=8 Hz), 7.06 (1H, d, J=8 Hz), 7.2–7.7 (10H, m)

(3) (1R)-1-[(2S)-2-(4,5-Diphenyloxazol-2-yl)pyrrolidin-1-yl]-5-ethoxycarbonylmethoxy-1,2,3,4-tetrahydronaphthalene MS (m/z): 523 (M⁺)

IR (Neat): 1750 cm⁻¹

NMR (CDCl$_3$, δ): 1.24 (3H, t, J=7 Hz), 1.5–2.4 (8H, m), 2.5–2.7 (2H, m), 2.8–3.0 (2H, m), 3.9–4.1 (1H, m), 4.1–4.3 (1H, m), 4.24 (2H, q, J=7 Hz), 4.55 (2H, s), 6.52 (1H, d, J=8 Hz), 7.08 (1H, t, J=8 Hz), 7.46 (1H, d, J=8 Hz), 7.2–7.7 (10H, m)

EXAMPLE 15

To a solution of (1R)-1-[(2R)-2-(4,5-diphenyloxazol-2-yl)pyrrolidin-1-yl]-5-ethoxycarbonylmethoxy-1,2,3,4-tetrahydronaphthalene (700 mg) in ethanol (20 ml) was added 1N-NaOH solution (1.3 ml). After being stirred for 12 hours at the same temperature, the solvent was removed in vacuo to give sodium salt of (1R)-1-[(2R)-2-(4,5-diphenyloxazol-2-yl)pyrrolidin-1-yl]-5-carboxymethoxy-1,2,3,4-tetrahydronaphthalene (0.53 g).

FABMS (m/z): 517 (M⁺+1)

IR (Nujol): 3400, 1600 cm⁻¹

NMR (DMSO-d$_6$, δ): 1.4–2.3 (8H, m), 2.4–3.1 (4H, m), 4.03 (2H, s), 4.0–4.3 (2H, m), 6.41 (1H, d, J=7.2 Hz), 6.6–6.8 (2H, m), 7.2–7.5 (10H, m)

EXAMPLE 16

The following compounds were obtained according to a similar manner to that of Example 15.

(1) Sodium salt of (1S)-1-[(2R)-2-(4,5-diphenyloxazol-2-yl)pyrrolidin-1-yl]-5-carboxymethoxy-1,2,3,4-tetrahydronaphthalene FABMS (m/z): 517 (M⁺+1)

IR (Nujol): 3400, 1600 cm⁻¹

NMR (DMSO-d$_6$, δ): 1.4–2.3 (8H, m), 2.4–2.9 (4H, m), 3.9 (1H, m), 4.05 (2H, s), 4.30 (1H, t, J=7 Hz), 6.49 (1H, d, J=8.2 Hz), 6.99 (1H, t, J=8.2 Hz), 7.14 (1H, d, J=8.2 Hz), 7.2–7.6 (10H, m)

(2) Sodium salt of (1S)-1-[(2S)-2-(4,5-diphenyloxazol-2-yl)pyrrolidin-1-yl]-5-carboxymethoxy-1,2,3,4-tetrahydronaphthalene FABMS (m/z): 517 (M⁺+1)

IR (Nujol): 3400, 1600 cm⁻¹

NMR (DMSO-d$_6$, δ): 1.4–2.3 (8H, m), 2.4–3.1 (4H, m), 4.03 (2H, s), 4.0–4.3 (2H, m), 6.41 (1H, d, J=7.2 Hz), 6.6–6.8 (2H, m), 7.2–7.5 (10H, m)

(3) Sodium salt of (1R)-1-[(2S)-2-(4,5-diphenyloxazol-2-yl)pyrrolidin-1-yl]-5-carboxymethoxy-1,2,3,4-tetrahydronaphthalene FABMS (m/z): 517 (M⁺+1)

IR (Nujol): 3400, 1600 cm⁻¹

NMR (DMSO-d$_6$, δ): 1.4–2.3 (8H, m), 2.4–2.9 (4H, m), 3.9 (1H, m), 4.05 (2H, s), 4.30 (1H, t, J=7 Hz), 6.49 (1H, d, J=8.2 Hz), 6.99 (1H, t, J=8.2 Hz), 7.14 (1H, d, J=8.2 Hz), 7.2–7.6 (10H, m)

EXAMPLE 17

To a solution of 1-[N-methyl-N-[(4,5-diphenyloxazol-2-yl)methyl]amino]-2,3-dihydro-4-methoxy-1H-indene (109 mg) in dichloromethane (2 ml) was added 1M boron tribromide dichloromethane solution (1 ml) at 0° C. After being stirred for 4 hours at 0° C., the solvent was evaporated in vacuo. The residue was extracted with ethyl acetate. The mixture was washed with brine, dried over MgSO$_4$ and evaporated in vacuo to afford crude 1-[N-methyl-N-[(4,5-diphenyloxazol-2-yl)methyl]amino]-2,3-dihydro-4-hydroxy-1H-indene (109 mg). To a solution of crude 1-[N-methyl-N-[(4,5-diphenyloxazol-2-yl)methyl]amino]-2,3-dihydro-4-hydroxy-1H-indene (109 mg) and ethyl bromoacetate (80 mg) in DMF (3 ml) was added K$_2$CO$_3$ (80 mg). After being stirred for 24 hours, the solution was extracted with ethyl acetate. The mixture was washed with brine, dried over MgSO$_4$ and evaporated in vacuo. The residue was purified by chromatography on silica gel to afford 1-[N-methyl-N-[(4,5-diphenyloxazol-2-yl)methyl]amino]-2,3-dihydro-4-ethoxycarbonylmethoxy-1H-indene (80 mg).

MS (m/z): 483 (M⁺+1)

NMR (CDCl$_3$, δ): 1.29 (3H, t, J=7.1 Hz), 1.98–2.21 (2H, m), 2.41 (3H, s), 2.75–3.18 (2H, m), 3.78 (1H, d, J=12 Hz), 3.82 (1H, d, J=12 Hz), 4.25 (2H, q, J=7.1 Hz), 4.63 (2H, s), 4.55–4.65 (1H, m), 6.62 (1H, m), 7.15–7.18 (2H, m), 7.25–7.45 (6H, m), 7.60–7.75 (4H, m)

EXAMPLE 18

To a solution of 1-[N-methyl-N-[(4,5-diphenyloxazol-2-yl)methyl]amino]-2,3-dihydro-4-ethoxycarbonylmethoxy-1H-indene (80 mg) in ethanol (3 ml) was added 1N NaOH aqueous solution (0.18 ml) at room temperature. After being stirred for 1 day, the solution was evaporated. The residue was washed with ether to afford sodium salt of 1-[N-methyl-N-[(4,5-diphenyloxazol-2-yl)methyl]amino]-2,3-dihydro-4-carboxymethoxy-1H-indene (63 mg).

FABMS (m/z): 499 (M⁺+Na)

IR (Nujol): 1600 cm⁻¹

NMR (CDCl$_3$, δ): 1.89–2.25 (2H, m), 2.40 (3H, s), 2.78–3.10 (2H, m), 3.75 (1H, d, J=14.4 Hz), 3.85 (1H, d, J=14.4 Hz), 4.39 (2H, s), 4.55 (1H, t, J=6.9 Hz), 6.68 (1H, d, J=7.3 Hz), 7.04 (1H, dd, J=7.3, 7.6 Hz), 7.14 (1H, d, J=7.6 Hz), 7.35–7.40 (6H, m), 7.53–7.58 (4H, m)

Preparation 20

To a solution of 3-hydroxymethylphenol (7 g) in N,N-dimethylformamide (40 ml) were added K$_2$CO$_3$ (15 g) ethyl bromoacetate (6.9 ml) at the room temperature. The mixture was stirred for 2 hours at the same temperature and then partitioned between ethyl acetate and water. The organic layer was washed with water, sat. NaHCO$_3$, and brine. The dried solvent was evaporated in vacuo and the residue was purified by chromatography on silica gel to give 3-hydroxymethyl-1-ethoxycarbonylmethoxybenzene (10 g).

MS (m/z): 193 (M⁺−17)

NMR (CDCl$_3$, δ): 1.29 (3H, t, J=7.0 Hz), 2.13 (1H, t, J=6.0 Hz), 4.24 (2H, d, J=7.0 Hz), 4.61 (2H, s), 4.65 (2H, d, J=6.0 Hz), 6.7–7.0 (3H, m), 7.26 (1H, t, J=8.4 Hz)

Preparation 21

To a solution of 3-hydroxymethyl-1-ethoxycarbonylmethoxybenzene (1 g) in dichloromethane (10 ml) was added BBr$_3$ (0.45 ml). After 1 hour, the solvent was evaporated in vacuo and the residue was dissolved in ethyl acetate. The organic layer was washed with NaHCO$_3$ and brine. The dried solvent was evaporated in vacuo to give 3-bromomethyl-1-ethoxycarbonylmethoxybenzene (0.76 g).

NMR (CDCl$_3$, δ): 1.29 (3H, t, J=7 Hz), 4.24 (2H, d, J=7 Hz), 4.61 (2H, s), 5.00 (1H, d, J=3.0 Hz), 5.05 (1H, d, J=3.0 Hz), 6.7–7.1 (3H, m), 7.2–7.3 (1H, m)

Preparation 22

To a solution of (2R)-N-benzyloxycarbonylproline (5 g) in CH$_2$Cl$_2$ (50 ml) were added benzoin (4.5 g), 1-ethyl 3-(3-dimethylaminopropyl)carbodiimide (3.9 ml), and dimethylaminopyridine (2.6 g) at room temperature under N$_2$. After being stirred for 12 hours at room temperature, the solvent was evaporated in vacuo, and the residue was partitioned between ethyl acetate and water. The organic layer was washed with 1N-HCl solution, sat. NaHCO$_3$, and brine, dried over MgSO$_4$, and evaporated in vacuo. The obtained compound and CH$_3$COONH$_4$ (8.2 g) were dissolved in acetic acid (50 ml) and the mixture was stirred for 4 hours at 100° C. After the solvent was removed, the residue was partitioned between ethyl acetate and water. The organic layer was washed with water, sat. NaHCO$_3$ and brine. The dried solvent was evaporated in vacuo and the residue was purified by chromatography on silica gel to give (2R)-1-benzyloxycarbonyl-2-(4,5-diphenyloxazol-2-yl)pyrrolidine (4 g).

MS (m/z): 425 (M$^+$+1)
IR (Neat): 1700 cm$^{-1}$
NMR (CDCl$_3$, δ): 1.8–2.4 (4H, m), 3.4–3.8 (2H, m), 4.8–5.3 (3H, m), 7.0–7.7 (15H, m)

Preparation 23

The following compound was obtained according to a similar manner to that of Preparation 22.
(2S)-1-Benzyloxycarbonyl-2-(4,5-diphenyloxazol-2-yl)pyrrolidine Preparation 24

A mixture of (2R)-1-benzyloxycarbonyl-2-(4,5-diphenyloxazol-2-yl)pyrrolidine (4 g) and 10% Pd/C (0.5 g) in ethanol (120 ml) was stirred under H$_2$ for 10 hours. The catalyst was filtered off and filtrate was evaporated in vacuo to give (2R)-2-(4,5-diphenyloxazol-2-yl)pyrrolidine.

NMR (CDCl$_3$, δ): 1.7–2.3 (4H, m), 2.9–3.2 (2H, m), 3.6–3.8 (1H, m), 4.44 (1H, t, J=6.0 Hz), 7.2–7.7 (10H, m)

Preparation 25

The following compound was obtained according to a similar manner to that of Preparation 24.
(2S)-2-(4,5-Diphenyloxazol-2-yl)pyrrolidine Preparation 26

To a solution of cyclooctanone (4.0 g) in THF (40 ml) was added LDA (23 ml, 1.5M solution in cyclohexane) at −78° C. under N$_2$, and then after 30 minutes, a solution of m-anisaldehyde (4.1 g) in THF (10 ml) was added in the solution. After being stirred for 2 hours at the same temperature, the solution was poured into the mixture of ethyl acetate and water. The organic layer was washed with 1N-HCl solution, sat. NaHCO$_3$, and brine, dried over MgSO$_4$, and evaporated in vacuo. The residue was purified by chromatography on silica gel to afford 2-{hydroxy-(3-methoxyphenyl)methyl}cyclooctanone (6.9 g).

MS (m/z): 245 (M$^+$−17)
IR (Neat): 3400, 1690 cm$^{-1}$
NMR (CDCl$_3$, δ): 1.0–2.3 (10H, m), 2.8–3.2 (2H, m), 3.3–3.6 (1H, m), 3.79 (3H, s), 4.8–5.0 (1H, m), 6.7–7.0 (3H, m), 7.1–7.3 (1H, m)

Preparation 27

A mixture of 2-{hydroxy-(3-methoxyphenyl)methyl}-cyclooctanone (6.0 g) and 10% Pd/C (2 g) in ethanol (120 ml) was stirred under H$_2$ for 10 hours. The catalyst was filtered off and filtrate was evaporated in vacuo. The residue was purified by chromatography on silica gel to give 2-(3-methoxybenzyl)cyclooctanone (2.4 g).

MS (m/z): 247 (M$^+$+1)
IR (Neat): 1700 cm$^{-1}$
NMR (CDCl$_3$, δ): 1.0–2.4 (12H, m), 2.4–2.6 (1H, m), 2.8–3.0 (2H, m), 3.77 (3H, s), 6.6–6.8 (3H, m), 7.17 (1H, t, J=8 Hz)

Preparation 28

To a solution of 4,5-diphenyloxazole (2.1 g) in THF (30 ml) at −78° C. under N$_2$ was added butyllithium (1.6M in hexane, 6.7 ml). After 30 minutes, a solution of 2-(3-methoxybenzyl)cyclooctanone (2.4 g) in THF (10 ml) was added thereto and stirred for 1 hour at the same temperature. The reaction mixture was poured into the mixture of ethyl acetate and water. The organic layer was washed with 1N-HCl solution, sat. NaHCO$_3$, and brine, dried over MgSO$_4$, and evaporated in vacuo. The residue was purified by chromatography on silica gel to afford 1-(hydroxy)-1-(4,5-diphenyloxazol-2-yl)-2-(3-methoxybenzyl)cyclooctane (3.7 g).

MS (m/z): 468 (M$^+$+1)
IR (Neat): 3400 cm$^{-1}$
NMR (CDCl$_3$, δ): 1.2–2.0 (12H, m), 2.2–2.8 (3H, m), 3.38 (1H, s), 3.66 (3H, s), 6.5–6.8 (3H, m), 7.07 (1H, t, J=8 Hz), 7.3–7.8 (10H, m)

Preparation 29

A mixture of 1-(hydroxy)-1-(4,5-diphenyloxazol-2-yl)-2-(3-methoxybenzyl)cyclooctane (3.5 g) and p-toluenesulfonic acid (500 mg) in toluene (50 ml) was stirred for 4 hours under reflux. The solution was washed with water, sat. NaHCO$_3$, and brine, dried over MgSO$_4$, and evaporated in vacuo. The residue was purified by chromatography on silica gel to afford 1-(4,5-diphenyloxazol-2-yl)-8-(3-methoxybenzyl)-1-cyclooctene (3.8 g).

MS (m/z): 450 (M$^+$+1)
IR (Neat): 1600 cm$^{-1}$
NMR (CDCl$_3$, δ): 1.4–2.0 (8H, m), 2.2–2.4 (2H, m), 3.0 (1H, m), 3.2–3.5 (2H, m), 3.78 (3H, s), 6.65 (1H, s), 6.7–7.0 (3H, m), 7.18 (1H, t, J=8 Hz), 7.2–7.8 (11H, m)

Preparation 30

The following compound was obtained according to a similar manner to that of Preparation 26.
2-Oxo-3-[hydroxy(3-methoxyphenyl)methyl]bicyclo[2.2.1]-heptane MS (m/z): 229 (M$^+$−17)
IR (Neat): 3400, 1720 cm$^{-1}$
NMR (CDCl$_3$, δ): 1.2–2.2 (9H, m), 2.5–2.7 (1H, m), 3.81 (3H, s), 4.58 (1H, d, J=10 Hz), 6.7–7.0 (3H, m), 7.26 (1H, t, J=8 Hz)

Preparation 31

The following compound was obtained according to a similar manner to that of Preparation 27.
2-Oxo-3-(3-methoxybenzyl)bicyclo[2.2.1]heptane MS (m/z): 231 (M$^+$+1)
IR (Neat): 1740 cm$^{-1}$
NMR (CDCl$_3$, δ): 1.2–2.0 (7H, m), 2.3–2.5 (2H, m), 2.6 (1H, m), 2.8–3.0 (1H, m), 3.79 (3H, s), 6.7–6.8 (3H, m), 7.21 (1H, t, J=8 Hz)

Preparation 32

2-(Hydroxy)-2-(4,5-diphenyloxazol-2-yl)-3-(3-methoxybenzyl)bicyclo[2.2.1]heptane was obtained according to a similar manner to that of Preparation 28.

MS (m/z): 452 (M⁺+1)
IR (Neat): 3400 cm⁻¹
NMR (CDCl₃, δ): 1.2–1.8 (7H, m), 2.0–2.6 (4H, m), 3.59 (1H, s), 3.68 (3H, s), 6.5–6.8 (3H, m), 7.08 (1H, t, J=8 Hz), 7.3–7.8 (10H, m)

Preparation 33
2-(4,5-Diphenyloxazol-2-yl)-3-(3-methoxybenzyl) bicyclo[2.2.1]hept-2-ene was obtained according to a similar manner to that of Preparation 29.
MS (m/z): 434 (M⁺+1)
IR (Neat): 1600 cm⁻¹
NMR (CDCl₃, δ): 1.0–2.0 (6H, m), 2.87 (1H, br s), 3.61 (1H, br s), 3.76 (3H, s), 3.79 (1H, d, J=16 Hz), 4.30 (1H, J=16 Hz), 6.6–7.0 (3H, m), 7.1–7.8 (11H, m)

Preparation 34
To a solution of 2-(1,4-dihydroxybutyl)-4,5-diphenyloxazole (1 g) in tetrahydrofuran (10 ml) were added methanesulfonyl chloride (1.6 g) and triethylamine (1.5 ml) at 0° C. The solution was diluted with ethyl acetate and washed with sat. NaHCO₃ and brine, dried over MgSO₄, and evaporated. The residue was dissolved in benzylamine (10 ml). After being stirred for 2 hours at 80° C., the mixture was partitioned between ether and water. The or-ganic layer was washed with water and brine. The dried solvent was evaporated in vacuo and the residue was purified by chromatography on silica gel to afford 1-benzyl-2-(4,5-diphenyloxazol-2-yl)pyrrolidine (1.3 g).
MS (m/z): 381 (M⁺+1)
IR (Neat): 1600 cm⁻¹
NMR (CDCl₃, δ): 1.8–2.6 (5H, m), 3.0–3.2 (1H, m), 3.60 (1H, d, J=13 Hz), 3.85 (1H, t, J=7.8 Hz), 3.89 (1H, d, J=13 Hz), 7.0–7.8 (15H, m)

Preparation 35
A mixture of 1-benzyl-2-(4,5-diphenyloxazol-2-yl) pyrrolidine (1.3 g) and 10% Pd/C (2 g) in ethanol (120 ml) was stirred under H₂ for 10 hours. The catalyst was filtered off and filtrate was evaporated in vacuo. The residue was dissolved in dichloromethane (20 ml) and 1-ethyl-3-(3-dimethylaminopropyl)carbodiimide (0.31 ml) and dimethylaminopyridine (0.21 g) were added to the solution at room temperature under N₂. After being stirred for 12 hours at room temperature, the solvent was evaporated in vacuo, and the residue was partitioned between ethyl acetate and water. The organic layer was washed with 1N-HCl solution, sat. NaHCO₃, and brine, dried over MgSO₄, and evaporated in vacuo. The residue was purified by chromatography on silica gel to give 2-(4,5-diphenyloxazol-2-yl)-1-(3-methoxyphenylcarbonyl)-pyrrolidine (0.57 g).
MS (m/z): 425 (M⁺+1)
IR (Neat): 1630 cm⁻¹
NMR (CDCl₃, δ) 1.8–2.4 (4H, m), 3.4–4.0 (6H, m), 6.6–7.0 (3H, m), 7.0–7.8 (11H, m)

Preparation 36
2-(2-Methoxybenzyl)cyclohexanone was obtained according to similar manners to those of Preparations 26 and 27.
MS (m/z): 219 (M⁺+1)
IR (Neat): 1700 cm⁻¹
NMR (CDCl₃, δ): 1.2–2.2 (6H, m), 2.2–2.6 (4H, m), 3.22 (1H, dd, J=4.4, 13.2 Hz), 3.79 (3H, s), 6.7–7.2 (3H, m)

Preparation 37
1-(4,5-Diphenyloxazol-2-yl)-6-(2-methoxybenzyl)-1-cyclohexene was obtained according to similar manners to those of Preparations 28 and 29.
MS (m/z): 422 (M⁺+1)
IR (Neat): 1600 cm⁻¹
NMR (CDCl₃, δ): 1.2–2.0 (4H, m), 2.2–2.4 (2H, m), 2.9 (1H, m), 3.1–3.4 (2H, m), 3.77 (3H, s), 6.7–6.9 (3H, m), 7.09 (1H, t, J=8 Hz), 7.2–7.8 (11H, m)

Preparation 38
1-(4,5-Diphenyloxazol-2-yl)-6-(4-methoxybenzyl)-1-cyclohexene was obtained according to similar manners to those of Preparations 28 and 29.
MS (m/z): 422 (M⁺+1)
IR (Neat): 1600 cm⁻¹
NMR (CDCl₃, δ): 1.4–2.0 (4H, m), 2.3–2.4 (2H, m), 2.44 (1H, m), 3.1–3.3 (2H, m), 3.74 (3H, s), 6.7–6.9 (3H, m), 7.1–7.8 (12H, m)

Preparation 39
1-(4,5-Diphenyloxazol-2-yl)-6-(4-hydroxybenzyl)-1-cyclohexene was obtained according to a similar manner to that of the first step of Example 24.
MS (m/z): 408 (M⁺+1)
IR (Neat): 3300 cm⁻¹
NMR (CDCl₃, δ): 1.4–2.0 (4H, m), 2.3–2.6 (3H, m), 3.0–3.3 (2H, m), 6.70 (2H, d, J=8.0 Hz), 6.90 (1H, m), 7.15 (2H, d, J=8.0 Hz), 7.2–7.8 (10H, m)

Preparation 40
2-(3-Methoxy-6-methylbenzyl)cyclohexanone was obtained according to similar manners to those of Preparations 26 and 27.
MS (m/z): 233 (M⁺+1)
IR (Neat): 1700 cm⁻¹
NMR (CDCl₃, δ): 1.2–2.6 (10H, m), 2.20 (3H, s), 3.22 (1H, dd, J=4.0, 14.0 Hz), 3.76 (3H, s), 6.6–6.8 (2H, m), 7.03 (1H, d, J=8.0 Hz)

Preparation 41
2-(3-Methoxy-4-methylbenzyl)cyclohexanone was obtained according to similar manners to those of Preparations 26 and 27.
MS (m/z): 233 (M⁺+1)
IR (Neat): 1700 cm⁻¹
NMR (CDCl₃, δ) 1.2–2.6 (10H, m), 2.17 (3H, s), 3.20 (1H, dd, J=4.0, 14.0 Hz), 3.78 (3H, s), 6.5–6.7 (2H, m), 6.99 (1H, d, J=8.0 Hz)

Preparation 42
2-(3-Methoxy-2-methylbenzyl)cyclohexanone was obtained according to similar manners to those of Preparations 26 and 27.
MS (m/z): 233 (M⁺+1)
IR (Neat): 1700 cm⁻¹
NMR (CDCl₃, δ): 1.2–2.6 (10H, m), 2.17 (3H, s), 3.2–3.4 (1H, m), 3.79 (3H, s), 6.72 (2H, d, J=8.0 Hz), 7.01 (1H, t, J=8.0 Hz)

Preparation 43
The following compounds were obtained according to similar manners to those of Preparations 28 and 29.
(1) 1-(4,5-Diphenyloxazol-2-yl)-6-(3-methoxy-6-methylbenzyl)-1-cyclohexene
MS (m/z): 436 (M⁺+1)
IR (Neat): 1600 cm⁻¹
NMR (CDCl₃, δ): 1.4–2.4 (6H, m), 2.41 (3H, s), 2.5–2.8 (1H, m), 3.1–3.4 (2H, m), 3.74 (3H, s), 6.6–6.9 (3H, m), 7.04 (1H, t, J=8 Hz), 7.2–7.8 (10H, m)
(2) 1-(4,5-Diphenyloxazol-2-yl)-6-(3-methoxy-4-methylbenzyl)-1-cyclohexene
MS (m/z) 436 (M⁺+1)
IR (Neat): 1600 cm⁻¹
NMR (CDCl₃, δ) 1.4–2.4 (6H, m), 2.17 (3H, s), 2.51 (1H, dd, J=10.0, 12.0 Hz), 3.1–3.3 (2H, m), 3.78 (3H, s), 6.7–7.1 (4H, m), 7.2–7.8 (10H, m)
(3) 1-(4,5-Diphenyloxazol-2-yl)-6-(3-methoxy-2-methylbenzyl)-1-cyclohexene
MS (m/z): 436 (M⁺+1)
IR (Neat): 1600 cm⁻¹
NMR (CDCl₃, δ) 1.4–2.4 (6H, m), 2.41 (3H, s), 2.5–2.8 (1H, m), 3.1–3.4 (2H, m), 3.74 (3H, s), 6.6–7.1 (4H, m), 7.2–7.8 (10H, m)

Preparation 44

The following compounds were obtained according to a similar manner to that of the first step of Example 24.

(1) 1-(4,5-Diphenyloxazol-2-yl)-6-(3-hydroxy-6-methylbenzyl)-1-cyclohexene

MS (m/z) 422 (M$^+$+1)

IR (Neat): 3400 cm$^{-1}$

NMR (CDCl$_3$, δ): 1.4–2.4 (6H, m), 2.37 (3H, s), 2.58 (1H, dd, J=10.0, 13.6 Hz), 3.1–3.3 (2H, m), 6.6–7.0 (4H, m), 7.2–7.8 (10H, m)

(2) 1-(4,5-Diphenyloxazol-2-yl)-6-(3-hydroxy-4-methylbenzyl)-1-cyclohexene

MS (m/z): 422 (M$^+$+1)

IR (Neat): 3400 cm$^{-1}$

NMR (CDCl$_3$, δ): 1.4–2.4 (6H, m), 2.22 (3H, s), 2.46 (1H, dd, J=10.0, 12.0 Hz), 3.1–3.3 (2H, m), 6.6–7.0 (4H, m), 7.2–7.8 (10H, m)

(3) 1-(4,5-Diphenyloxazol-2-yl)-6-(3-hydroxy-2-methylbenzyl)-1-cyclohexene

MS (m/z): 422 (M$^+$+1)

IR (Neat): 3400 cm$^{-1}$

NMR (CDCl$_3$, δ) 1.4–2.4 (6H, m), 2.44 (3H, s), 2.61 (1H, dd, J=4.0, 13.0 Hz), 3.1–3.4 (2H, m), 6.62 (1H, d, J=8 Hz), 6.81 (1H, d, J=8.0 Hz), 6.9–7.1 (2H, m), 7.2–7.8 (10H, m)

Preparation 45

(1) 2-[3-(2-Ethoxycarbonylethyl)benzyl]cyclohexanone was obtained from 2-[3-(2-ethoxycarbonylvinyl)benzyl]cyclohexanone [which was obtained according to similar manners to those of Preparations 26 and 27] in a similar manner to that of Preparation 24.

MS (m/z): 289 (M$^+$+1)

IR (Neat): 1720, 1700 cm$^{-1}$

NMR (CDCl$_3$, δ): 1.22 (3H, t, J=7 Hz), 1.3–2.7 (14H, m), 2.92 (2H, t, J=8 Hz), 3.20 (1H, dd, J=5.6, 10.6 Hz), 4.12 (2H, q, J=8 Hz), 6.9–7.1 (2H, m), 7.20 (1H, t, J=8 Hz)

(2) 2-(3-Methoxy-6-phenylbenzyl)cyclohexanone was obtained according to similar manners to those of Preparations 26 and 27.

MS (m/z): 295 (M$^+$+1)

IR (Neat): 1700 cm$^{-1}$

NMR (CDCl$_3$, δ) 1.0–2.6 (10H, m), 3.20 (1H, dd, J=5.0, 9.8 Hz), 3.78 (3H, s), 6.6–6.8 (2H, m), 7.1–7.5 (5H, m)

Preparation 46

1-(4,5-Diphenyloxazol-2-yl)-6-(3-methoxy-6-phenylbenzyl)-1-cyclohexene was obtained according to similar manners to those of Preparations 28 and 29.

MS (m/z): 498 (M$^+$+1)

IR (Neat): 1600 cm$^{-1}$

NMR (CDCl$_3$, δ): 1.2–2.0 (4H, m), 2.0–2.2 (2H, m), 2.80 (1H, dd, J=11.2, 14.0 Hz), 3.1–3.4 (2H, m), 3.80 (3H, s), 6.6–6.9 (3H, m), 7.1–7.5 (12H, m), 7.6–7.8 (4H, m)

Preparation 47

To a solution of 2-(4,5-diphenyloxazol-2-yl)pyrrolidine (0.6 g) and 5-tert-butyldiphenylsilyloxy-2-oxo-1,2,3,4-tetrahydronaphthalene (0.5 g) in a mixture of methanol (10 ml) and acetic acid (2 ml) was added NaBH$_3$CN (250 mg) at room temperature. After being stirred for 2 hours at the same temperature, the mixture was poured into the mixture of ethyl acetate and water. The organic layer was washed with water and brine, dried over MgSO$_4$, and evaporated in vacuo. The residue was purified by chromatography on silica gel to afford 2-[2-(4,5-diphenyloxazol-2-yl)pyrrolidin-1-yl]-5-tert-butyldiphenylsilyloxy-1,2,3,4-tetrahydronaphthalen (0.84 g).

MS (m/z): 676 (M$^{+)}$

IR (Neat): 1580 cm$^{-1}$

NMR (CDCl$_3$, δ): 1.08 (9H, s), 1.5–2.4 (6H, m), 2.6–3.3 (6H, m), 4.42 (1H, m), 6.10 (1H, m), 6.4–6.7 (2H, m), 7.2–7.8 (20H, m)

Preparation 48

To a solution of 2-(4,5-diphenyloxazol-2-yl)pyrrolidine (0.66 g) and 5-tert-butyldiphenylsilyloxy-1,2-epoxy-1,2,3,4-tetrahydronaphthalene (0.6 g) in tetrahydrofuran (10 ml) was added Ti[O—CH(CH$_3$)$_2$]$_4$ (0.66 ml) at room temperature. After being stirred for 5 days at the same temperature, the mixture was poured into the mixture of ethyl acetate and water. The organic layer was washed with water and brine, dried over MgSO$_4$, and evaporated in vacuo. The residue was purified by chromatography on silica gel to afford 1-[2-(4,5-diphenyloxazol-2-yl)pyrrolidin-1-yl]-2-hydroxy-5-tert-butyldiphenylsilyloxy-1,2,3,4-tetrahydronaphthalene (0.31 g).

MS (m/z): 691 (M$^+$)

IR (Neat): 3300 cm$^{-1}$

NMR (CDCl$_3$, δ): 1.07 (9H, s), 1.7–2.4 (6H, m), 2.6–3.3 (2H, m), 3.4–3.6 (2H, m), 4.1–4.4 (2H, m), 6.28 (1H, d, J=8.0 Hz), 6.75 (1H, t, J=8.0 Hz), 6.88 (1H, d, J=8.0 Hz), 7.3–7.8 (20H, m)

Preparation 49

1-(2-Oxotetrahydrofuran-3-yl)-5-tert-butyldiphenylsilyloxy-3,4-dihydronaphthalene was obtained according to similar manners to those of Preparations 28 and 29.

MS (m/z): 469 (M$^+$+1)

IR (Neat): 1760 cm$^{-1}$

NMR (CDCl$_3$, δ): 1.10 (9H, s), 2.1–2.8 (4H, m), 2.8–3.1 (2H, m), 3.73 (1H, m), 4.3–4.4 (2H, m), 6.04 (1H, m), 6.37 (1H, d, J=8 Hz), 6.5–6.9 (2H, m), 7.2–7.8 (10H, m)

Preparation 50

1-[2-(4,5-Diphenyloxazol-2-yl)-2-oxo-1-(2-hydroxyethyl)ethyl]-5-tert-butyldiphenylsilyloxy-3,4-dihydronaphthalene was obtained from 1-(2-oxotetrahydrofuran-3-yl)-5-tert-butyldiphenylsilyloxy-3,4-dihydronaphthalene in a conventional manner.

MS (m/z): 690 (M$^+$+1)

IR (Neat): 3400, 1700 cm$^{-1}$

NMR (CDCl$_3$, δ): 1.07 (9H, s), 2.0–2.5 (4H, m), 2.90 (2H, t, J=8.0 Hz), 3.71 (2H, t, J=6.0 Hz), 5.0–5.2 (1H, m), 6.06 (1H, t, J=4.6 Hz), 6.41 (1H, d, J=8.0 Hz), 6.83 (1H, t, J=8.0 Hz), 7.2–7.8 (21H, m)

Preparation 51

1-[2-(4,5-Diphenyloxazol-2-yl)-2-hydroxy-1-(2-hydroxyethyl)ethyl]-5-tert-butyldiphenylsilyloxy-3,4-dihydronaphthalene was obtained by treating 1-[2-(4,5-diphenyloxazol-2-yl)-2-oxo-1-(2-hydroxyethyl)ethyl]-5-tert-butyldiphenylsilyloxy-3,4-dihydronaphthalene with NaBH$_4$.

MS (m/z): 692 (M$^+$+1)

IR (Neat): 3300 cm$^{-1}$

NMR (CDCl$_3$, δ) 1.07 (9H, s), 2.0–2.5 (4H, m), 2.7–3.2 (2H, m), 3.6–3.9 (3H, m), 5.03 (1H, d, J=3.8 Hz), 6.01 (1H, t, J=4.6 Hz), 6.22 (1H, d, J=8.0 Hz), 6.55 (1H, t, J=8.0 Hz), 6.82 (1H, d, J=8 Hz), 7.2–7.8 (20H, m)

Preparation 52

To a solution of 1-[2-(4,5-diphenyloxazol-2-yl)-2-hydroxy-1-(2-hydroxyethyl)ethyl]-5-tert-butyldiphenylsilyloxy-3,4-dihydronaphthalene (1.5 g) in tetrahydrofuran (30 ml) were added triphenylphosphine (1.8 g) and diethyl azodiformate (1.2 ml) at room temperature. After being stirred for 12 hours at the same temperature, the mixture was poured into the mixture of ethyl acetate and water. The organic layer was washed with water and brine, dried over MgSO$_4$, and evaporated in vacuo. The residue was purified by chromatography on silica gel to afford 1-[2-(4,5-diphenyloxazol-2-yl)tetrahydrofuran-3-yl]-5-tert-butyldiphenylsilyloxy-3,4-dihydronaphthalene (1.0 g).

MS (m/z): 674 (M⁺+1)
IR (Neat): 1580 cm⁻¹
NMR (CDCl₃, δ): 1.07 (9H, s), 2.0–2.4 (3H, m), 2.6–3.1 (2H, m), 3.8–4.5 (4H, m), 5.47 (1H, d, J=8.0 Hz), 5.93 (1H, m), 6.39 (1H, d, J=8.0 Hz), 6.82 (1H, t, J=8.0 Hz), 7.02 (1H, d, J=8 Hz), 7.2–7.8 (10H, m)

Preparation 53

A mixture of 1-azido-5-t-butyldiphenylsilyloxy-1,2,3,4-tetrahydronaphthalene (2.2 g) and 10% Pd/C (0.5 g) in ethanol (120 ml) was stirred under H₂ for 5 hours. The catalyst was filtered off and filtrate was evaporated in vacuo. The obtained oil and 2-formyl-4,5-diphenyloxazole (1.2 g) was dissolved in toluene (20 ml). After stirred for 12 hours at room temperature, the solvent was removed to obtain the imine compound. To a solution of ethyl acetate (1.1 ml) in THF (20 ml) was added LDA (7.4 ml, 1.5M solution in cyclohexane) at −78° C. under N₂, and then after 30 minutes, a solution of the above imine (1.0 g) in THF (10 ml) was added in the solution. After being stirred for 2 hours at the same temperature, the solution was allowed to the room temperature for 4 hours and poured into the mixture of ethyl acetate and water. The organic layer was washed with 1N-HCl solution, sat. NaHCO₃, and brine, dried over MgSO₄, and evaporated in vacuo. The residue was purified by chromatography on silica gel to afford 1-[4-(4,5-diphenyloxazol-2-yl)-2-oxoazetidin-1-yl]-5-t-butyldiphenylsilyloxy-1,2,3,4-tetrahydronaphthalene (420 mg).

MS (m/z): 765 (M⁺)
IR (Neat): 1740 cm⁻¹
NMR (CDCl₃, δ): 1.05 (9H, s), 1.8–2.9 (4H, m), 3.3–3.6 (2H, m), 4.0–4.3(2H, m), 4.6–5.2 (2H, m), 6.0–6.4 (1H, m), 6.8–7.0 (1H, m), 7.1–7.8 (21H, m)

Preparation 54

The following compounds were obtained according to a similar manner to that of Preparation 5 (2).

(1) 1-[2-(4,5-Diphenyloxazol-2-yl)azetidin-1-yl]-5-t-butyldiphenylsilyloxy-1,2,3,4-tetrahydronaphthalene MS (m/z): 661 (M⁺)
NMR (CDCl₃, δ): 1.04 (9H, s), 1.6–3.0 (8H, m), 3.3–3.8 (3H, m), 4.4–4.7 (1H, m), 6.2–6.9 (2H, m), 7.1-7.8 (21H, m)

(2) 1-[2-(4,5-Diphenyloxazol-2-yl)piperidin-1-yl]-5-t-butyldiphenylsilyloxy-1,2,3,4-tetrahydronaphthalene MS (m/z): 689 (M⁺)
IR (Neat): 1580 cm⁻¹
NMR (CDCl₃, δ) 1.06 (9H, s), 1.4–2.4 (10H, m), 2.5–3.1 (4H, m), 3.50–4.2 (2H, m), 6.15, 6.25 (1H, each d, J=8 Hz), 6.53, 6.76 (1H, each d, J=8 Hz), 7.1–7.8 (21H, m)

Preparation 55

2-Vinyl-4,5-diphenyloxazole was obtained according to a similar manner to that of Preparation 10.

MS (m/z): 248 (M⁺+1)
IR (Neat): 1460 cm⁻¹
NMR (CDCl₃, δ): 5.65 (1H, d, J=11.2 Hz), 6.25 (1H, d, J=17.6 Hz), 6.67 (1H, dd, J=11.2, 17.6 Hz), 7.2–7.7 (10H, m)

Preparation 56

A solution of AD-mix-β (trade name, Aldrich) (114 g) in a mixture of t-butyl alcohol (400 ml) and water (400 ml) was stirred for 1 hour, and then methanesulfonamide (7.6 g) and 2-vinyl-4,5-diphenyloxazole (20 g) was added to the solution at 0° C. After being stirred for 8 hours at the same temperature, sodium sulfite (50 g) was added, and the mixture was stirred for 30 minutes. The mixture was partitioned between ethyl acetate and water. The organic layer was washed with 1N-HCl solution, sat. NaHCO₃, and brine, dried over MgSO₄, and evaporated in vacuo. The residue was purified by trituration with hexane-ether to afford 2-((1S)-1,2-dihydroxyethyl)-4,5-diphenyloxazole (21 g).

MS (m/z): 282 (M⁺+1)
IR (Neat): 3400 cm⁻¹
NMR (CDCl₃, δ): 4.03 (1H, d, J=4.6 Hz), 4.90 (1H, t, J=4.6 Hz), 7.2–7.6 (10H, m)

Preparation 57

To a solution of 2-((1S)-1,2-dihydroxyethyl)-4,5-diphenyloxazole (20 g) in CH₂Cl₂ (400 ml) were added orthoacetic acid trimethyl ester (12.8 ml) and p-toluenesulfonic acid (130 mg) at room temperature under N₂. After being stirred for 30 minutes, the solvent was evaporated in vacuo. The residue was diluted with CH₂Cl₂ (200 ml) and acetyl bromide (7.6 ml) was added to the solution at 0° C. under N₂. After being stirred for 2 hours at room temperature, the solvent was evaporated in vacuo, the residue was diluted with methanol (200 ml), and K₂CO₃ (16 g) was added to the solution at 0° C. The mixture was stirred for 30 minutes at the same temperature and partitioned between ethyl acetate and water. The organic layer was washed with 1N-HCl, water, sat. NaHCO₃ and brine. The dried solvent was evaporated in vacuo and the residue was purified by trituration with ether-hexane to give (2S)-2-(4,5-diphenyloxazol-2-yl)oxirane (14.2 g).

MS (m/z): 264 (M⁺+1)
IR (Neat): 1460 cm⁻¹
NMR (CDCl₃, δ): 3.23 (1H, dd, J=4.0, 5.6 Hz), 3.43 (1H, dd, J=2.6, 5.6 Hz), 4.08 (1H, dd, J=2.6, 4.0 Hz), 7.2–7.6 (10H, m)
HPLC; chiralcel OD, 10% isopropanol/hexane, 11.3 ml/min Preparation 58

To a solution of (2S)-2-(4,5-diphenyloxazol-2-yl)oxirane (12 g) and CuI (0.19 g) in THF (240 ml) was dropwise added a solution of vinylmagnesium chloride in THF (1.0M solution, 101 ml) at −78° C. under N₂. The mixture was stirred for 1 hour at room temperature and partitioned between ethyl acetate and water. The organic layer was washed with 1N-HCl, water, sat. NaHCO₃ and brine. The dried solvent was evaporated in vacuo and the residue was purified by chromatography on silica gel to give (4S)-4-(4,5-diphenyloxazol-2-yl)-4-hydroxy-1-butene (9.2 g).

MS (m/z): 292 (M⁺+1)
IR (Nujol): 3300, 1600 cm⁻¹
NMR (CDCl₃, δ): 2.7–2.9 (2H, m), 3.17 (1H, d, J=5.8 Hz), 4.8–5.0 (1H, m), 5.1–5.3 (2H, m), 5.8–6.0 (1H, m), 7.2–7.8 (10H, m)

Preparation 59

To a solution of (4S)-4-(4,5-diphenyloxazol-2-yl)-4-hydroxy-1-butene (9.2 g) in THF (100 ml) were added phthalimide (7.0 g) and triphenylphosphine (12.5 g) and diethyl azodiformate (7.5 ml) at room temperature. The mixture was stirred for 2 hours at room temperature and partitioned between ethyl acetate and water. The organic layer was washed with 1N-HCl, water, sat. NaHCO₃ and brine. The dried solvent was evaporated in vacuo and the residue was purified by chromatography on silica gel to give (4R)-4-(4,5-diphenyloxazol-2-yl)-4-phthalimido-1-butene (9.7 g).

MS (m/z): 421 (M⁺+1)
IR (Nujol): 1760, 1710 cm⁻¹
NMR (CDCl₃, δ): 3.1–3.4 (2H, m), 5.0–5.3 (2H, m), 5.63 (1H, dd, J=6.0, 10.0 Hz), 5.7–6.0 (1H, m), 7.2–8.0 (14H, m)
HPLC; chiralcel OD, 10% isopropanol/hexane, 32.2 ml/min Preparation 60

(4R)-4-(4,5-Diphenyloxazol-2-yl)-4-benzyloxycarbonylamino-1-butene was obtained according to similar manners to those of Preparations 82 and 103.

MS (m/z): 425 (M$^+$+1)
IR (Nujol): 3300, 1710 cm$^{-1}$
NMR (CDCl$_3$, δ): 2.75 (1H, m), 5.0–5.3 (5H, m), 5.5–6.0 (2H, m), 7.2–7.7 (15H, m)
HPLC; chiralcel OD, 5% isopropanol/hexane, 12.9 ml/min Preparation 61

To a solution of (4R)-4-(4,5-diphenyloxazol-2-yl)-4-benzyloxycarbonylamino-1-butene (5.2 g) in THF (50 ml) was added 9-borabicyclo(3.3.1]nonane (9-BBN) (98 ml, 0.5M solution of THF) at 0° C. After stirred for 4 hours at room temperature, 2N NaOH solution (20 ml) and 35% H$_2$O$_2$ solution (20 ml) were added to the mixture at the 0° C. The mixture was stirred for 1 hour at the same temperature and partitioned between ethyl acetate and water. The organic layer was washed with 1N-HCl, water, sat. NaHCO$_3$ and brine. The dried solvent was evaporated in vacuo and the residue was purified by chromatogaphy on silica gel to give (1R)-N-benzyloxycarbonyl-4-hydroxy-1-(4,5-diphenyloxazol-2-yl)butylamine (13 g).
MS (m/z): 443 (M$^+$+1)
IR (Neat): 3300, 1700 cm$^{-1}$
NMR (CDCl$_3$, δ): 1.6–2.2 (4H, m), 3.68 (2H, m), 5.10–5.2 (1H, m), 5.14 (2H, s), 5.73 (1H, d, J=10.0 Hz), 7.2–7.7 (15H, m)

Preparation 62

A suspension of methyl 3-hydroxybenzoate (25.0 g), benzyl bromide (19.5 ml), and K$_2$CO$_3$ (31.73 g) in N,N-dimethylformamide (150 ml) was stirred under ice cooling for 1 hour and at room temperature for 15 hours and partitioned between water and ethyl acetate. The organic layer was separated, washed with water (three times) and brine, dried over MgSO$_4$, and evaporated in vacuo. The residue was chromatographed over silica gel to methyl 3-benzyloxybenzoate (38.90 g) as colorless crystals.
(+) APCI-MS (m/z): 243 (M$^+$+1)
mp: 72.3–75.1° C.
IR (Nujol): 1710, 1235 cm$^{-1}$
NMR (CDCl$_3$, δ) 3.91 (3H, s), 5.10 (2H, s), 7.17–7.67 (9H, m)

Preparation 63

A solution of methyl 3-benzyloxybenzoate (38.0 g) and 5N NaOH solution (207 ml) in 1,2-dimethoxyethane (207 ml) was stirred at room temperature for 3 hours 30 minutes and at 100° C. for 1 hour 20 minutes. The reaction mixture was cooled with ice water, mixed with 6N HCl (1.1 mole), and extracted with diethyl ether. The extract was washed with brine, dried over MgSO$_4$, and evaporated in vacuo to afford 3-benzyloxybenzoic acid (34.96 g) as a colorless powder.
(−) APCI-MS (m/z): 227 (M$^+$−1)
mp: 134.1–135.8° C.
IR (Nujol): 2700–2150, 1680, 1250 cm$^{-1}$
NMR (CDCl$_3$, δ): 5.12 (2H, s), 7.19–7.49 (7H, m), 7.71–7.76 (2H, m)

Preparation 64

Triethylamine (3.36 ml) was added to a stirred solution of 3-benzyloxybenzoic acid (5.0 g) and isobutyl chloroformate (3.13 ml) in THF (67 ml) under ice-cooling and the resulting mixture was stirred at the same temperature for 1 hour. A solution of 2-piperidinecarboxylic acid (4.14 g) and NaHCO$_3$ (3.32 g) in water (40 ml) was added dropwise to the stirred mixture at the same temperature and the mixture was stirred at the same temperature for 2 hours and at room temperature overnight. The reaction mixture was partitioned between ethyl acetate and 1N HCl. The organic layer was separated, washed with 1N HCl (twice) and brine, dried over MgSO$_4$, and evaporated in vacuo. The residue was chromatographed over silica gel to afford 1-(3-benzyloxybenzoyl)-2-piperidinecarboxylic acid (2.01 g) as a amorphous powder.
(+) APCI-MS (m/z): 340 (M$^+$+1)
IR (Nujol): 2590, 1710, 1595, 1575, 1230 cm$^{-1}$ Preparation 65

Sodium (54 mg) was dissolved in ethanol (8.0 ml), and then 1-(3-benzyloxybenzoyl)-2-piperidinecarboxylic acid (665 mg), conc. sulfuric acid (1 drop), and desyl bromide (539 mg) was successively dissolved thereto. The resulting mixture was stirred at 70° C. for 2 days, cooled to room temperature, and partitioned between ethyl acetate and 1N HCl. The organic layer was washed with 1N HCl, aqueous sodium bicarbonate, and brine, dried over MgSO$_4$, and evaporated in vacuo. The residue was chromatographed over silica gel to afford 2-oxo-1,2-diphenylethyl 1-(3-benzyloxybenzoyl)-2-piperidinecarboxylate (297 mg) as a pale yellow oil.
(+) APCI-MS (m/z): 534 (M$^+$+1)
IR (Nujol): 1735, 1690, 1630, 1225 cm$^{-1}$ Preparation 66

A mixture of 2-oxo-1,2-diphenylethyl 1-(3-benzyloxybenzoyl)-2-piperidinecarboxylate (288 mg) and ammonium acetate (427 mg) in acetic acid (1.4 ml) was stirred under reflux for 3 hours, cooled to room temperature, and partitioned between ethyl acetate and aqueous NaHCO$_3$. The organic layer was washed with aqueous NaHCO$_3$ (twice) and brine, dried over MgSO$_4$, and evaporated in vacuo. The residue was chromatographed over silica gel to afford 1-(3-benzyloxybenzoyl)-2-(4,5-diphenyl-2-oxazolyl) piperidine (104 mg) as amorphous powder.
(+) APCI-MS (m/z): 515 (M$^+$+1)
IR (Nujol): 1630 cm$^{-1}$
NMR (CDCl$_3$, δ): 1.45–2.05 (6H, m), 2.4–3.75 (2H, m), 4.7–5.25 (3H, m), 7.01–7.37 (15H, m), 7.57–7.67 (4H, m)

Preparation 67

A mixture of 1-(3-benzyloxybenzoyl)-2-(4,5-diphenyl-2-oxazolyl)piperidine (95 mg) and 10% Pd—C (50% wet, 15 mg) in ethyl acetate (3 ml)—10% methanolic hydrogen chloride was stirred in the presence of atmospheric H$_2$ gas at room temperature for 7 hours and filtered. The filtrate was evaporated in vacuo to afford 1-(3-hydroxybenzoyl)-2-(4,5-diphenyl-2-oxazolyl)piperidine (100 mg) as a crude oil.

Preparation 68

A mixture of 3-[3-(tert-butyldiphenylsilyloxy)phenyl]-1-(4,5-diphenyl-2-oxazolyl)-1-propanone (526 mg), ethyl bromoacetate (1.61 g), and K$_2$CO$_3$ (1.34 g) in N,N-dimethylformamide (2.0 ml) was stirred at room temperature for 5 hours and poured into ethyl acetate—water. The organic layer was separated, washed with water (three times) and brine, dried over MgSO$_4$, and evaporated in vacuo. The residue was chromatographed over silica gel to afford ethyl 3-[3-(tert-butyldiphenylsilyloxy)benzyl]-4-(4,5-diphenyl-2-oxazolyl)-4-oxobutyrate (436 mg) as an oil.
(+) APCI-MS (m/z): 694 (M$^+$+1)
IR (Nujol): 1740, 1700, 1600, 1580 cm$^{-1}$ Preparation 69

NaBH$_4$ (119 mg) was added to a stirred solution of ethyl 3-[3-(tert-butyldiphenylsilyloxy)benzyl]-4-(4,5-diphenyl-2-oxazolyl)-4-oxobutyrate (430 mg) in methanol (2.0 ml) and 1,2-dimethoxyethane (0.5 ml) at room temperature and the resulting mixture was stirred at the same temperature for 3 hours. The reaction mixture was partitioned between ethyl acetate—1N hydrochloric acid. The organic layer was washed with 1N hydrochloric acid, aqueous sodium bicarbonate, and brine, dried over MgSO$_4$, and evaporated in vacuo. The residue was chromatographed over silica gel to afford 3-[3-(tert-butyldiphenylsilyloxy)benzyl]-2-(4,5-diphenyl-2-oxazolyl)-5-oxotetrahydrofuran (366 mg) as an amorphous powder.

NMR (CDCl$_3$, δ) 1.08 and 1.09 (9H, each s), 1.40–1.62 (1H, m), 2.31–2.97 (2H, m), 3.48–3.88 (2H, m), 4.58 and 4.80 (1H, each m), 6.54–7.05 (2H, m), 7.32–7.73 (22H, m)

Preparation 70

A 1.0M solution of tetrabutylammonium fluoride in tetrahydrofuran (THF) (0.75 ml) was added to a solution of 3-[3-(tert-butyldiphenylsilyloxy)benzyl]-2-(4,5-diphenyl-2-oxazolyl)-5-oxotetrahydrofuran (0.26 g) in THF (0.75 ml) at room temperature. The resulting mixture was stirred at the same temperature for 5 hours and partitioned between ethyl acetate and water. The organic layer was separated, washed with brine, dried over MgSO$_4$, and evaporated in vacuo. The residue was chromatographed over silica gel to afford 2-(4,5-diphenyl-2-oxazolyl)-3-(3-hydroxybenzyl)-5-oxotetrahydrofuran (133 mg) as a colorless oil.

(+) APCI-MS (m/z): 412 (M$^+$+1)
IR (Nujol): 3340, 1770, 1590 cm$^{-1}$
NMR (CDCl$_3$, δ): 2.30–3.26 (4H, m), 3.35–3.47 (1H, m), 5.22 and 5.31 (1H, each d, J=18.2 and 6.1 Hz, respectively), 6.53–6.68 (2H, m), 7.12–7.65 (13H, m)

Preparation 71

A solution of ethyl 2-piperidinecarboxylate (10.0 ml), 3-methoxybenzyl chloride (9.2 ml), and triethylamine (26.6 ml) in N,N-dimethylformamide (64.0 ml) was stirred at room temperature overnight and partitioned between ethyl acetate and water. The organic layer was separated, washed with water (four times) and brine, dried over MgSO$_4$, and evaporated in vacuo. The residue was chromatographed over silica gel to afford ethyl 1-(3-methoxybenzyl)-2-piperidinecarboxylate (12.06 g) as a colorless oil.

(+) APCI-MS (m/z): 278 (M$^+$+1)
IR (Film): 1725, 1600, 1260 cm$^{-1}$
NMR (CDCl$_3$, δ): 1.29 (3H, t, J=7.1 Hz), 1.50–1.85 (6H, m), 2.10–2.22 (1H, m), 2.88–3.00 (1H, m), 3.14 (1H, dd, J=6.8, 5.2 Hz), 3.40 (1H, d, J=13.4 Hz), 3.78 (1H, d, J=13.4 Hz), 3.81 (3H, s), 4.21 (2H, q, J=7.1 Hz), 6.77–6.82 (1H, m), 6.89–6.93 (2H, m), 7.17–7.27 (1H, m)

Preparation 72

A solution of ethyl 1-(3-methoxybenzyl)-2-piperidinecarboxylate (3.0 g) and iN NaOH (21.6 ml) in ethanol (31.6 ml) was stirred at 70° C. overnight. The reaction mixture was cooled to room temperature, acidified with 1N hydrochloric acid, and evaporated in vacuo. The residue was extracted with methylene chloride and the extract was evaporated in vacuo to afford 1-(3-methoxybenzyl)-2-piperidinecarboxylic acid (2.64 g) as an amorphous powder.

(+) APCI-MS (m/z): 250 (M$^+$+1)
mp: 186.0–187.3° C.
IR (Film): 1600, 1265 cm$^{-1}$
NMR (CDCl$_3$, δ): 1.3–1.85 (6H, m), 2.2–2.3 (1H, m), 2.86–2.93 (1H, m), 3.09 (1H, dd, J=7.6, 4.3 Hz), 3.52 (1H, d, J=13.4 Hz), 3.74 (3H, s), 3.87 (1H, d, J=13.4 Hz), 6.81–6.93 (3H, m), 7.24 (1H, d, J=8.0 Hz)

Preparation 73

2-Oxo-1,2-diphenylethyl 1-(3-methoxybenzyl)-2-piperidinecarboxylate was prepared from 1-(3-methoxybenzyl)-2-piperidinecarboxylic acid and desyl bromide in a similar manner to that of Preparation 65.

(+) APCI-MS (m/z): 444 (M$^+$+1)
IR (Film): 1730, 1690, 1260 cm$^{-1}$

Preparation 74

2-(4,5-Diphenyl-2-oxazolyl)-1-(3-methoxybenzyl) piperidine was prepared from 2-oxo-1,2-diphenylethyl 1-(3-methoxybenzyl)-2-piperidinecarboxylate in a similar manner to that of Preparation 66.

(+) APCI-MS (m/z): 425 (M$^+$+1), 424
mp: 72.2–86.6° C.
IR (Film): 1600, 1260 cm$^{-1}$
NMR (CDCl$_3$, δ): 1.22–1.86 (6H, m), 2.04–2.23 (1H, m), 3.01–3.08 (1H, m), 3.20 (1H, d, J=13.9 Hz), 3.62 (1H, dd, J=10.8, 3.0 Hz), 3.75 (3H, s), 3.76 (1H, d, J=13.9 Hz), 6.73–6.78 (1H, m), 6.84–6.89 (2H, m), 7.16–7.37 (9H, m), 7.60 (2H, dd, J=7.8, 1.4 Hz)

Preparation 75

A 1.0M solution of boron tribromide in methylene chloride (2.08 ml) was added dropwise to a solution of 2-(4,5-diphenyl-2-oxazolyl)-1-(3-methoxybenzyl)piperidine (440 mg) in methylene chloride (2.5 ml) under ice cooling. The resulting mixture was stirred at the same temperature for 3 hours and partitioned between ethyl acetate and aqueous sodium bicarbonate. The organic layer was washed with water and brine, dried over MgSO$_4$, and evaporated in vacuo. The residue was chromatographed over silica gel to afford 2-(4,5-diphenyl-2-oxazolyl)-1-(3-hydroxybenzyl) piperidine (388 mg) as a pale yellow powder.

FABMS (m/z): 410 (M$^+$)
mp: 204.7–208.3° C.
IR (Film): 1600, 1585, 1255 cm$^{-1}$
NMR (CDCl$_3$, δ): 1.2–1.95 (6H, m), 2.0–2.25 (1H, m), 3.05–3.11 (1H, m), 3.25–3.37 (1H, m), 3.73–3.81 (2H, m), 6.71–6.83 (3H, m), 7.13 (1H, t, J=7.7 Hz), 7.25–7.48 (11H, m)

Preparation 76

2-Oxo-1,2-diphenylethyl 2-oxo-5-pyrrolidinecarboxylate was prepared from 2-oxo-5-pyrrolidinecarboxylic acid in a similar manner to that of Preparation 65.

(+) APCI-MS (m/z): 324 (M$^+$+1)
mp: 123.2–131.4° C.
IR (Nujol): 3350, 3190, 1730, 1700, 1675 cm$^{-1}$
NMR (CDCl$_3$, δ): 2.25–2.64 (4H, m), 4.35–4.45 (1H, m), 6.10 (1H, br d, J=11.4 Hz), 6.89 (1H, s), 7.26–7.53 (10H, m)

Preparation 77

2-(5-Imino-2-pyrrolidinyl)-4,5-diphenyloxazole was prepared from 2-oxo-1,2-diphenylethyl 2-oxo-5-pyrrolidinecarboxylate in a similar manner to that of Preparation 66.

(+) APCI-MS (m/z): 304 (M$^+$+1)
IR (Nujol): 3370, 1670 cm$^{-1}$
NMR (CDCl$_3$, δ): 2.2–2.6 (4H, m), 4.94 (1H, m), 6.99 (1H, s), 7.26–7.50 (10H, m)

Preparation 78

60% Sodium hydride (289 mg) was added to a stirred solution of 2-(5-imino-2-pyrrolidinyl)-4,5-diphenyloxazole (2.0 g) in N,N-dimethylformamide (20.0 ml) in the presence of an atmospheric N$_2$ gas under ice cooling and the resulting mixture was stirred at the same temperature for 20 minutes and at room temperature for 1 hour 20 minutes. 3-Methoxybenzyl chloride (1.72 g) was added to the mixture under ice cooling and stirring was continued at room temperature overnight. The reaction mixture was partitioned between 1N hydrochloric acid and ethyl acetate. The organic layer was separated, washed with water and aqueous sodium bicarbonate, dried over MgSO$_4$, and evaporated in vacuo. The oily residue was chromatographed to afford 2-[5-imino-1-(3-methoxybenzyl)-2-pyrrolidinyl]-4,5-diphenyloxazole (1.80 g) as an amorphous powder.

(+) APCI-MS (m/z): 424 (M$^+$+1)
IR (Nujol): 3400–3180, 1675, 1255 cm$^{-1}$
NMR (CDCl$_3$, δ): 2.23–2.67 (4H, m), 3.75 (3H, s), 4.68–4.75 (1H, m), 4.98 (2H, s), 6.02 (1H, br s), 6.49–6.55 (2H, m), 6.78–6.84 (1H, m), 7.15–7.51 (11H, m)

Preparation 79

2-[1-(3-Hydroxybenzyl)-5-imino-2-pyrrolidinyl]-4,5-diphenyloxazole was prepared from 2-[5-imino-1-(3-methoxybenzyl)-2-pyrrolidinyl]-4,5-diphenyloxazole in a similar manner to that of Preparation 75.

(+) APCI-MS (m/z): 410 (M$^+$+1)

IR (Nujol): 3150, 1665 cm$^{-1}$

NMR (DMSO-d$_6$, δ): 2.14–2.40 (4H, m), 4.66–4.73 (1H, m), 4.87 (1H, d, J=17.2 Hz), 5.12 (1H, d, J=17.2 Hz), 6.32–6.40 (2H, m), 6.59–6.65 (1H, m), 7.04–7.47 (1H, m), 7.99 (1H, s), 9.45 (1H, s)

Preparation 80

To a solution of N-phthaloyl-β-alanine (207 g) in THF (10 ml) was added SOCl$_2$ at 0° C. After being stirred for 2 hours at room temperature, the solvent was evaporated in vacuo. The residue was diluted with THF (10 ml), and benzoin (2.01 g) and pyridine (2 ml) were added to the solution at 0° C. After being stirred for 4 hours at room temperature, the solvent was evaporated in vacuo, and the residue was partitioned between ethyl acetate and 1N-HCl solution. The organic layer was washed with water and brine, dried over MgSO$_4$, and evaporated in vacuo. The obtained compound and CH$_3$COONH$_4$ (15.09 g) were dissolved in acetic acid (100 ml) and the mixture was stirred for 8 hours at 100° C. After the solvent was removed, the residue was partitioned between ethyl acetate and sat. NaHCO$_3$. The organic layer was washed with water and brine. The dried solvent was evaporated in vacuo and the residue was triturated with Et$_2$O to give N-phthaloyl-2-(4,5-diphenyloxazol-2-yl)ethylamine (2.84 g).

MS (m/z): 395 (M$^+$+1)

IR (Nujol): 1715, 1770 cm$^{-1}$

NMR (DMSO-d$_6$, δ): 3.21 (2H, t, J=6.8 Hz), 4.03 (2H, t, J=6.8 Hz), 7.32–7.44 (10H, m), 7.82–7.93 (4H, m)

Preparation 81

The following compound was obtained according to a similar manner to that of Preparation 80.

N-Phthaloyl-1-(4,5-diphenyloxazol-2-yl)ethylamine

MS (m/z): 395 (M$^+$+1)

IR (Nujol): 1700, 1770 cm$^{-1}$

NMR (DMSO-d$_6$, δ): 1.88 (3H, d, J=7.1 Hz), 5.69 (1H, q, J=7.1 Hz), 7.37–7.57 (10H, m), 7.87–7.97 (4H, m)

Preparation 82

To a solution of N-phthaloyl-2-(4,5-diphenyloxazol-2-yl)ethylamine (0.55 g) in DMF (5 ml) was added aqueous methylamine solution (7 ml). After being stirred for 3.5 hours at room temperature, the solution was partitioned between ethyl acetate and sat. NaHCO$_3$. The organic layer was washed three times with 1N-HCl. To the acidic aqueous layer was added powdered NaHCO$_3$. The aqueous layer was extracted with ethyl acetate. The dried organic solvent was evaporated in vacuo, and the residue was triturated with Et$_2$O-n-hexane to give 2-(4,5-diphenyloxazol-2-yl)ethylamine (0.33 g).

MS (m/z): 265 (M$^+$+1)

NMR (CDCl$_3$, δ): 3.32 (2H, t, J=5.9 Hz), 3.52 (2H, t, J=5.9 Hz), 5.60 (2H, br), 7.25–7.50 (6H, m), 7.55–7.70 (4H, m)

Preparation 83

The following compound was obtained according to a similar manner to that of Preparation 82.

1-(4,5-Diphenyloxazol-2-yl)ethylamine

MS (m/z): 265 (M$^+$+1)

NMR (CDCl$_3$, δ): 1.59 (3H, d, J=6.9 Hz), 4.25 (1H, q, J=6.9 Hz), 7.30–7.42 (6H, m), 7.56–7.68 (4H, m)

Preparation 84

A solution of 5-methoxy-1-oxo-1,2,3,4-tetrahydronaphthalene (0.67 g), 1-(4,5-diphenyloxazol-2-yl) ethylamine (0.98 g) and p-toluenesulfonic acid (catalytic amount) in toluene (30 ml) was refluxed for 7 hours with Dean-stark equipment. The solution was evaporated in vacuo and methanol (MeOH) (10 ml) was added to the residue. To the MeOH solution, NaBH$_4$ (0.21 g) was added at 0° C. After being stirred for 2 hours at room temperature, the solution was evaporated in vacuo. The residue was partitioned between ethyl acetate and water. The organic layer was washed with brine. The dried solvent was evaporated in vacuo, and the residue was purified by chromatography on silica gel to give 1-[1-(4,5-diphenyloxazol-2-yl) ethylamino]-1,2,3,4-tetrahydro-5-methoxynaphthalene (0.73 g).

MS (m/z): 425 (M$^+$+1)

NMR (CDCl$_3$, δ): 1.60 (3H, d, J=6.8 Hz), 1.60–2.08 (6H, m), 2.42–2.86 (2H, m), 3.80 (1.5H, s), 3.81 (0.5H, q, J=6.8 Hz), 3.82 (1.5H, s), 3.90 (0.5H, m), 4.29 (0.5H, q, J=6.8 Hz), 4.77 (0.5H, m), 6.73 (1H, m), 7.00–7.20 (2H, m), 7.33–7.39 (6H, m), 7.57–7.68 (4H, m)

Preparation 85

To a solution of 1-[1-(4,5-diphenyloxazol-2-yl) ethylamino]-1,2,3,4-tetrahydro-5-methoxynaphthalene (0.33 g) in CH$_2$Cl$_2$ (7 ml) was added 1M BBr$_3$—CH$_2$Cl$_2$ solution (1.5 ml) at 0° C. After being stirred for 3 hours at the same temperature, the solvent was evaporated in vacuo. The residue was partitioned between ethyl acetate and sat. NaHCO$_3$. The organic layer was washed with water and brine. The dried solvent was evaporated in vacuo. The residue was purified by chromatography on silica gel to give 1-[1-(4,5-diphenyloxazol-2-yl)ethylamino]-1,2,3,4-tetrahydro-5-hydroxynaphthalene (0.23 g).

MS (m/z): 411 (M$^+$+1)

NMR (CDCl$_3$, δ): 1.57 (3H, d, J=6.8 Hz), 1.84–2.20 (4H, m), 2.44–2.86 (2H, m), 3.89 (0.5H, m), 4.12 (0.5H, q, J=6.8 Hz), 4.29 (0.5H, q, J=6.8 Hz), 4.78 (0.5H, m), 6.62–6.72 (1H, m), 6.97–7.14 (2H, m), 7.32–7.41 (6H, m), 7.58–7.68 (4H, m)

Preparation 86

A solution of 5-(t-butyldiphenylsilyloxy)-1-oxo-1,2,3,4-tetrahydronaphthalene (0.52 g), 2-(4,5-diphenyloxazol-2-yl) ethylamine (0.33 g) and p-toluenesulfonic acid (catalytic amount) in toluene (30 ml) was refluxed for 15 hours with Dean-stark equipment. The solution was evaporated in vacuo and MeOH (10 ml) was added to the residue. To the MeOH solution, NaBH$_4$ (0.21 g) was added at 0° C. After being stirred for 30 minutes at room temperature, the solution was evaporated in vacuo. The residue was partitioned between ethyl acetate and water. The organic layer was washed with brine. The dried solvent was evaporated in vacuo, and the residue was purified by chromatography on silica gel to give 1-[2-(4,5-diphenyloxazol-2-yl) ethylamino]-1,2,3,4-tetrahydro-5-(t-butyldiphenylsilyloxy) naphthalene (0.25 g) and 1-[2-(4,5-diphenyloxazol-2-yl) ethylamino]-1,2,3,4-tetrahydro-5-hydroxynaphthalene (0.11 g). To a solution of 1-[2-(4,5-diphenyloxazol-2-yl) ethylamino]-1,2,3,4-tetrahydro-5-(t-butyldiphenylsilyloxy) naphthalene (0.25 g) in THF (2 ml) was added 1M-THF solution (2 ml) of tetra-n-butyl ammonium fluoride (TBAF). After being stirred for 1 hour at room temperature, the reaction mixture was partitioned between ethyl acetate and sat. NaHCO$_3$. The organic layer was washed with brine. The dried solvent was evaporated in vacuo. The residue was purified by chromatography on silica gel to give 1-[2-(4,5-diphenyloxazol-2-yl)ethylamino]-1,2,3,4-tetrahydro-5-hydroxynaphthalene (0.06 g).

MS (m/z): 411 (M$^+$+1)

NMR (CDCl$_3$, δ): 1.65–2.10 (4H, m), 2.38–2.85 (2H, m), 3.12 (2H, t, J=5.9 Hz), 3.22 (2H, t, J=5.9 Hz), 6.60–6.79 (1H, m), 6.89–7.12 (2H, m), 7.20–7.42 (6H, m), 7.52–7.75 (4H, m)

Preparation 87

A solution of 1,2,3,4-tetrahydro-5-methoxy-1-naphthalenamine (0.34 g), (4,5-diphenyloxazol-2-yl)methyl bromide (0.50 g) and potassium carbonate (0.60 g) in DMF (7 ml) was stirred for 5 hours at room temperature. The mixture was partitioned between ethyl acetate and water. The organic layer was washed with brine. The dried solvent was evaporated in vacuo. The residue was purified by chromatography on silica gel to give 1-[(4,5-diphenyloxazol-2-yl)methylamino]-1,2,3,4-tetrahydro-5-methoxynaphthalene (0.50 g).

MS (m/z): 411 ($M^+$+1)

NMR (CDCl$_3$, δ): 1.64–2.12 (4H, m), 2.38–2.92 (2H, m), 3.81 (3H, s), 3.94 (1H, m), 4.07 (2H, s), 6.73 (1H, d, J=7.9 Hz), 7.04 (1H, d, J=7.9 Hz), 7.15 (1H, dd, J=7.9, 7.9 Hz), 7.32–7.42 (6H, m), 7.58–7.69 (4H, m)

Preparation 88

The following compound was obtained according to a similar manner to that of Example 30.

1-[N-methyl-N-[(4,5-diphenyloxazol-2-yl)methyl]amino]-1,2,3,4-tetrahydro-5-methoxynaphthalene MS (m/z): 425 ($M^+$+1)

NMR (CDCl$_3$, δ): 1.50–1.72 (2H, m), 1.96–2.18 (2H, m), 2.42 (3H, s), 2.40–2.62 (1H, m), 2.72–2.92 (1H, m), 3.83 (5H, s), 4.06 (1H, m), 6.70 (1H, d, J=8.1 Hz), 7.16 (1H, dd, J=8.1, 8.1 Hz), 7.28–7.42 (6H, m), 7.54 (1H, d, J=8.1 Hz), 7.60–7.67 (4H, m)

Preparation 89

The following compounds were obtained according to a similar manner to that of Example 20.

(1) 1-Hydroxy-1,2,3,4-tetrahydro-5-methoxycarbonylmethoxynaphthalene

MS (m/z): 219 ($M^+$–OH)

NMR (CDCl$_3$, δ): 1.78–2.02 (4H, m), 2.60–2.72 (1H, m), 2.79–2.91 (1H, m), 3.80 (3H, s), 4.65 (2H, s), 4.77 (1H, m), 6.60–6.64 (1H, m), 7.09–7.20 (2H, m)

(2) 2,3-Dihydro-4-ethoxycarbonylmethoxy-1H-inden-1-ol

MS (m/z): 219 ($M^+$–OH)

IR (Nujol): 3290, 3190, 1720 cm$^{-1}$

NMR (CDCl$_3$, δ): 1.30 (3H, t, J=7.1 Hz), 1.72 (1H, d, J=6.2 Hz), 1.87–2.04 (1H, m), 2.43–2.60 (1H, m), 2.75–2.90 (1H, m), 3.03–3.18 (1H, m), 4.27 (2H, q, J=7.1 Hz), 4.65 (2H, s), 5.25 (1H, q, J=6.2 Hz), 6.65 (1H, d, J=7.9 Hz), 7.08 (1H, d, J=7.9 Hz), 7.20 (1H, dd, J=7.9, 7.9 Hz)

Preparation 90

To a solution of NaH (60% oil, 28 mg), 5-(4,5-diphenyloxazol-2-yl)pyrrolidin-2-one (0.15 g) and sodium iodide (catalytic amount) in THF (1 ml) was added a solution of 3-methoxybenzyl chloride (0.11 g) in THF (2 ml). After being stirred for 4 days at room temperature, the reaction mixture was partitioned between ethyl acetate and water. The organic layer was washed with brine. The dried solvent was evaporated in vacuo. The residue was purified by chromatography on silica gel to give 1-(3-methoxybenzyl)-5-(4,5-diphenyloxazol-2-yl)pyrrolidin-2-one (0.14 g).

MS (m/z): 425 ($M^+$+1)

NMR (CDCl$_3$, δ): 2.32–2.96 (4H, m), 3.65 (3H, s), 4.32 (1H, d, J=14.8 Hz), 4.70 (1H, d, J=14.8 Hz), 4.78 (1H, m), 6.68–6.82 (3H, m), 7.13 (1H, t, J=7.8 Hz), 7.33–7.48 (6H, m), 7.56–7.61 (4H, m)

Preparation 91

The following compound was obtained according to a similar manner to that of Preparation 75.

1-(3-Hydroxybenzyl)-5-(4,5-diphenyloxazol-2-yl)pyrrolidin-2-one

MS (m/z): 411 ($M^+$+1)

NMR (CDCl$_3$, δ): 2.18–2.98 (4H, m), 4.43 (1H, d, J=14.7 Hz), 4.56 (1H, d, J=14.7 Hz), 5.02 (1H, m), 6.64 (1H, d, J=7.8 Hz), 6.73 (1H, d, J=7.8 Hz), 6.84 (1H, m), 7.04 (1H, t, J=7.8 Hz), 7.35–7.42 (6H, m), 7.57–7.59 (4H, m)

Preparation 92

The following compound was obtained according to a similar manner to that of Preparation 84.

2-Benzylamino-5-t-butyldiphenylsilyloxy-1,2,3,4-tetrahydronaphthalene

FABMS (m/z): 492 ($M^+$+1)

NMR (CDCl$_3$, δ) 1.13 (9H, s), 1.50–1.80 (1H, m), 2.08–2.32 (1H, m), 2.52–3.24 (5H, m), 3.94 (2H, s), 6.23 (1H, d, J=7.5 Hz), 6.61 (1H, d, J=7.5 Hz), 6.68 (1H, dd, J=7.5, 7.5 Hz), 7.28–7.39 (10H, m), 7.66–7.74 (5H, m)

Preparation 93

A mixture of 2-benzylamino-5-t-butyldiphenylsilyloxy-1,2,3,4-tetrahydronaphthalene (3.15 g), ammonium formate (4.41 g) and Pd/C (0.15 g) in ethanol (EtOH) (40 ml) was refluxed for 3.5 hours. The insoluble material was filtered off and the solvent was evaporated in vacuo. The residue Has partitioned between ethyl acetate and sat. NaHCO$_3$. The organic layer was washed with brine. The dried solvent was evaporated in vacuo. The residue was purified by chromatography on silica gel to give 2-amino-5-t-butyldiphenylsilyloxy-1,2,3,4-tetrahydronaphthalene (1.18 g).

FABMS (m/z): 402 ($M^+$+1)

NMR (CDCl$_3$, δ): 1.10 (9H, s), 1.56–1.82 (1H, m), 2.05–2.35 (1H, m), 2.52–2.39 (5H, m), 6.24 (1H, d, J=6.4 Hz), 6.59–6.73 (2H, m), 7.32–7.42 (6H, m), 7.67–7.74 (4H, m)

Preparation 94

A solution of 2-amino-5-t-butyldiphenylsilyloxy-1,2,3,4-tetrahydronaphthalene (0.96 g), (4,5-diphenyloxazol-2-yl)methyl bromide (0.80 g) and potassium carbonate (0.41 g) in DMF (14 ml) was stirred for 3.5 hours at room temperature. The mixture was partitioned between ethyl acetate and water. The organic layer was washed with brine. The dried solvent was evaporated in vacuo to give crude 2-[(4,5-diphenyloxazol-2-yl)methylamino]-1,2,3,4-tetrahydro-5-t-butyldiphenylsilyloxynaphthalene. To a solution of crude 2-[(4,5-diphenyloxazol-2-yl)methylamino]-1,2,3,4-tetrahydro-5-t-butyldiphenylsilyloxynaphthalene in THF (5 ml) was added 1M THF (3 ml) solution of tetrabutylammonium fluoride. After being stirred for 1 hour at room temperature, the mixture was partitioned between ethyl acetate and sat. NaHCO$_3$. The organic layer was washed with brine. The dried solvent was evaporated in vacuo. The residue was purified by chromatography on silica gel to give 2-[(4,5-diphenyloxazol-2-yl)methylamino]-1,2,3,4-tetrahydro-5-hydroxynaphthalene (0.66 g).

MS (m/z): 397 ($M^+$+1)

NMR (CDCl$_3$, δ): 1.54–1.84 (2H, m), 2.08–2.22 (1H, m), 2.48–3.20 (5H, m), 4.13 (2H, s), 6.58 (1H, d, J=7.8 Hz), 6.68 (1H, d, J=7.8 Hz), 6.99 (1H, dd, J=7.8, 7.8 Hz), 7.34–7.40 (6H, m), 7.55–7.66 (4H, m)

Preparation 95

A solution of 1-amino-2,3-dihydro-4-methoxy-1H-indene (0.30 g), 4-hydroxy-1-(4,5-diphenyloxazol-2-yl)butan-1-one (0.56 g) and p-toluenesulfonic acid (catalytic amount) in toluene (50 ml) was refluxed for 2 days with Dean-stark equipment. The solvent was evaporated in vacuo and the residue was dissolved in methanol (10 ml). To the methanol solution was added NaBH$_4$ (0.20 g) at 0° C. After being stirred for 1 hour at the same temperature, the solvent was evaporated in vacuo and the residue was partitioned between ethyl acetate and sat. NaHCO$_3$. The organic layer was washed with brine. The dried solvent was evaporated in vacuo. The residue was purified by chromatography on silica gel to give 1-[[4-hydroxy-1-(4,5-diphenyloxazol-2-yl)butyl]amino]-2,3-dihydro-4-methoxy-1H-indene (0.27 g).

MS (m/z): 455 (M$^+$+1)

NMR (CDCl$_3$, δ): 1.60–3.20 (10H, m), 3.76 (2.5H, s), 3.84 (3.5H, s), 4.02–4.52 (2H, m), 7.59–7.69 (4H, m), 6.69–7.39 (9H, m)

Preparation 96

To a solution of 1-[[4-hydroxy-1-(4,5-diphenyloxazol-2-yl)butyl]amino]-2,3-dihydro-4-methoxy-1H-indene (0.27 g) in CH$_2$Cl$_2$ (5 ml) was added SOCl$_2$ (1 ml) at 0° C. After being stirred for 17 hours at room temperature, the solvent was evaporated in vacuo and the residue was dissolved in DMF (5 ml). To the mixture was added K$_2$CO$_3$ (2.07 g). After being stirred for 1 day at room temperature, the mixture was partitioned between ethyl acetate and water. The organic layer was washed with brine. The dried solvent was evaporated in vacuo. The residue was purified by chromatography on silica gel to give 1-[2-(4,5-diphenyloxazol-2-yl)pyrrolidin-1-yl]-2,3-dihydro-4-methoxy-1H-indene (0.15 g).

MS (m/z): 437 (M$^+$+1)

NMR (CDCl$_3$, δ) 1.42–3.20 (10H, m), 3.74 (2.5H, s), 3.81 (3.5H, s), 4.02–4.76 (2H, m), 6.58–7.72 (13H, m)

Preparation 97

The following compound was obtained according to a similar manner to that of Preparation 95.

1-[[6-Hydroxy-1-(4,5-diphenyloxazol-2-yl)hexyl]amino]-2,3-dihydro-4-methoxy-1H-indene MS (m/z): 469 (M$^+$+1)

NMR (CDCl$_3$, δ): 1.40–3.20 (12H, m), 3.82 (3H, m), 4.15–4.94 (2H, m), 6.68–7.41 (9H, m), 7.57–7.69 (4H, m)

Preparation 98

The following compound was obtained according to a similar manner to that of Preparation 96.

1-[2-(4,5-Diphenyloxazol-2-yl)piperidin-1-yl]-2,3-dihydro-4-methoxy-1H-indene

MS (m/z): 451 (M$^+$+1)

NMR (CDCl$_3$, δ) 1.58–3.02 (12H, m), 3.77 (3H, s), 3.80 (3H, s), 4.07–4.44 (2H, m), 6.63–7.36 (9H, m), 7.36–7.70 (4H, m)

Preparation 99

To a solution of 4-hydroxy-1-(4,5-bis(4-methylphenyl)-oxazol-2-yl)butan-1-one (0.78 g) and triethylamine (2 ml) in DMSO (10 ml) was added a solution of pyridinesulfonic acid (1.16 g) in DMSO (4 ml) at room temperature. After being stirred for 20 minutes at the same temperature, the mixture was partitioned between ethyl acetate and water. The organic layer was washed with 1M-HCl, water and brine. The dried solvent was evaporated in vacuo and the residue was purified by chromatography on silica gel to give 1-[4,5-bis(4-methylphenyl)oxazol-2-yl]butan-1,4-dione (0.22 g).

MS (m/z): 334 (M$^+$+1)

IR (Nujol): 1735, 1690 cm$^{-1}$

NMR (CDCl$_3$, δ): 2.38 (3H, s), 2.40 (3H, s), 2.97 (2H, t, J=6.4 Hz), 3.47 (2H, t, J=6.4 Hz), 7.17–7.26 (4H, m), 7.53–7.59 (4H, m), 9.88 (1H, s)

Preparation 100

A solution of 1,2,3,4-tetrahydro-5-t-butyldiphenylsilyloxy-1-naphthaleneamine (0.21 g), 1-[4,5-bis(4-methylphenyl)oxazol-2-yl]butan-1,4-dione (0.12 g), NaBH$_3$CN (84 mg) and KOH (30 mg) in acetic acid (0.5 ml) and methanol (4 ml). After being stirred for 3 days at room temperature, the solvent was evaporated in vacuo. The residue was partitioned between ethyl acetate and sat. NaHCO$_3$. The organic layer was washed with brine. The dried solvent was evaporated in vacuo. The residue was purified by chromatography on silica gel to give 1-[2-[4,5-bis(4-methylphenyl)oxazol-2-yl]pyrrolidin-1-yl]-1,2,3,4-tetrahydro-5-t-butyldiphenylsilyloxynaphthalene (0.24 g).

FABMS (m/z): 702 (M$^+$–1)

NMR (CDCl$_3$, δ): 1.08 (9H, s), 1.58–3.04 (12H, m), 2.34 (3H, s), 2.36 (3H, s), 6.18–7.80 (21H, m)

Preparation 101

The following compound was obtained according to a similar manner to that of Preparation 70.

1-[2-, [4,5-Bis(4-methylphenyl)oxazol-2-yl]pyrrolidin-1-yl]-1,2,3,4-tetrahydro-5-hydroxynaphthalene MS (m/z): 465 (M$^+$+1)

NMR (CDCl$_3$, δ): 1.46–3.00 (12H, m), 2.36 (6H, s), 3.86–4.70 (2H, m), 6.42–7.62 (11H, m)

Preparation 102

To a solution of 1-(4,5-diphenyloxazol-2-yl)methylamino-2,3-dihydro-4-methoxy-1H-indene (0.13 g) in formic acid (5 ml) was added acetic anhydride (1 ml) at 0° C. After being stirred for 5 hours at room temperature, the solvent was evaporated in vacuo. The residue was partitioned between ethyl acetate and 1N hydrochloric acid. The organic layer was washed with water, sat. NaHCO$_3$, and brine. The dried solvent was evaporated in vacuo and the residue was purified by chromatography on silica gel to give l-[N-formyl-N-[(4,5-diphenyloxazol-2-yl)methyl]amino]-2,3-dihydro-4-methoxy-1H-indene (0.12 g).

MS (m/z): 425 (M$^+$+1)

NMR (CDCl$_3$, δ): 8.52 (0.25H, s), 8.43 (0.75H, s), 7.60–7.40 (4H, m), 7.38–7.24 (6H, m), 7.18–6.95 (1H, m), 6.78–6.55 (2H, m), 6.18 (0.25H, m), 5.28 (0.75H, m), 4.72 (0.75H, d, J=16.2 Hz), 4.51 (0.75H, d, J=16.2 Hz), 4.12 (0.5H, m), 3.79 (2.25H, s), 3.72 (0.75H, s), 3.20–2.94 (1H, m), 2.92–2.66 (1H, m), 2.62–2.38 (1H, m), 2.35–2.05 (1H, m)

Preparation 103

To a solution of 1-(4,5-diphenyloxazol-2-yl)methylamino-2,3-dihydro-4-methoxy-1H-indene (0.22 g) and pyridine (0.2 ml) in dichloromethane (5 ml) was added acetyl chloride (0.15 ml) at 0° C. The mixture was stirred for 1.5 hours at the same temperature and partitioned between ethyl acetate and 1N hydrochloric acid. The organic layer was washed with water, sat. NaHCO$_3$, and brine. The dried solvent was evaporated in vacuo and the residue was purified by chromatography on silica gel to give 1-[N-acetyl-N-[(4,5-diphenyloxazol-2-yl)methyl]amino]-2,3-dihydro-4-methoxy-1H-indene (0.08 g).

MS (m/z): 439 (M$^+$+1)

IR (Nujol): 1640 cm$^{-1}$

NMR (CDCl$_3$, δ): 7.65–7.45 (4H, m), 7.40–7.20 (6H, m), 7.19–7.02 (1H, m), 6.82–6.60 (2H, m), 6.40 (0.5H, t, J=7.5 Hz), 5.56 (0.5H, t, J=7.5 Hz), 4.72 (0.5H, d, J=8.1 Hz), 4.42 (1H, m), 4.19 (0.5H, d, J=8.1 Hz), 3.81 (1.5H, s), 3.78 (1.5H, s), 2.37 (1.5H, s), 3.15–2.92 (1H, m), 2.90–2.64 (1H, m), 2.62–2.42 (1H, m), 2.40–2.10 (1H, m), 2.37 (1.5H, s), 2.35 (1.5H, s)

Preparation 104

To a solution of 1-[N-acetyl-N-[(4,5-diphenyloxazol-2-yl)methyl]amino]-2,3-dihydro-4-methoxy-1H-indene (0.40 g) in THF (10 ml) was added 1M solution of borane-THF complex in THF (9 ml) at room temperature. The reaction mixture was refluxed for 8 hours and cooled down to room temperature. 1N aqueous HCl solution (25 ml) was added to the reaction mixture. After being stirred for 1 hour at room temperature, the mixture was partitioned between ethyl acetate and 1N aqueous NaOH solution. The organic layer was washed with brine. The dried solvent was evaporated in vacuo to give 1-[N-ethyl-N-[(4,5-diphenyloxazol-2-yl) methyl]amino]-2,3-dihydro-4-methoxy-1H-indene (0.47 g).

MS (m/z): 425 (M$^+$+1)

NMR (CDCl$_3$, δ): 7.66–7.58 (4H, m), 7.39–7.08 (8H, m), 6.70 (1H, d, J=7.7 Hz), 4.67 (1H, t, J=7.6 Hz), 3.81 (3H, s), 3.18–2.80 (2H, m), 2.73 (2H, a, J=7.2 Hz), 2.35–1.84 (2H, m), 1.14 (3H, t, J=7.2 Hz)

Preparation 105

To a solution of 4-methoxy-1-indanone (0.71 g) and iso-propylamine (8 ml) in dichloromethane (10 ml) was added 1M solution of titanium(IV) chloride in dichloromethane (11 ml) at −60° C. for 15 minutes. The reaction mixture was stirred for 3 hours at the same temperature. Methanol (15 ml) wash added to the reaction mixture. After being stirred for 2 hours at room temperature, the solution was evaporated in vacuo. The residue was partitioned between ethyl acetate and 1N aqueous NaOH solution. The insoluble material was filtered off by zeolite. The organic layer was washed with brine. The dried solvent was evaporated in vacuo to give 1-isopropylamino-2,3-dihydro-4-methoxy-1H-indene (0.89 g).

MS (m/z) 206 (M$^+$+1)

NMR (CDCl$_3$, δ) 7.18 (1H, dd, J=7.8, 7.8 Hz), 6.97 (1H, d, J=7.8 Hz), 6.71 (1H, d, J=7.8 Hz), 4.30 (1H, t, J=6.7 Hz), 3.83 (3H, s), 3.20–2.87 (2H, m), 2.80–2.60 (1H, m), 2.50–2.35 (1H, m), 2.00–1.68 (1H, m), 1.13 (3H, d, J=6.9 Hz), 1.12 (3H, d, J=6.9 Hz)

Preparation 106

The following compound was obtained according to a similar manner to that of Preparation 17.

1-[N-isopropyl-N-[(4,5-diphenyloxazol-2-yl)methyl] amino]-2,3-dihydro-4-methoxy-1H-indene MS (m/z): 439 (M$^+$+1)

NMR (CDCl$_3$, δ): 7.61–7.57 (4H, m), 7.50–7.20 (6H, m), 7.18–7.05 (2H, m), 6.85–6.60 (1H, m), 4.67 (1H, t, J=8.0 Hz), 3.80 (3H, s), 3.83–3.78 (2H, m), 3.25–2.85 (2H, m), 2.80–2.60 (1H, m), 2.28–2.00 (2H, m), 1.21 (3H, d, J=6.6 Hz), 1.14 (3H, d, J=6.6 Hz)

EXAMPLE 19

To a solution of 1-[2-[4,5-bis(4-methylphenyl)oxazol-2-yl]pyrrolidin-1-yl]-1,2,3,4-tetrahydro-5-hydroxynaphthalene (0.13 g) and ethyl bromoacetate (0.10 g) in DMF (5 ml) was added K$_2$CO$_3$ (0.13 g). After being stirred for 2 days at room temperature, the mixture was partitioned between ethyl acetate and water. The organic layer was washed with brine. The dried solvent was evaporated in vacuo. The residue was purified by chromatography on silica gel to give 1-[2-[4,5-bis(4-methylphenyl)oxazol-2-yl]pyrrolidin-1-yl]-1,2,3,4-tetrahydro-5-ethoxycarbonylmethoxynaphthalene (0.13 g).

MS (m/z): 551 (M$^+$+1)

NMR (CDCl$_3$, δ): 1.18–1.40 (4H, m), 1.52–2.98 (18H, m), 3.90–4.70 (6H, m), 6.34–7.60 (11H, m)

EXAMPLE 20

A solution of 1-(3-hydroxybenzyl)-5-(4,5-diphenyloxazol-2-yl)pyrrolidin-2-one (0.13 g), ethyl bromoacetate (0.21 g), potassium carbonate (99 mg) and potassium iodide (catalytic amount) in acetonitrile (10 ml) was refluxed for 9 hours. The reaction mixture was partitioned between ethyl acetate and brine. The organic layer was washed with brine. The dried solvent was evaporated in vacuo. The residue was purified by chromatography on silica gel to give 1-(3-ethoxycarbonylmethoxybenzyl)-5-(4,5-diphenyloxazol-2-yl)pyrrolidin-2-one (0.16 g).

MS (m/z): 497 (M$^+$+1)

NMR (CDCl$_3$, δ): 1.28 (3H, t, J=7.1 Hz), 2.20–2.96 (4H, m), 4.23 (2H, q, J=7.1 Hz), 4.38 (1H, d, J=14.7 Hz), 4.43 (2H, s), 4.70 (1H, d, J=14.7 Hz), 4.76 (1H, m), 6.70–6.87 (3H, m), 7.15 (1H, t, J=7.8 Hz), 7.33–7.56 (6H, m), 7.57–7.61 (4H, m)

EXAMPLE 21

A solution of NaH (60% oil, 66 mg) and 1-[1-(4,5-diphenyloxazol-2-yl)ethylamino]-1,2,3,4-tetrahydro-5-hydroxynaphthalene (0.55 g) in DMF (10 ml) was stirred for 30 minutes at room temperature. To the reaction mixture was added ethyl bromoacetate (0.26 g). After being stirred for 7 hours at room temperature, the solution was partitioned between ethyl acetate and sat. NaHCO$_3$. The organic layer was washed with brine. The dried solvent was evaporated in vacuo. The residue was purified by chromatography on silica gel to give 1-[1-(4,5-diphenyloxazol-2-yl)ethylamino]-1,2,3,4-tetrahydro-5-ethoxycarbonylmethoxynaphthalene (0.38 g).

MS (m/z): 497 (M$^+$+1)

IR (Film): 1740 cm$^{-1}$

NMR (CDCl$_3$, δ): 1.29 (3H, t, J=7.1 Hz), 1.60 (3H, t, J=6.6 Hz), 1.70–1.85 (3H, m), 1.90–2.15 (1H, m), 2.44–2.98 (2H, m), 3.89 (1H, m), 4.24–4.31 (3H, m), 4.60 (2H, s), 6.55–6.60 (1H, m), 7.08–7.11 (2H, m), 7.32–7.40 (6H, m), 7.58–7.69 (4H, m)

EXAMPLE 22

A mixture of 1-(3-hydroxybenzoyl)-2-(4,5-diphenyl-2-oxazolyl)piperidine (100 mg), ethyl bromoacetate (61 mg), and K$_2$CO$_3$ (84 mg) in acetonitrile (1.0 ml) was stirred at room temperature overnight and partitioned between water and ethyl acetate. The organic layer was separated, washed with water and brine, dried over MgSO$_4$, and evaporated in vacuo. The residue was chromatographed over silica gel to afford 1-[3-(ethoxycarbonylmethoxy)benzoyl]-2-(4,5-diphenyl-2-oxazolyl)piperidine (90 mg) as a colorless oil.

EXAMPLE 23

The following compounds were obtained according to similar manners to those of Examples 19–22.

(1) Ethyl [3-[[2-(4,5-diphenyloxazol-2-yl)-2-cyclohexen-1-yl]methyl]-4-methylphenoxy]acetate MS (m/z): 508 (M$^+$+1)

IR (Neat): 1750 cm$^{-1}$

NMR (CDCl$_3$, δ): 1.25 (3H, t, J=7 Hz), 1.4–2.6 (7H, m), 2.42 (3H, s), 3.1–3.3 (2H, m), 4.22 (2H, q, J=7 Hz), 4.58 (2H, s), 6.63 (1H, d, J=8.0 Hz), 6.8–7.0 (2H, m), 7.03 (1H, t, J=8 Hz), 7.2–7.8 (11H, m)

(2) Ethyl [3-[(2-(4,5-diphenyloxazol-2-yl)-2-cyclohexen-1-yl]methyl]-6-methylphenoxy]acetate MS (m/z): 508 (M$^+$+1)

IR (Neat): 1750 cm$^{-1}$

NMR (CDCl$_3$, δ): 1.26 (3H, t, J=7 Hz), 1.4–2.5 (6H, m), 2.22 (3H, s), 2.41 (1H, dd, J=10.0, 12.4 Hz), 3.0–3.3 (2H, m), 4.22 (2H, q, J=7 Hz), 4.62 (2H, s), 6.7–7.2 (4H, m), 7.2–7.8 (11H, m)

(3) Ethyl [3-[[2-(4,5-diphenyloxazol-2-yl)-2-cyclohexen-1-yl]methyl]-2-methylphenoxy]acetate MS (m/z): 508 (M$^+$+1)

IR (Neat): 1750 cm$^{-1}$

NMR (CDCl$_3$, δ): 1.25 (3H, t, J=7 Hz), 1.4–2.0 (4H, m), 2.2–2.4 (2H, m), 2.48 (3H, s), 2.61 (1H, dd, J=12.0, 13.4 Hz), 4.22 (2H, q, J=7 Hz), 4.64 (2H, s), 6.58 (1H, d, J=8.0 Hz), 6.8–7.0 (2H, m), 7.03 (1H, t, J=8 Hz), 7.2–7.8 (11H, m)

(4) Ethyl [4-[[2-(4,5-diphenyloxazol-2-yl)-2-cyclohexen-1-yl]methyl]phenoxy]acetate
MS (m/z): 494 (M$^+$+1)
IR (Neat): 1740 cm$^{-1}$
NMR (CDCl$_3$, δ): 1.25 (3H, t, J=7 Hz), 1.6–2.0 (4H, m), 2.1–2.3 (2H, m), 2.50 (1H, dd, J=10, 13.2 Hz), 3.0–3.3 (2H, m), 4.22 (2H, q, J=7 Hz), 4.58 (2H, s), 6.81 (2H, d, J=8.0 Hz), 6.83 (1H, m), 7.2–7.8 (12H, m)

(5) 2-[1-[3-(Ethoxycarbonylmethoxy)benzyl]-5-imino-2-pyrrolidinyl]-4,5-diphenyloxazole
(+) APCI-MS (m/z): 496 (M$^+$+1)
IR (Nujol): 3400–3180, 1740, 1680 cm$^{-1}$
NMR (CDCl$_3$, δ): 1.22 (3H, t, J=7.1 Hz), 2.23–2.64 (4H, m), 4.22 (2H, q, J=7.1 Hz), 4.55 (2H, s), 4.70–4.77 (1H, m), 5.00 (2H, s), 5.87 (1H, br s), 6.48 (1H, m), 6.57–6.62 (1H, m), 6.78–6.84 (1H, m), 7.13–7.52 (11H, m)

(6) 2-(4,5-Diphenyl-2-oxazolyl)-1-[3-(ethoxycarbonylmethoxy)benzyl]piperidine
FABMS (m/z): 496 (M$^+$)
mp: 56.6–65.0° C.
IR (Film): 1750, 1600, 1265 cm$^{-1}$
NMR (CDCl$_3$, δ): 1.27 (3H, t, J=7.1 Hz), 1.41–2.17 (7H, m), 2.99–3.05 (1H, m), 3.20 (1H, d, J=14.0 Hz), 3.61 (1H, dd, J=10.7, 2.9 Hz), 3.75 (1H, d, J=14.0 Hz), 4.23 (2H, q, J=7.1 Hz), 4.56 (2H, s), 6.71–6.76 (1H, m), 6.86–6.91 (2H, m), 7.15–7.36 (9H, m), 7.60 (2H, dd, J=7.9, 1.4 Hz)

(7) 2-(4,5-Diphenyl-2-oxazolyl)-3-[3-(ethoxycarbonylmethoxy)benzyl]-5-oxotetrahydrofuran
(+) APCI-MS (m/z): 498 (M$^+$+1)
IR (Film): 1780, 1750, 1600, 1585, 1200 cm$^{-1}$
NMR (CDCl$_3$, δ): 1.28 and 1.29 (3H, each t, J=7.1 Hz), 2.35–3.03 (4H, m), 3.28–3.49 (1H, m), 4.25 (2H, q, J=7.1 Hz), 4.53 (2H, s), 5.30 and 5.66 (1H, each d, J=5.9 and 7.7 Hz, respectively), 6.69–6.85 (3H, m), 7.15–7.41 (7H, m), 7.53–7.66 (4H, m)

(8) 1-[2-(4,5-Diphenyloxazol-2-yl)ethylamino]-1,2,3,4-tetrahydro-5-methoxycarbonylmethoxynaphthalene
MS (m/z): 483 (M$^+$+1)
NMR (CDCl$_3$, δ): 1.65–2.08 (4H, m), 2.56–2.92 (2H, m), 3.10 (2H, t, J=5.9 Hz), 3.20 (2H, t, J=5.9 Hz), 3.51 (1H, m), 3.84–3.90 (1H, m), 3.79 (3H, s), 4.62 (2H, s), 6.50–6.60 (1H, m), 7.00–7.14 (2H, m), 7.22–7.40 (6H, m), 7.48–7.68 (4H, m)

(9) 2-[(4,5-Diphenyloxazol-2-yl)methylamino]-1,2,3,4-tetrahydro-5-methoxycarbonylmethoxynaphthalene
MS (m/z): 469 (M$^+$+1)
NMR (CDCl$_3$, δ): 1.52–1.80 (1H, m), 2.04–2.21 (1H, m), 2.58–2.81 (2H, m), 2.92–3.18 (3H, m), 3.79 (3H, s), 4.13 (2H, s), 4.63 (2H, s), 6.52 (1H, d, J=7.8 Hz), 6.75 (1H, d, J=7.8 Hz), 7.05 (1H, dd, J=7.8, 7.8 Hz), 7.33–7.40 (6H, m), 7.56–7.66 (4H, m)

EXAMPLE 24

To a solution of 1-(4,5-diphenyloxazol-2-yl)-8-(3-methoxybenzyl)-1-cyclooctene (3.0 g) in dichloromethane (80 ml) was added BBr$_3$ (17 ml, 1M solution in dichloromethane) at 0° C. After being stirred for 2 hours, the solvent was evaporated in vacuo. The residue was diluted with ethyl acetate, and the mixture was washed with water and brine. The dried solvent was evaporated and the residue was dissolved in DMF (40 ml) and then K$_2$CO$_3$ (3 g) and ethyl bromoacetate (1.2 ml) were added at room temperature. The mixture was stirred for 2 hours at the same temperature and partitioned between ethyl acetate and water. The organic layer was washed with water and brine. The dried solvent was evaporated in vacuo and the residue was purified by chromatography on silica gel to give 1-(4,5-diphenyloxazol-2-yl)-8-(3-ethoxycarbonylmethoxybenzyl)-1-cyclooctene (2.3 g).
MS (m/z): 522 (M$^+$+1)
IR (Neat): 1740 cm$^{-1}$
NMR (CDCl$_3$, δ): 1.25 (3H, t, J=7 Hz), 1.4–2.0 (8H, m), 2.2–2.4 (2H, m), 3.0–3.5 (3H, m), 4.22 (2H, q, J=7 Hz), 4.49 (2H, s), 6.66 (1H, s), 6.7–7.0 (3H, m), 7.15 (1H, t, J=8 Hz), 7.2–7.8 (10H, m)

EXAMPLE 25

The following compounds were obtained according to similar manners to those of Examples 17 and 24.

(1) 1-[2-(4,5-Diphenyloxazol-2-yl)piperidin-1-yl]-2,3-dihydro-4-ethoxycarbonylmethoxy-1H-indene
MS (m/z): 522 (M$^+$+1)
NMR (CDCl$_3$, δ): 1.22–1.33 (3H, m), 1.42–3.08 (12H, m), 4.10–4.61 (6H, m), 6.48–7.45 (9H, m), 7.54–7.78 (4H, m)

(2) 1-[2-(4,5-Diphenyloxazol-2-yl)pyrrolidin-1-yl]-2,3-dihydro-4-ethoxycarbonylmethoxy-1H-indene
MS (m/z): 509 (M$^+$+1)
NMR (CDCl$_3$, δ): 1.22–1.40 (3H, m), 1.60–3.20 (10H, m), 4.02–4.76 (6H, m), 6.40–7.78 (13H, m)

(3) 1-[N-Methyl-N-[(4,5-diphenyloxazol-2-yl)methyl]amino]-1,2,3,4-tetrahydro-5-methoxycarbonylmethoxynaphthalene
MS (m/z): 483 (M$^+$+1)
IR (Film): 1730 cm$^{-1}$
NMR (CDCl$_3$, δ): 1.56–1.78 (2H, m), 1.92–2.20 (2H, m), 2.41 (3H, s), 3.05–4.43 (2H, m), 3.80 (5H, s), 4.00 (1H, m), 4.63 (2H, s), 6.60 (1H, m), 7.15 (1H, m), 7.28–7.43 (6H, m), 7.55–7.70 (5H, m)

(4) 1-[N-Isopropyl-N-[(4,5-diphenyloxazol-2-yl)methyl]amino]-2,3-dihydro-4-ethoxycarbonylmethoxy-1H-indene
MS (m/z): 511 (M$^+$+1)
NMR (CDCl$_3$, δ): 7.75–7.50 (4H, m), 7.50–7.25 (6H, m), 7.20–7.05 (2H, m), 6.60–6.45 (1H, m), 4.59 (2H, s), 4.75–4.55 (1H, m), 4.24 (2H, q, J=7.1 Hz), 3.80 (2H, m), 3.25–2.95 (2H, m), 2.90–2.60 (1H, m), 2.34–2.00 (2H, m), 1.29 (3H, t, J=7.1 Hz), 1.21 (3H, d, J=6.6 Hz), 1.15 (3H, d, J=6.6 Hz)

(5) 1-[N-Ethyl-N-[(4,5-diphenyloxazol-2-yl)methyl]amino]-2,3-dihydro-4-ethoxycarbonylmethoxy-1H-indene
MS (m/z): 497 (M$^+$+1)
IR (Film): 1740 cm$^{-1}$
NMR (CDCl$_3$, δ): 7.70–7.58 (4H, m), 7.45–7.25 (6H, m), 7.16–7.13 (2H, m), 6.57 (1H, m), 4.67 (1H, m), 4.61 (2H, s), 4.24 (2H, q, J=7.1 Hz), 3.85 (2H, s), 3.18–2.65 (4H, m), 2.35–1.85 (2H, m), 1.29 (3H, t, J=7.1 Hz), 1.14 (3H, t, J=7.1 Hz)

(6) 1-[N-Acetyl-N-[(4,5-diphenyloxazol-2-yl)methyl]amino]-2,3-dihydro-4-ethoxycarbonylmethoxy-1H-indene
MS (m/z): 511 (M$^+$+1)
NMR (CDCl$_3$, δ): 7.68–7.45 (4H, m), 7.42–7.24 (6H, m), 7.20–7.00 (1H, m), 6.92–6.72 (1H, m), 6.60–6.45 (1H, m), 6.40 (0.5H, m), 5.58 (0.5H, m), 4.80–4.40 (2H, m), 4.25 (2H, q, J=7.1 Hz), 3.20–2.97 (1H, m), 2.95–2.70 (1H, m), 2.68–2.40 (1H, m), 2.38–2.20 (1H, m), 2.36 (1.5H, s), 2.35 (1.5H, s), 1.29 (3H, s, J=7.1 Hz)

(7) 1-[N-Formyl-N-[(4,5-diphenyloxazol-2-yl)methyl]amino]-2,3-dihydro-4-ethoxycarbonylmethoxy-1H-indene
MS (m/z): 497 (M$^+$+1)
NMR (CDCl$_3$, δ): 8.52 (0.25H, s), 8.43 (0.75H, s), 7.60–7.43 (4H, m), 7.42–7.22 (6H, m), 7.18–6.48 (3.25H, m), 5.32 (0.75H, m), 4.80–4.20 (6H, m), 3.24–2.38 (4H, m), 1.29 (3H, t, J=7.1 Hz)

(8) Ethyl [3-[[2-(4,5-diphenyloxazol-2-yl)-2-cyclohexen-1-yl]methyl]-4-phenylphenoxy]acetate
MS (m/z): 570 (M$^+$+1)
IR (Neat): 1750 cm$^{-1}$
NMR (CDCl$_3$, δ): 1.25 (3H, t, J=7 Hz), 1.2–2.0 (4H, m), 2.0–2.2 (2H, m), 2.78 (1H, dd, J=12.0, 14.6 Hz), 3.1–3.3 (2H, m), 4.22 (2H, q, J=7 Hz), 4.58 (2H, s), 6.7–7.0 (3H, m), 7.1–7.5 (12H, m), 7.6–7.8 (4H, m)

(9) Ethyl [2-[[2-(4,5-diphenyloxazol-2-yl)-2-cyclohexen-1-yl]methyl]phenoxy]acetate
MS (m/z): 494 (M$^+$+1)
IR (Neat): 1740 cm$^{-1}$
NMR (CDCl$_3$, δ): 1.25 (3H, t, J=7 Hz), 1.4–2.0 (4H, m), 2.2–2.4 (2H, m), 2.7–3.4 (3H, m), 4.22 (2H, q, J=7 Hz), 4.58 (2H, s), 6.68 (1H, d, J=8.0 Hz), 6.8–7.0 (2H, m), 7.11 (1H, t, J=8 Hz), 7.2–7.8 (11H, m)

(10) 1-(3-Ethoxycarbonylmethoxyphenylcarbonyl)-2-(4,5-diphenyloxazol-2-yl)pyrrolidine
MS (m/z): 497 (M$^+$+1)
IR (Neat): 1750, 1640 cm$^{-1}$
NMR (CDCl$_3$, δ): 1.2 (2H, m), 2.1–2.5 (4H, m), 3.5–4.4 (5H, m), 4.6 (2H, s), 6.6–7.0 (3H, m), 7.1–7.8 (11H, m)

(11) 2-(4,5-Diphenyloxazol-2-yl)-3-(3-ethoxycarbonylmethoxybenzyl)bicyclo[2.2.1]hept-2-ene
MS (m/z): 506 (M$^+$+1)
IR (Neat): 1740 cm$^{-1}$
NMR (CDCl$_3$, δ): 1.22 (3H, t, J=7 Hz), 1.2–2.0 (6H, m), 2.80 (1H, br s), 3.61 (1H, br s), 3.79 (1H, d, J=16.6 Hz), 4.22 (2H, q, J=7 Hz), 4.32 (1H, d, J=16.6 Hz), 4.65 (2H, s), 6.7–7.0 (3H, m), 7.22 (1H, t, J=8 Hz), 7.2–7.8 (10H, m)

(12) 1-[(4,5-Diphenyloxazol-2-yl)methylamino]-2,3-dihydro-4-ethoxycarbonylmethoxy-1H-indene
MS (m/z): 469 (M$^+$+1)
IR (Film) 1750 cm$^{-1}$
NMR (CDCl$_3$, δ): 7.75–7.50 (4H, m), 7.45–7.20 (6H, m), 7.18–7.02 (2H, m), 6.65–6.58 (1H, m), 4.62 (2H, s), 4.45 (1H, m), 4.26 (2H, q, J=7.1 Hz), 4.10 (2H, s), 3.22–3.00 (1H, m), 2.95–2.72 (1H, m), 2.55–2.25 (1H, m), 2.12–1.86 (1H, m), 1.70 (1H, br), 1.29 (3H, t, J=7.1 Hz)

EXAMPLE 26

The following compounds were obtained according to similar manners to those of Examples 1 and 2.

(1) 1-[2-(4,5-Diphenyloxazol-2-yl)piperidin-1-yl]-5-ethoxycarbonylmethoxy-1,2,3,4-tetrahydronaphthalene
MS (m/z): 537 (M$^+$+1)
IR (Neat): 1750 cm$^{-1}$
NMR (CDCl$_3$, δ): 1.24 (3H, t, J=7 Hz), 1.4–2.4 (10H, m), 2.5–3.1 (2H, m), 3.6–4.2 (2H, m), 4.49, 4.58 (2H, each s), 6.43, 6.53 (1H, each d, J=8.0 Hz), 7.03, 7.20 (1H, each t, J=8 Hz), 7.3–7.8 (11H, m)

(2) 1-[2-(4,5-Diphenyloxazol-2-yl)azetidin-1-yl]-5-ethoxycarbonylmethoxy-1,2,3,4-tetrahydronaphthalene
MS (m/z): 509 (M$^+$+1)
IR (Neat): 1750 cm$^{-1}$
NMR (CDCl$_3$, δ): 1.24 (3H, t, J=7 Hz), 1.4–3.0 (8H, m), 3.1–3.4 (2H, m), 4.24 (2H, q, J=7 Hz), 4.57 (2H, s), 4.4–4.7 (2H, m), 6.40, 6.59 (1H, each d, J=8.0 Hz), 6.8–7.1 (2H, m), 7.3–7.7 (10H, m)

(3) 1-[4-(4,5-Diphenyloxazol-2-yl)-2-oxoazetidin-1-yl]-5-ethoxycarbonylmethoxy-1,2,3,4-tetrahydronaphthalene
MS (m/z): 523 (M$^+$+1)
IR (Neat): 1750 cm$^{-1}$
NMR (CDCl$_3$, δ): 1.24 (3H, t, J=7 Hz), 1.6–2.2 (4H, m), 2.6–2.8 (2H, m), 3.3–3.7 (2H, m), 4.24 (2H, q, J=7 Hz), 4.57 (2H, s), 4.6–4.8 (1H, m), 5.0–5.3 (1H, m), 6.59 (1H, d, J=8.0 Hz), 6.84 (1H, d, J=8.0 Hz), 7.16 (1H, t, J=8.0 Hz), 7.3–7.7 (10H, m)

(4) 1-[2-(4,5-Diphenyloxazol-2-yl)tetrahydrofuran-3-yl]-5-ethoxycarbonylmethoxy-3,4-dihydronaphthalene
MS (m/z): 522 (M$^+$)
IR (Neat): 1740 cm$^{-1}$
NMR (CDCl$_3$, δ): 1.25 (3H, t, J=7 Hz), 2.0–3.0 (6H, m), 3.7–4.2 (3H, m), 4.24 (2H, q, J=7 Hz), 4.44 (2H, s), 5.48 (1H, d, J=8.0 Hz), 5.94 (1H, m), 6.68 (1H, d, J=8 Hz), 7.0–7.7 (12H, m)

(5) 1-[2-(4,5-Diphenyloxazol-2-yl)pyrrolidin-1-yl]-2-hydroxy-5-ethoxycarbonylmethoxy-1,2,3,4-tetrahydronaphthalene
MS (m/z): 539 (M$^+$)
IR (Neat): 1740 cm$^{-1}$
NMR (CDCl$_3$, δ): 1.24 (3H, t, J=7 Hz), 1.5–2.4 (6H, m), 2.4–2.7 (1H, m), 2.9–3.1 (1H, m), 3.4–3.7 (3H, m), 4.0–4.1 (1H, m), 4.24 (2H, q, J=7 Hz), 4.4–4.5 (1H, m), 4.59 (2H, s), 6.57 (1H, d, J=8 Hz), 6.99 (1H, d, J=8.0 Hz), 7.14 (1H, t, J=8.0 Hz), 7.2–7.7 (10H, m)

(6) 2-[2-(4,5-Diphenyloxazol-2-yl)pyrrolidin-1-yl]-5-ethoxycarbonylmethoxy-1,2,3,4-tetrahydronaphthalene
MS (m/z): 523 (M$^+$)
IR (Neat): 1740 cm$^{-1}$
NMR (CDCl$_3$, δ): 1.24 (3H, t, J=7 Hz), 1.5–2.0 (6H, m), 2.4–2.7 (1H, m), 2.8–3.3 (6H, m), 4.24 (2H, q, J=7 Hz), 4.40 (1H, m), 4.56 (2H, s), 6.4–7.1 (3H, m), 7.2–7.7 (10H, m)

(7) 1-[3-Hydroxy-1-(4,5-diphenyloxazol-2-yl) propylamino]-5-ethoxycarbonylmethoxy-1,2,3,4-tetrahydronaphthalene
MS (m/z):527 (M$^+$)
IR (Neat): 1750 cm$^{-1}$
NMR (CDCl$_3$, δ): 1.28 (3H, t, J=7 Hz), 1.4–2.5 (6H, m), 2.5–3.0 (2H, m), 3.8–4.0 (3H, m), 4.0–4.3 (1H, m), 4.22 (2H, q, J=7 Hz), 4.60 (2H, s), 6.58 (1H, m), 6.9–7.1 (2H, m), 7.3–7.8 (10H, m)

(8) (1R)-1-[4-Hydroxy-1-(4,5-diphenyloxazol-2-yl) butylamino]-5-ethoxycarbonylmethoxy-1,2,3,4-tetrahydronaphthalene
MS (m/z): 541 (M$^+$)
IR (Neat): 1750 cm$^{-1}$
NMR (CDCl$_3$, δ): 1.24 (3H, t, J=7 Hz), 1.4–2.4 (8H, m), 2.6–3.0 (2H, m), 3.5–3.7 (2H, m), 3.9 (1H, m), 4.0–4.2 (1H, m), 4.24 (2H, q, J=7 Hz), 4.59 (2H, s), 6.57 (1H, m), 6.9–7.2 (2H, m), 7.3–7.8 (10H, m)

EXAMPLE 27

A solution of 1-hydroxy-1,2,3,4-tetrahydro-5-methoxycarbonylmethoxynaphthalene (0.42 g) and Lawesson's reagent (0.40 g) in toluene (4 ml) was refluxed under N$_2$ atmosphere for 1 hour. The reaction mixture was purified by chromatography on silica gel to give 1-mercapto-1,2,3,4-tetrahydro-5-methoxycarbonylmethoxynaphthalene (0.26 g). A solution of 1-mercapto-1,2,3,4-tetrahydro-5-methoxycarbonylmethoxynaphthalene (0.26 g), (4,5-diphenyloxazol- 2-yl)methyl bromide (0.32 g) and potassium carbonate (0.14 g) in DMF (5 ml) was stirred for 6 hours at room temperature. The mixture was partitioned between ethyl acetate and water. The organic layer was washed with brine. The dried solvent was evaporated in vacuo. The residue was purified by chromatography on silica gel to give 1-[(4,5-diphenyloxazol-2-yl)methylthio]-1,2,3,4-tetrahydro-5-methoxycarbonylmethoxynaphthalene (0.29 g).

MS (m/z): 486 (M$^+$+1)
NMR (CDCl$_3$, δ): 1.75–1.92 (1H, m), 2.00–2.22 (3H, m), 2.45–2.72 (1H, m), 2.80–3.02 (1H, m), 3.79 (3H, s), 3.91

(1H, s), 3.94 (1H, s), 4.36 (1H, m), 4.60 (2H, s), 6.50–6.55 (1H, m), 7.04–7.06 (2H, m), 7.33–7.40 (6H, m), 7.59–7.68 (4H, m)

EXAMPLE 28

The following compound was obtained according to a similar manner to that of Example 27.

1-[(4,5-Diphenyloxazol-2-yl)methylthio]-2,3-dihydro-4-ethoxycarbonylmethoxy-1H-indene MS (m/z): 486 (M$^+$+1)

NMR (CDCl$_3$, δ) 1.29 (3H, t, J=7.1 Hz), 2.22–2.28 (1H, m), 2.55–2.65 (1H, m), 2.96–3.12 (2H, m), 3.90 (1H, s), 3.91 (1H, s), 4.26 (2H, s), 4.60 (2H, s), 4.52–4.63 (1H, m), 6.55–6.59 (2H, m), 7.09–7.13 (2H, m), 7.34–7.38 (6H, m), 7.57–7.67 (4H, m)

EXAMPLE 29

A solution of 1-[1-(4,5-diphenyloxazol-2-yl)ethylamino]-1,2,3,4-tetrahydro-5-ethoxycarbonylmethoxynaphthalene (0.24 g), iodomethane (77 mg) and K$_2$CO$_3$ (82 mg) in DMF (5 ml) was stirred for 5 hours at room temperature. The reaction mixture was partitioned between ethyl acetate and water. The organic layer was washed with brine. The dried solvent was evaporated in vacuo. The residue was purified by chromatography on silica gel to give 1-[N-methyl-N-[1-(4,5-diphenyloxazol-2-yl)ethyl]amino]-1,2,3,4-tetrahydro-5-ethoxycarbonylmethoxynaphthalene (0.12 g).

MS (m/z): 511 (M$^+$+1)

IR (Film): 1730 cm$^{-1}$

NMR (CDCl$_3$, δ): 1.29 (3H, t, J=7.1 Hz), 1.63 (3H, d, J=7.1 Hz), 1.58–1.88 (3H, m), 1.95–2.18 (1H, m), 2.26 (3H, m), 2.46–2.68 (1H, m), 2.80–3.00 (1H, m), 4.12 (2H, q, J=7.1 Hz), 4.26 (3H, q, J=7.1 Hz), 4.60 (2H, s), 6.56 (1H, d, J=7.9 Hz), 7.11 (1H, dd, J=7.9, 7.9 Hz), 7.26–7.50 (7H, m), 7.59–7.68 (4H, m)

EXAMPLE 30

To a solution of (2R)-2-(4,5-diphenyloxazol-2-yl) pyrrolidine (400 mg) and 3-bromomethyl-1-ethoxycarbonylmethoxybenzene (0.76 g) in N,N-dimethylformamide (10 ml) was added K$_2$CO$_3$ (1 g) at room temperature. The mixture was stirred for 2 hours at the same temperature and then partitioned between ethyl acetate and water. The organic layer was washed with water, sat. NaHCO$_3$, and brine. The dried solvent was evaporated in vacuo and the residue was purified by chromatography on silica gel to give (2R)-2-(4,5-diphenyloxazol-2-yl)-1(3-ethoxycarbonylmethoxybenzyl)pyrrolidine (0.27 g).

MS (m/z): 483 (M$^+$+1)

IR (Neat): 1750 cm$^{-1}$

NMR (CDCl$_3$, δ): 1.25 (3H, t, J=7.0 Hz), 1.8–2.5 (5H, m), 3.14 (1H, m), 3.60 (1H, d, J=14 Hz), 3.84 (1H, m), 3.85 (1H, d, J=14 Hz), 4.23 (2H, q, J=7.0 Hz), 4.48 (2H, s), 6.71 (1H, d, J=8 Hz), 6.8–7.0 (2H, m), 7.16 (1H, t, J=8.0 Hz), 7.3–7.8 (16H, m)

EXAMPLE 31

The following compound was obtained according to a similar manner to that of Example 30.

(2S)-2-(4,5-Diphenyloxazol-2-yl)-1-(3-ethoxycarbonylmethoxybenzyl)pyrrolidine

MS (m/z): 483 (M$^+$+1)

IR (Neat): 1750 cm$^{-1}$

NMR (CDCl$_3$, δ): 1.25 (3H, t, J=7.0 Hz), 1.8–2.5 (5H, m), 3.14 (1H, m), 3.60 (1H, d, J=14 Hz), 3.84 (1H, m), 3.85 (1H, d, J=14 Hz), 4.23 (2H, q, J=7.0 Hz), 4.48 (2H, s), 6.71(1H, d, J=8 Hz), 6.8–7.0 (2H, m), 7.16 (1H, t, J=8.0 Hz), 7.3–7.8 (16H, m)

EXAMPLE 32

The following compound was obtained according to similar manners to those of Preparations 28 and 29.

1-(4,5-Diphenyloxazol-2-yl)-6-[3-(2-ethoxycarbonylethyl)benzyl]-1-cyclohexene

MS (m/z): 492 (M$^+$+1)

IR (Neat): 1730 cm$^{-1}$

NMR (CDCl$_3$, δ): 1.22 (3H, t, J=7 Hz), 1.4–2.0 (4H, m), 2.2–2.8 (5H, m), 2.95 (2H, t, J=8 Hz), 3.0–3.4 (2H, m), 4.15 (2H, q, J=8 Hz), 6.8–7.1 (2H, m), 7.1–7.8 (13H, m)

EXAMPLE 33

To a solution of (2R)-2-(4,5-diphenyloxazol-2-yl)-1-(3-ethoxycarbonylmethoxybenzylpyrrolidine (270 mg) in ethanol (10 ml) was added 1N-NaOH solution (0.56 ml). After being stirred for 12 hours at the same temperature, the solvent was removed in vacuo to give sodium [3-[[(2R)-2-(4,5-diphenyloxazol-2-yl)pyrrolidin-1-yl]methyl]phenoxy] acetate (0.21 g).

FABMS (m/z): 477 (M$^+$+1)

IR (Nujol): 1600 cm$^{-1}$

NMR (DMSO-d$_6$, δ) 1.7–2.4 (4H, m), 2.5 (1H, m), 2.9 (1H, m), 3.52 (1H, d, J=12 Hz), 3.81 (1H, d, J=12 Hz), 3.86 (1H, t, J=6.8 Hz), 4.03 (2H, s), 6.6–6.9 (3H, m), 7.08 (1H, t, J=8 Hz), 7.3–7.8 (10H, m)

EXAMPLE 34

The following compounds were obtained according to similar manners to those of Examples 7, 8, 18 and 33.

(1) Sodium salt of 1-[2-[4,5-bis(4-methylphenyl)oxazol-2-yl]pyrrolidin-1-yl]-1,2,3,4-tetrahydro-5-carboxymethoxynaphthalene FABMS (m/z): 567 (M$^+$+Na), 545 (M$^+$+1)

NMR (CD$_3$OD, δ): 1.50–3.08 (18H, m), 3.80–4.38 (4H, m), 6.38–7.42 (11H, m)

(2) Sodium salt of 1-[2-(4,5-diphenyloxazol-2-yl)piperidin-1-yl]-2,3-dihydro-4-carboxymethoxy-1H-indene FABMS (m/z): 539 (M$^+$+Na), 517 (M$^+$+1)

NMR (CD$_3$OD, δ): 1.40–3.12 (12H, m), 4.02–4.42 (4H, m), 6.48–6.68 (1H, m), 6.92–7.18 (2H, m), 7.28–7.65 (10H, m)

(3) Sodium salt of 1-[2-(4,5-diphenyloxazol-2-yl)pyrrolidin-1-yl]-2,3-dihydro-4-carboxymethoxy-1H-indene MS (m/z): 481 (free M$^+$+1)

NMR (CD$_3$OD, δ): 1.72–3.12 (10H, m), 4.04–4.40 (4H, m), 6.42–7.60 (13H, m)

(4) Sodium salt of 2-[(4,5-diphenyloxazol-2-yl)methylamino]-1,2,3,4-tetrahydro-5-carboxymethoxynaphthalene FABMS (m/z): 499 (M$^+$+Na), 477 (M$^+$+1)

NMR (CD$_3$OD, δ): 1.48–1.76 (1H, m), 2.06–2.32 (1H, m), 2.52–2.80 (2H, m), 2.88–3.18 (3H, m), 4.12 (2H, s), 4.37 (2H, s), 6.52–6.68 (2H, m), 6.92–7.04 (1H, m), 7.30–7.42 (6H, m), 7.53–7.62 (4H, m)

(5) Sodium salt of 1-(3-carboxymethoxybenzyl)-5-(4,5-diphenyloxazol-2-yl)pyrrolidin-2-one FABMS (m/z): 513 (M$^+$+Na), 491 (M$^+$+1)

NMR (CD$_3$OD, δ): 2.27–2.86 (4H, m), 4.16 (2H, s), 4.46 (1H, d, J=14.8 Hz), 4.52 (1H, d, J=14.8 Hz), 6.68–6.76 (3H, m), 7.05 (1H, m), 7.31–7.51 (10H, m)

(6) Sodium salt of 1-[(4,5-diphenyloxazol-2-yl)methylthio]-2,3-dihydro-4-carboxymethoxy-1H-indene FABMS (m/z): 502 (M$^+$+Na), 480 (M$^+$+1)

NMR (CD$_3$OD, δ): 2.06–2.38 (1H, m), 2.42–2.75 (1H, m), 2.84–3.20 (2H, m), 3.94 (1H, s), 3.95 (1H, s), 4.34 (2H, s), 4.50 (1H, m), 6.61 (1H, d, J=8.0 Hz), 6.90 (1H, d, J=8.0 Hz), 7.03 (1H, d, J=8.0, 8.0 Hz), 7.35–7.40 (6H, m), 7.50–7.57 (4H, m)

(7) Sodium salt of 1-[(4,5-diphenyloxazol-2-yl)methylthio]-1,2,3,4-tetrahydro-5-carboxymethoxynaphthalene FABMS (m/z): 516 (M$^+$+Na), 494 (M$^+$+1)

NMR (DMSO-d$_6$, δ): 1.05–2.20 (4H, m), 2.32–2.95 (2H, m), 4.06 (4H, m), 4.36 (1H, m), 6.51 (1H, d, J=8.0 Hz), 6.79 (1H, d, J=8.0 Hz), 6.91 (1H, J=8.0 Hz), 7.35–7.65 (10H, m)

(8) Sodium salt of 1-[N-methyl-N-[(4,5-diphenyloxazol-2-yl)methyl]amino]-1,2,3,4-tetrahydro-5-carboxymethoxynaphthalene FABMS (m/z): 513 (M$^+$+Na), 467 (M$^+$+1)

NMR (CD$_3$OD, δ): 1.58–1.82 (2H, m), 2.00–2.18 (2H, m), 2.48–2.74 (1H, m), 2.82–3.02 (1H, m), 2.42 (3H, s), 3.81 (2H, m), 3.99 (1H, m), 4.36 (2H, s), 6.64 (1H, d, J=7.7 Hz), 7.02 (1H, d, J=7.7 Hz), 7.32–7.65 (11H, m)

(9) Sodium salt of 1-[2-(4,5-diphenyloxazol-2-yl)ethylamino]-1,2,3,4-tetrahydro-5-carboxymethoxynaphthalene FABMS (m/z): 491 (M$^+$+1)

NMR (CD$_3$OD, δ): 1.64–2.17 (4H, m), 2.56–2.98 (2H, m), 3.19 (2H, m), 3.29 (2H, m), 3.98 (1H, m), 4.38 (2H, s), 6.66–6.72 (1H, m), 6.88–7.12 (2H, m), 7.25–7.44 (6H, m), 7.46–7.63 (4H, m)

(10) Sodium salt of 1-[N-methyl-N-[1-(4,5-diphenyloxazol-2-yl)ethyl]amino]-1,2,3,4-tetrahydro-5-carboxymethoxynaphthalene FABMS (m/z): 527 (M$^+$+Na), 505 (M$^+$+1)

NMR (CD$_3$OD, δ): 1.62 (3H, d, J=7.0 Hz), 1.60–1.80 (3H, m), 1.95–2.08 (1H, m), 3.27 (3H, s), 2.44–2.68 (1H, m), 2.80–3.00 (1H, m), 4.11 (1H, m), 4.28 (1H, m), 4.36 (2H, s), 6.61 (1H, d, J=7.7 Hz), 7.02 (1H, dd, J=7.7, 7.7 Hz), 7.28 (1H, d, J=7.7 Hz), 7.36–7.44 (6H, m), 7.53–7.60 (4H, m)

(11) Sodium salt of 1-[1-(4,5-diphenyloxazol-2-yl)ethylamino]-1,2,3,4-tetrahydro-5-carboxymethoxynaphthalene FABMS (m/z): 513 (M$^+$+Na), 491 (M$^+$+1)

NMR (DMSO-d$_6$, δ): 1.56 (3H, d, J=6.8 Hz), 1.64–2.18 (4H, m), 2.55–3.00 (2H, m), 3.86 (1H, m), 4.28 (1H, q, J=6.8 Hz), 4.34 (2H, s), 6.63 (1H, d, J=7.8 Hz), 6.91 (1H, d, J=7.8 Hz), 7.02 (1H, dd, J=7.8, 7.8 Hz), 7.35–7.43 (6H, m), 7.53–7.59 (4H, m)

(12) Sodium salt of 1-[N-isopropyl-N-[(4,5-diphenyloxazol-2-yl)methyl]amino]-2,3-dihydro-4-carboxymethoxy-1H-indene FABMS (m/z): 527 (M$^+$+Na)

NMR (CD$_3$OD, δ): 7.55–7.28 (10H, m), 7.05–6.95 (2H, m), 6.68–6.50 (1H, m), 4.72 (1H, t, J=8.0 Hz), 4.33 (2H, s), 3.82 (2H, s), 3.40–2.60 (3H, m), 2.30–2.00 (2H, m), 1.23 (3H, d, J=6.8 Hz), 1.20 (3H, d, J=6. 8 Hz)

(13) Sodium salt of 1- [N-ethyl-N- [(4,5-diphenyloxazol-2-yl)methyl]amino]-2,3-dihydro-4-carboxymethoxy-1H-indene FABMS (m/z): 513 (M$^+$+Na)

NMR (CD$_3$OD, δ): 7.60–7.44 (4H, m), 7.42–7.32 (6H, m), 7.12–6.99 (2H, m), 6.66–6.62 (1H, m), 4.66 (1H, t, J=7.4 Hz), 4.36 (2H, s), 3.85 (2H, dd, J=3.6, 3.6 Hz), 3.18–2.99 (1H, m), 2.98–2.70 (3H, m), 2.35–1.90 (2H, m), 1.16 (3H, t, J=7.2 Hz)

(14) Sodium salt of 1-[N-acetyl-N-[(4,5-diphenyloxazol-2-yl)methyl]amino]-2,3-dihydro-4-carboxymethoxy-1H-indene FABMS (m/z): 527 (M$^+$+Na)

NMR (CD$_3$OD, δ): 7.60–7.24 (10H, m), 7.15–6.55 (3H, m), 6.35–6.20 (0.25H, m), 5.78–5.65 (0.75H, m), 4.56–4.34 (4H, m), 3.32–3.08 (1H, m), 3.04–2.80 (1H, m), 2.75–2.04 (2H, m), 2.38 (3H, s)

(15) 1-[N-Formyl-N-[(4,5-diphenyloxazol-2-yl)methyl]amino]-2,3-dihydro-4-carboxymethoxy-1H-indene MS (m/z): 469 (M$^+$+1), 411 (M+1+-CH$_2$COO)

NMR (CDCl$_3$, δ): 8.53 (0.3H, s), 8.45 (0.7H, s), 7.60–7.50 (10H, m), 7.12–6.44 (3H, m), 6.20 (0.3H, m), 5.31 (0.7H, m), 4.61 (2H, d, J=18.3 Hz), 4.51 (2H, d, J=20.6 Hz), 3.42–3.06 (1H, m), 3.02–2.78 (1H, m), 2.68–2.40 (1H, m), 2.32–2.02 (1H, m)

(16) Sodium salt of 1-[(4,5-diphenyloxazol-2-yl)methylamino]-2,3-dihydro-4-carboxymethoxy-1H-indene FABMS (m/z): 485 (M$^+$+Na)

NMR (CD$_3$OD, δ): 7.60–7.53 (4H, m), 7.46–7.31 (6H, m), 7.11 (1H, dd, J=7.6, 7.6 Hz), 7.01 (1H, d, J=7.6 Hz), 6.68 (1H, d, J=7.6 Hz), 4.38 (2H, s), 4.38 (1H, t, J=6.3 Hz), 4.03 (1H, s), 3.19–2.79 (2H, m), 2.47– 2.35 (1H, m), 2.05–1.87 (1H, m)

(17) Sodium salt of 1-[3-(carboxymethoxy)benzoyl]-2-(4,5-diphenyl-2-oxazolyl)piperidine FABMS (m/z): 505 (M$^+$+1)

mp: 205.4–211.3° C.

IR (Nujol): 1610, 1580 cm$^{-1}$

NMR (DMSO-d$_6$, δ): 1.4–2.0 (6H, m), 3.35 (1H, m), 2.7–3.75 (1H, m), 4.14 (2H, s), 4.4 and 6.01 (1H, each m), 6.87–6.94 (3H, m), 7.27–7.64 (11H, m)

(18) 3-[3-(Carboxymethoxy)benzyl]-2-(4,5-diphenyl-2-oxazolyl)-5-oxotetrahydrofuran (+) APCI-MS (m/z): 470 (M$^+$+1)

mp: 65.2–72.2° C.

IR (Film): 1775, 1730, 1580, 1200 cm$^{-1}$

NMR (CDCl$_3$, δ): 2.35–3.02 (4H, m), 3.24–3.47 (1H, m), 4.56 and 4.58 (2H, each s), 5.33 and 5.69 (1H, each d, J=6.1 and 7.7 Hz, respectively), 6.65–6.86 (3H, m), 7.16–7.41 (7H, m), 7.52–7.64 (4H, m)

(19) Sodium salt of 1-[3-(carboxymethoxy)benzyl]-2-(4,5-diphenyl-2-oxazolyl)piperidine FABMS (m/z): 490 (M$^+$)

mp: >250° C.

IR (Film): 1625, 1600, 1260 cm$^{-1}$

NMR (DMSO-d$_6$, δ): 1.2–2.1 (7H, m), 2.85–2.92 (1H, m), 3.01 (1H, d, J=13.5 Hz), 3.23–3.6 (2H, m), 4.08 (2H, s), 6.62–6.67 (1H, m), 6.77–6.82 (1H, m), 6.87 (1H, m), 7.10 (1H, t, J=7.7 Hz), 7.19–7.34 (6H, m), 7.45–7.50 (4H, m)

(20) Sodium salt of 2-[1-[3-(carboxymethoxy)benzyl]-5-imino-2-pyrrolidinyl]-4,5-diphenyloxazole FABMS (m/z): 490 (M$^+$+1)

mp: 239.9–241.7° C.

IR (Nujol): 3200, 1680, 1605 cm$^{-1}$

NMR (DMSO-d$_6$, δ): 2.1–2.5 (4H, m), 4.00 (2H, s), 4.69 (1H, m), 4.93 (1H, d, J=17.2 Hz), 5.08 (1H, d, J=17.2 Hz), 6.40 (2H, m), 6.69 (1H, m), 7.14–7.44 (11H, m), 8.09 (1H, s)

(21) Sodium salt of (1R)-1-[4-hydroxy-1-(4,5-diphenyloxazol-2-yl)butylamino]-5-carboxymethoxy-1,2,3,4-tetrahydronaphthalene FABMS (m/z): 535 (M$^+$+1)

IR (Nujol) 3400, 1600 cm$^{-1}$

NMR (DMSO-d$_6$, δ) 1.4–2.3 (8H, m), 2.3–2.8 (2H, m), 3.3–3.5 (2H, m), 3.7 (1H, m), 3.9–4.1 (1H, m), 4.08 (2H, s), 6.53 (1H, d, J=8.0 Hz), 6.8–7.0 (2H, m), 7.2–7.6 (10H, m)

(22) Sodium salt of 1-[3-hydroxy-1-(4,5-diphenyloxazol-2-yl)propylamino]-5-carboxymethoxy-1,2,3,4-tetrahydronaphthalene FABMS (m/z): 521 (M$^+$+1)
IR (Nujol): 3400, 1600 cm$^{-1}$
NMR (DMSO-d$_6$, δ): 1.5–2.2 (6H, m), 2.4–2.8 (2H, m), 3.3–3.8 (4H, m), 4.09 (2H, s), 4.0–4.2 (1H, m), 6.54 (1H, d, J=8.0 Hz), 6.8–7.1 (2H, m), 7.2–7.6 (10H, m)

(23) Sodium [3-[[(2S)-2-(4,5-diphenyloxazol-2-yl) pyrrolidin-1-yl]methyl]phenoxy]acetate
FABMS (m/z): 477 (M$^+$+1)
IR (Nujol): 1600 cm$^{-1}$
NMR (DMSO-d$_6$, δ): 1.7–2.4 (4H, m), 2.5 (1H, m), 2.9 (1H, m), 3.52 (1H, d, J=12 Hz), 3.81 (1H, d, J=12 Hz), 3.86 (1H, t, J=6.8 Hz), 4.03 (2H, s), 6.6–6.9 (3H, m), 7.08 (1H, t, J=8 Hz), 7.3–7.8 (10H, m)

(24) Sodium (3-[[2-(4,5-diphenyloxazol-2-yl)-2-cycloocten-1-yl]methyl]phenoxy)acetate
FABMS (m/z): 516 (M$^+$+1)
IR (Neat): 1600 cm$^{-1}$
NMR (DMSO-d$_6$, δ): 1.0–2.1 (8H, m), 2.3–2.5 (2H, m), 2.9 (1H, m), 3.3–3.6 (2H, m), 3.98 (2H, s), 6.6–6.8 (3H, m), 6.74 (1H, t, J=8 Hz), 7.00 (1H, t, J=8.0 Hz), 7.2–7.8 (10H, m)

(25) Sodium salt of 2-(4,5-diphenyloxazol-2-yl)-3-(3-carboxymethoxybenzyl)bicyclo[2.2.1]hept-2-ene
FABMS (m/z): 500 (M$^+$+1)
IR (Neat): 1600 cm$^{-1}$
NMR (DMSO-d$_6$, δ): 1.0–1.8 (6H, m), 2.83 (1H, br s), 3.48 (1H, br s), 3.78 (1H, d, J=14 Hz), 4.01 (2H, s), 4.18 (1H, d, J=14 Hz), 6.6–6.8 (3H, m), 7.13 (1H, t, J=8.0 Hz), 7.3–7.8 (10H, m)

(26) Sodium [3-[[2-(4,5-diphenyloxazol-2-yl)pyrrolidin-1-yl]carbonyl]phenoxy)acetate
IR (Neat): 1580–1620 cm$^{-1}$
NMR (DMSO-d$_6$, δ): 1.8–2.4 (4H, m), 3.5–3.8 (2H, m), 4.9–4.2 (2H, m), 5.0–5.3 (1H, m), 6.6–7.0 (3H, m), 7.1–7.8 (11H, m)

(27) Sodium [2-[[2-(4,5-diphenyloxazol-2-yl)-2-cyclohexen-1-yl]methyl]phenoxy]acetate
FABMS (m/z): 488 (M$^+$+1)
IR (Neat): 1600 cm$^{-1}$
NMR (DMSO-d$_6$, δ): 1.2–2.2 (4H, m), 2.0–2.4 (2H, m), 2.6–3.2 (3H, m), 4.16 (2H, s), 6.6–6.8 (3H, m), 6.10 (1H, t, J=8 Hz), 7.19 (1H, d, J=8.0 Hz), 7.3–7.8 (10H, m)

(28) Sodium [4-[[2-(4,5-diphenyloxazol-2-yl)-2-cyclohexen-1-yl]methyl]phenoxy]acetate
FABMS (m/z): 488 (M$^+$+1)
IR (Neat): 1600 cm$^{-1}$
NMR (DMSO-d$_6$, δ): 1.4–2.0 (4H, m), 2.0–2.4 (2H, m), 2.8–3.2 (3H, m), 4.05 (2H, s), 6.75 (2H, d, J=8.0 Hz), 6.88 (1H, m), 7.13 (2H, d, J=8.0 Hz), 7.3–7.8 (10H, m)

(29) Sodium [3-[[2-(4,5-diphenyloxazol-2-yl)-2-cyclohexen-1-yl]methyl]-4-methylphenoxy]acetate
FABMS (m/z): 502 (M$^+$+1)
IR (Neat): 1600 cm$^{-1}$
NMR (DMSO-d$_6$, δ): 1.2–2.4 (4H, m), 2.30 (3H, s), 2.8–3.2 (2H, m), 4.12 (2H, s), 6.6–6.9 (3H, m), 6.99 (1H, d, J=8 Hz), 7.3–7.8 (10H, m)

(30) Sodium [3-[[2-(4,5-diphenyloxazol-2-yl)-2-cyclohexen-1-yl]methyl]-6-methylphenoxy]acetate
FABMS (m/z): 502 (M$^+$+1)
IR (Neat): 1600 cm$^{-1}$
NMR (DMSO-d$_6$, δ): 1.2–2.4 (4H, m), 2.12 (3H, s), 4.17 (2H, s), 6.6–7.0 (3H, m), 6.98 (1H, d, J=8 Hz), 7.3–7.8 (10H, m)

(31) Sodium [3-[[2-(4,5-diphenyloxazol-2-yl)-2-cyclohexen-1-yl]methyl-2-methylphenoxy]acetate
FABMS (m/z): 502 (M$^+$+1)
IR (Neat): 1600 cm$^{-1}$
NMR (DMSO-d$_6$, δ): 1.2–2.0 (4H, m), 2.37 (3H, s), 4.15 (2H, s), 6.60 (1H, d, J=8.0 Hz), 6.71 (1H, d, J=8.0 Hz), 6.8–7.0 (2H, m), 7.2–7.8 (10H, m)

(32) Sodium 3-[3-[[2-(4,5-diphenyloxazol-2-yl)-2-cyclohexen-1-yl]methyl]phenyl]propionate
IR (Neat): 1580 cm$^{-1}$
NMR (DMSO-d$_6$, δ): 1.4–2.0 (4H, m), 2.0–2.9 (7H, m), 3.0–3.2 (2H, m), 6.80 (1H, br s), 6.9–7.2 (3H, m), 7.3–7.8 (10H, m)

(33) Sodium [3-[[2-(4,5-diphenyloxazol-2-yl)-2-cyclohexen-1-yl]methyl]-4-phenylphenoxy]acetate
FABMS (m/z): 564 (M$^+$+1)
IR (Neat): 1600 cm$^{-1}$
NMR (DMSO-d$_6$, δ): 1.2–2.0 (4H, m), 2.0–2.4 (2H, m), 2.5–3.2 (3H, m), 4.17 (2H, s), 6.6–7.0 (3H, m), 7.0–7.8 (16H, m)

(34) Sodium salt of 2-[2-(4,5-diphenyloxazol-2-yl) pyrrolidin-1-yl]-5-carboxymethoxy-1,2,3,4-tetrahydronaphthalene
FABMS (m/z): 516 (M$^+$)
IR (Nujol): 1600 cm$^{-1}$
NMR (DMSO-d$_6$, δ): 1.5–3.2 (13H, m), 4.08 (2H, s), 4.33 (1H, m), 6.3–6.6 (2H, m), 6.7–7.0 (1H, m), 7.2–7.6 (10H, m)

(35) Sodium salt of 1-[2-(4,5-diphenyloxazol-2-yl) pyrrolidin-1-yl] -2-hydroxy-5-carboxymethoxy-1,2,3,4-tetrahydronaphthalene
FABMS (m/z): 533 (M$^+$+1)
IR (Nujol): 1600 cm$^{-1}$
NMR (DMSO-d$_6$, δ): 1.5–2.4 (5H, m), 2.8–3.0 (3H, m), 3.8–3.9 (1H, m), 3.9–4.2 (3H, m), 4.8–5.0 (2H, m), 6.49 (1H, d, J=8 Hz), 6.98 (1H, d, J=8 Hz), 7.22 (1H, d, J=8 Hz), 7.3–7.6 (10H, m)

(36) Sodium salt of 1-[2-(4,5-diphenyloxazol-2-yl) tetrahydrofuran-3-yl]-5-carboxymethoxy-3,4-dihydronaphthalene
FABMS (m/z): 516 (M$^+$+1)
IR (Nujol) 1600 cm$^{-1}$
NMR (DMSO-d$_6$, δ): 1.7–2.4 (3H, m), 2.7–2.9 (1H, m), 4.09 (2H, s), 4.37 (1H, m), 5.38 (1H, d, J=8.0 Hz), 5.92 (1H, m), 6.6–6.8 (1H, m), 7.0–7.8 (12H, m)

(37) Sodium salt of 1-[2-(4,5-diphenyloxazol-2-yl) tetrahydrofuran-3-yl!-5-carboxymethoxy-1,2,3,4-tetrahydronaphthalene
FABMS (m/z): 518 (M$^+$+1)
IR (Nujol): 1600 cm$^{-1}$
NMR (DMSO-d$_6$, δ): 1.4–2.2 (5H, m), 2.7–2.9 (2H, m), 3.8–4.0 (2H, m), 4.12 (2H, s), 4.0–4.2 (1H, m), 5.25 (1H, d, J=6.8 Hz), 6.5–6.8 (2H, m), 6.93 (1H, t, J=8 Hz), 7.3–7.8 (10H, m)

(38) Sodium salt of 1-(4-(4,5-diphenyloxazol-2-yl)-2-oxoazetidin-1-yl]-5-carboxymethoxy-1,2,3,4-tetrahydronaphthalene
FABMS (m/z): 517 (M$^+$+1)
IR (Nujol) 1740, 1600 cm$^{-1}$
NMR (DMSO-d$_6$, δ) 1.4–2.2 (4H, m), 2.3–2.8 (2H, m), 3.2–3.5 (2H, m), 3.8–4.1 (2H, m), 4.6–5.0 (2H, m), 6.60 (1H, d, J=8.0 Hz), 6.80 (1H, d, J=8.0 Hz), 7.08 (1H, t, J=8.0 Hz) 7.2–7.6 (10H, m)

(39) Sodium salt of 1-[2-(4,5-diphenyloxazol-2-yl)azetidin-1-yl]-5-carboxymethoxy-1,2,3,4-tetrahydronaphthalene
FABMS (m/z): 503 (M$^+$+1)
IR (Nujol) 1600 cm$^{-1}$
NMR (DMSO-d$_6$, δ): 1.4–2.9 (8H, m), 3.9–4.0 (1H, m), 4.10 (2H, s), 4.3–4.7 (1H, m), 6.58 (1H, d, J=8.0 Hz), 6.68 (1H, d, J=8.0 Hz), 6.95 (1H, t, J=8 Hz), 7.2–7.6 (10H, m)

(40) Sodium salt of 1-[2-(4,5-diphenyloxazol-2-yl) piperidin-1-yl]-5-carboxymethoxy-1,2,3,4-tetrahydronaphthalene FABMS (m/z): 531 (M$^+$+1)
IR (Nujol): 1600 cm$^{-1}$
NMR (DMSO-d$_6$, δ): 1.4–3.1 (12H, m), 3.8–4.0 (1H, m), 4.00, 4.10 (2H, each s), 4.1–4.3 (1H, m), 6.43, 6.51 (1H, each d, J=8.0 Hz), 6.90, 7.02 (1H, each t, J=8.0 Hz), 7.15, 7.26 (1H, each d, J=8 Hz), 7.2–7.8 (10H, m)

(41) Sodium [3-[[2-(4,5-diphenyloxazol-2-yl)-1-cyclopenten-1-yl]carbonyl]phenoxy]acetate
FABMS (m/z): 488 (M$^+$+1)
IR (Nujol): 1660, 1600 cm$^{-1}$
NMR (DMSO-d$_6$, δ): 2.0–2.3 (2H, m), 2.8–3.2 (4H, m), 4.15 (2H, s), 6.9–7.2 (4H, m), 7.2–7.5 (10H, m)

(42) Sodium [3-[[2-(4,5-diphenyloxazol-2-yl)-2-cyclopenten-1-yl]carbonyl]phenoxy]acetate
FABMS (m/z): 488 (M$^+$+1)
NMR (DMSO-d$_6$, δ): 1.9–2.1 (2H, m), 2.6–2.8 (2H, m), 4.17 (2H, s), 6.8–7.2 (4H, m), 7.2–7.6 (10H, m)

(43) Sodium salt of 2-(4,5-diphenyloxazol-2-yl)-3-(3-carboxymethoxybenzyl)bicyclo[2.2.1]heptane
FABMS (m/z): 502 (M$^+$+1)
IR (Nujol): 1600 cm$^{-1}$
NMR (DMSO-d$_6$, δ): 1.2–3.0 (11H, m), 4.02 (2H, s), 6.3–6.8 (3H, m), 6.95 (1H, t, J=8.0 Hz), 7.3–7.8 (10H, m)

(44) Sodium [3-[[2-(4,5-diphenyloxazol-2-yl)cyclooctan-1-yl]methyl]phenoxy]acetate
FABMS (m/z): 518 (M$^+$+1)
IR (Nujol): 1600 cm$^{-1}$
NMR (DMSO-d$_6$, δ): 1.2–3.0 (15H, m), 4.05, 4.10 (2H, each s), 6.4–7.1 (4H, m), 7.2–7.8 (10H, m)

What is claimed is:

1. A compound of the formula:

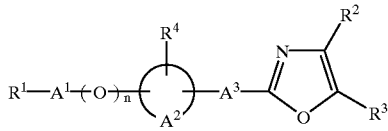

wherein

R$^1$ is carboxy or protected carboxy,
R$^2$ is aryl which may have suitable substituent(s),
R$^3$ is aryl which may have suitable substituent(s),
R$^4$ is hydrogen, lower alkyl, hydroxy or aryl,
A$^1$ is lower alkylene,

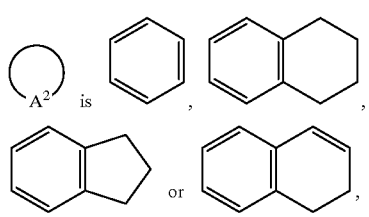

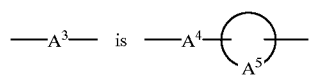

(in which —A$^4$— is bond, —CH$_2$— or —CO—, and

is cyclo(C$_5$–C$_8$)alkene, cyclo(C$_7$–C$_8$)alkane, bicycloheptane, bicycloheptene, tetrahydrofuran, tetrahydrothiophene, azetidine, pyrrolidine or piperidine, each of which may have suitable substituent(s)) or —X—A$^6$— [in which —X— is —O—, —S— or

(in which R$^5$ is hydrogen, lower alkyl or acyl) and
A$^6$ is lower alkylene which may have suitable substituent(s)], and
n is 0 or 1, and a pharmaceutically acceptable salt thereof.

2. A compound of claim 1, wherein
R$^2$ is phenyl or lower alkylphenyl,
R$^3$ is phenyl or lower alkylphenyl,
R$^4$ is hydrogen, lower alkyl, hydroxy or phenyl, and
—A$^3$— is

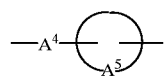

(in which —A$^4$— is bond, —CH$_2$— or —CO—, and

is cyclo(C$_5$–C$_8$)alkene, cyclo(C$_7$–C$_8$)alkane, bicycloheptane, bicycloheptene, tetrahydrofuran, tetrahydrothiophene, azetidine, pyrrolidine or piperidine, each of which may have one to three suitable substituent(s) selected from the group consisting of imino, oxo, acyl and imino protective group) or —X—A$^6$— [in which —X— is —O—, —S— or

(in which R$^5$ is hydrogen, lower alkyl or acyl) and
A$^6$ is lower alkylene which may have one to three suitable substituent(s) selected from the group consisting of lower alkyl and hydroxy(lower)alkyl].

3. A compound of claim 2, wherein

—A$^3$— is 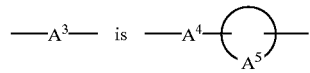

(in which —A⁴— is bond, —CH₂— or —CO—, and

is cyclo(C₅–C₈)alkene, cyclo(C₇–C₈)alkane, bicyclo[2.2.1]heptane, bicyclo[2.2.1]heptene, tetrahydrofuran, tetrahydrothiophene, azetidine, pyrrolidine or piperidine, each of which may have one or two suitable substituent(s) selected from the group consisting of imino, oxo, lower alkanoyl and mono(or di or tri)phenyl(lower)alkyl) or —X—A⁶— [in which —X— is —O—, —S— or

(in which R⁵ is hydrogen, lower alkyl or lower alkanoyl) and

A⁶ is lower alkylene which may have a suitable substituent selected from the group consisting of lower alkyl and hydroxy(lower)alkyl].

4. A compound of claim 3, wherein

R¹ is carboxy or esterified carboxy, and

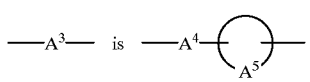

(in which —A⁴— is bond, —CH₂— or —CO—, and

is cyclo(C₅–C₈)alkene, cyclo(C₇–C₈)alkane, bicyclo[2.2.1]heptane, bicyclo(2.2.1]hept-2-ene, tetrahydrofuran, tetrahydrothiophene, azetidine, pyrrolidine or piperidine, each of which may have one or two suitable substituent(s) selected from the group consisting of imino, oxo, lower alkanoyl and phenyl(lower)alkyl) or —X—A⁶— [in which —X— is —O—, —S— or

(in which R⁵ is hydrogen, lower alkyl or lower alkanoyl) and

A⁶ is lower alkylene which may have a suitable substituent selected from the group consisting of lower alkyl and hydroxy(lower)alkyl].

5. A compound of claim 4, wherein

R¹ is carboxy or lower alkoxycarbonyl,

R² is phenyl or C₁–C₄ alkylphenyl,

R³ is phenyl or C₁–C₄ alkylphenyl,

R⁴ is hydrogen, C₁–C₄ alkyl, hydroxy or phenyl,

A¹ is C₁–C₄ alkylene, and

—A³— is

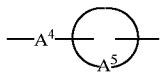

(in which —A⁴— is bond, —CH₂— or —CO—, and

is cyclo(C₅–C₈)alkene, cyclo(C₇–C₈)alkane, bicyclo[2.2.1]heptane, bicyclo[2.2.1]hept-2-ene, tetrahydrofuran, tetrahydrothiophene, azetidine, pyrrolidine or piperidine, each of which may have one or two suitable substituent(s) selected from the group consisting of imino, oxo, C₁–C₄ alkanoyl and phenyl(C₁–C₄)alkyl) or —X—A⁶— [in which —X— is —O—, —S— or

(in which R⁵ is hydrogen, C₁–C₄ alkyl or C₁–C₄ alkanoyl) and

A⁶ is C₁–C₄ alkylene which may have a suitable substituent selected from the group consisting of C₁–C₄ alkyl and hydroxy-(C₁–C₄)alkyl].

6. A compound of claim 1, which is a compound of the formula:

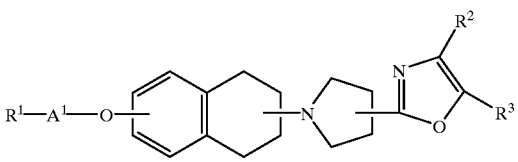

wherein

R¹ is carboxy or protected carboxy,

R² is phenyl or lower alkylphenyl,

R³ is phenyl or lower alkylphenyl and

A¹ is lower alkylene, or a pharmaceutically acceptable salt thereof.

7. A compound of claim 6, which is selected from the group consisting of (1) sodium salt of (1R)-1-[(2R)-2-(4,5-diphenyloxazol-2-yl)pyrrolidin-1-yl]-5-carboxymethoxy-1,2,3,4-tetrahydronaphthalene and (2) sodium salt of (1S)-1-[(2S)-2-(4,5-diphenyloxazol-2-yl)pyrrolidin-1-yl]-5-carboxymethoxy-1,2,3,4-tetrahydronaphthalene.

8. A compound of claim 1, which is a compound of the formula:

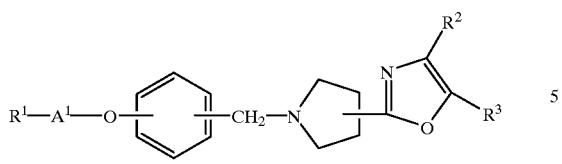

wherein

R¹ is carboxy or protected carboxy,

R² is phenyl or lower alkylphenyl,

R³ is phenyl or lower alkylphenyl and

A¹ is lower alkylene, or a pharmaceutically acceptable salt thereof.

9. A compound of claim 8, which is selected from the group consisting of (1) sodium [3-[[(2R)-2-(4,5-diphenyloxazol-2-yl)pyrrolidin-1-yl]methyl]phenoxy]acetate and (2) sodium [3-[[(2S)-2-(4,5-diphenyloxazol-2-yl)pyrrolidin-1-yl]methyl]phenoxy]acetate.

10. A pharmaceutical composition which comprises, as an active ingredient, a compound of claim 1 or a pharmaceutically acceptable salt thereof in admixture with pharmaceutically acceptable carriers.

11. A method for treating or preventing arterial obstruction, restenosis after percutaneous transluminal coronary angioplasty, hepatitis, hepatic insufficiency, hepatic cirrhosis, arteriosclerosis, cerebrovascular disease or ischemic heart disease which comprises administering a compound of claim 1 or a pharmaceutically acceptable salt thereof to humans or animals.

12. The method of claim 11, wherein said compound is a prostaglandin I₂ agonist.

13. A method for agonising prostaglandin I2 activity, which comprises administering an effective amount of a compound of claim 1 or pharmaceutically acceptable salts thereof to human or animals.

14. A method for inhibiting platelet aggregation, which comprises administering an effective amount of a compound of claim 1 or pharmaceutically acceptable salts thereof to human or animals.

15. A method for suppressing blood pressure, which comprises administering an effective amount of a compound of claim 1 or pharmaceutically acceptable salts thereof to humans or animals.

16. A process for preparing a compound of the formula:

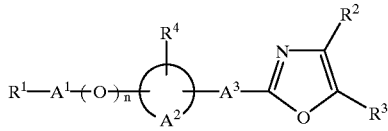

wherein

R¹ is carboxy or protected carboxy,

R² is aryl which may have suitable substituent(s),

R³ is aryl which may have suitable substituent(s),

R⁴ is hydrogen, lower alkyl, hydroxy or aryl,

A¹ is lower alkylene,

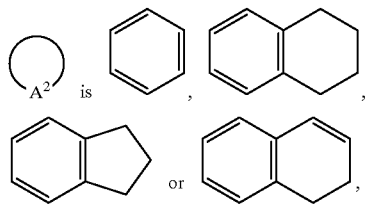

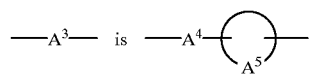

(in which —A⁴— is bond, —CH₂— or —CO—, and

is cyclo(C₅–C₈)alkene, cyclo(C₇–C₈)alkane, bicycloheptane, bicycloheptene, tetrahydrofuran, tetrahydrothiophene, azetidine, pyrrolidine or piperidine, each of which may have suitable substituent(s)) or —X—A⁶— [in which —X— is —O—, —S— or

(in which R⁵ is hydrogen, lower alkyl or acyl) and

A⁶ is lower alkylene which may have suitable substituent(s)], and n is 0 or 1, or a salt thereof, which comprises (1) reacting a compound of the formula:

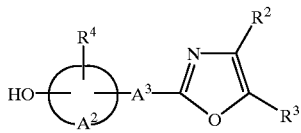

wherein R², R³, R⁴,

and —A³— are each as defined above, or a salt thereof with a compound of the formula:

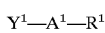

wherein R¹ and A¹ are each as defined above, and Y¹ is acid residue, or a salt thereof to give a compound of the formula:

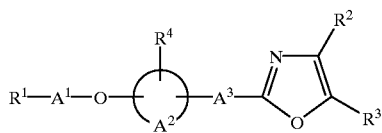

wherein $R^1$, $R^2$, $R^3$, $R^4$, $A^1$,

and —$A^3$— are each as defined above, or a salt thereof, or
(2) subjecting a compound of the formula:

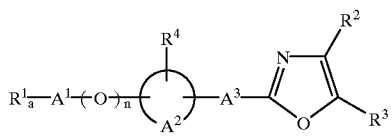

wherein $R^2$, $R^3$, $R^4$, n, $A^1$,

and —$A^3$— are each as defined above, and
$R_a^1$ is protected carboxy, or a salt thereof to elimination reaction of the carboxy protective group to give a compound of the formula:

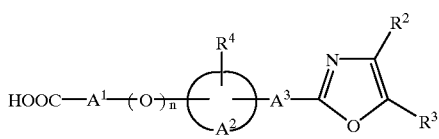

wherein $R^2$, $R_3$, $R^4$, n, $A^1$,

and —$A^3$— are each as defined above, or a salt thereof, or
(3) subjecting a compound of the formula:

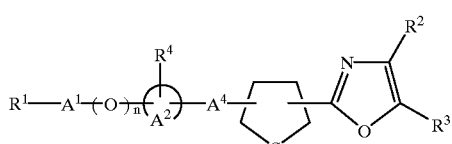

wherein $R^1$, $R^2$, $R^3$, $R^4$, n, $A^1$,

and —$A^4$— are each as defined above, or a salt thereof to oxidation reaction to give a compound of the formula:

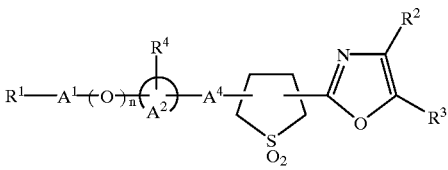

wherein $R^1$, $R^2$, $R^3$, $R^4$, n, $A^1$,

and —$A^4$— are each as defined above, or a salt thereof, or
(4) subjecting a compound of the formula:

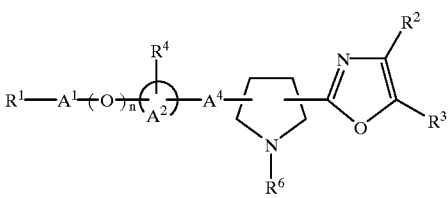

wherein $R^1$, $R^2$, $R^3$, $R^4$, n, $A^1$,

and —$A^4$— are each as defined above, and
$R^6$ is imino protective group, or a salt thereof to elimination reaction of the imino protective group to give a compound of the formula:

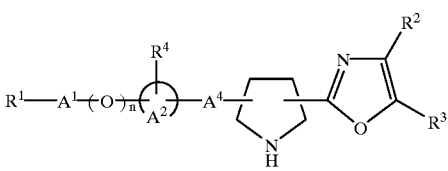

wherein $R^1$, $R^2$, $R^3$, $R^4$, n, $A^1$,

and —$A^4$— are each as defined above, or a salt thereof, or
(5) subjecting a compound of the formula:

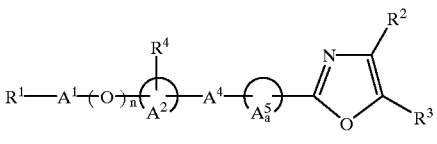

wherein $R^1$, $R^2$, $R^3$, $R^4$, n, $A^1$,

and —A⁴— are each as defined above, and is cyclo(C₇–C₈)alkene, or a salt thereof to reduction reaction to give a compound of the formula:

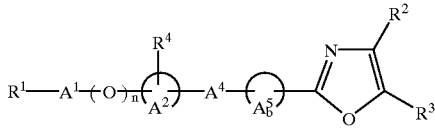

wherein R¹, R², R³, R⁴, n, A¹, and —A⁴— are each as defined above, and is cyclo(C₇–C₈)alkane, or a salt thereof, or
(6) reacting a compound of the formula:

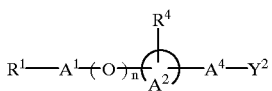

wherein R¹, R⁴, n, A¹, and —A⁴— are each as defined above, and
Y² is halogen, or a salt thereof with a compound of the formula:

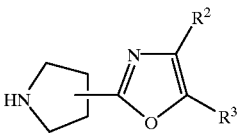

wherein R² and R³ are each as defined above, or a salt thereof to give a compound of the formula:

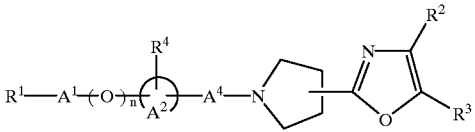

wherein R¹, R², R³, R⁴, n, A¹, and —A⁴— are each as defined above, or a salt thereof.

17. A process for preparing a pharmaceutical composition which comprises admixing a compound of claim 1 or a pharmaceutically acceptable salt thereof with a pharmaceutically acceptable carrier.

* * * * *